US012275994B2

(12) United States Patent
Steelman et al.

(10) Patent No.: US 12,275,994 B2
(45) Date of Patent: Apr. 15, 2025

(54) METHODS AND COMPOSITIONS FOR THE ANALYSIS OF CANCER BIOMARKERS

(71) Applicant: Clear Gene, Inc., San Carlos, CA (US)

(72) Inventors: Brandon Steelman, Redwood City, CA (US); Julia Meyer, Redwood City, CA (US)

(73) Assignee: Clear Gene, Inc., San Carlos, CA (US)

( * ) Notice: Subject to any disclaimer, the term of this patent is extended or adjusted under 35 U.S.C. 154(b) by 0 days.

(21) Appl. No.: 16/016,460

(22) Filed: Jun. 22, 2018

(65) Prior Publication Data

US 2018/0371553 A1 Dec. 27, 2018

Related U.S. Application Data

(60) Provisional application No. 62/523,709, filed on Jun. 22, 2017.

(51) Int. Cl.
*C12Q 1/6886* (2018.01)
*G16B 20/00* (2019.01)
*G16B 40/00* (2019.01)
*G16B 40/20* (2019.01)

(52) U.S. Cl.
CPC ........... *C12Q 1/6886* (2013.01); *G16B 20/00* (2019.02); *G16B 40/00* (2019.02); *G16B 40/20* (2019.02); *C12Q 2600/158* (2013.01)

(58) Field of Classification Search
None
See application file for complete search history.

(56) References Cited

U.S. PATENT DOCUMENTS

| | | | |
|---|---|---|---|
| 5,122,284 A | 6/1992 | Braynin et al. | |
| 5,304,487 A | 4/1994 | Wilding et al. | |
| 5,496,562 A | 3/1996 | Burgoyne | |
| 5,756,126 A | 5/1998 | Burgoyne | |
| 5,763,181 A | 6/1998 | Han et al. | |
| 6,030,581 A | 2/2000 | Virtanen | |
| 6,197,595 B1 | 3/2001 | Anderson et al. | |
| 6,664,379 B1 | 12/2003 | Kudlicki et al. | |
| 6,682,889 B1 | 1/2004 | Wang et al. | |
| 7,001,724 B1 | 2/2006 | Greenfield, I et al. | |
| 7,112,406 B2 | 9/2006 | Behlke et al. | |
| 7,135,291 B2 | 11/2006 | Sagawa et al. | |
| 7,208,313 B2 | 4/2007 | McCart et al. | |
| 8,202,697 B2 | 6/2012 | Holmes | |
| 8,319,398 B2 | 11/2012 | Vivek et al. | |
| 8,506,947 B2 | 8/2013 | McCart et al. | |
| 8,647,742 B2 | 2/2014 | Dendukuri et al. | |
| 8,911,948 B2 | 12/2014 | Walder et al. | |
| 9,434,988 B2 | 9/2016 | Behlke et al. | |
| 9,984,201 B2 | 5/2018 | Zhang et al. | |
| 11,060,149 B2 | 7/2021 | Steelman | |
| 2001/0018513 A1 | 8/2001 | Baker | |
| 2001/0051344 A1* | 12/2001 | Shalon | B01L 3/0244 435/6.11 |
| 2003/0031681 A1 | 2/2003 | McCart et al. | |
| 2003/0190602 A1* | 10/2003 | Pressman | C12Q 1/6809 435/5 |
| 2006/0166231 A1* | 7/2006 | Baker | G16B 20/00 435/6.14 |
| 2006/0246575 A1 | 11/2006 | Lancaster et al. | |
| 2007/0031867 A1 | 2/2007 | Hoon et al. | |
| 2007/0077582 A1 | 4/2007 | Slepnev | |
| 2007/0154458 A1 | 7/2007 | McCart et al. | |
| 2007/0213939 A1 | 9/2007 | Liew et al. | |
| 2008/0068643 A1 | 3/2008 | Yasunaga | |
| 2008/0305528 A1 | 12/2008 | Baker | |
| 2010/0047130 A1 | 2/2010 | Ong et al. | |
| 2010/0240123 A1 | 9/2010 | Belgrader | |
| 2010/0256465 A1 | 10/2010 | Bernstein et al. | |
| 2011/0091987 A1 | 4/2011 | Weissleder et al. | |
| 2011/0123990 A1* | 5/2011 | Baker | C12Q 1/6886 435/6.12 |
| 2011/0151435 A1 | 6/2011 | Mehra et al. | |
| 2012/0123205 A1 | 5/2012 | Nie et al. | |
| 2012/0308484 A1 | 12/2012 | Szalay et al. | |
| 2013/0040852 A1* | 2/2013 | Anastassiou | G01N 33/57484 506/9 |
| 2013/0137107 A1 | 5/2013 | Ko et al. | |
| 2013/0209473 A1 | 8/2013 | De et al. | |
| 2013/0274136 A1 | 10/2013 | McDevitt et al. | |
| 2013/0280706 A1 | 10/2013 | Judice | |
| 2013/0295580 A1 | 11/2013 | McDevitt et al. | |
| 2013/0295581 A1* | 11/2013 | Chapman | C12Q 1/6886 435/6.14 |
| 2013/0332083 A1 | 12/2013 | Van | |
| 2013/0337462 A1 | 12/2013 | Mergemeier | |
| 2014/0018253 A1* | 1/2014 | Griffith | C12Q 1/6886 435/6.12 |
| 2014/0031254 A1 | 1/2014 | Pestova et al. | |
| 2014/0243239 A1 | 8/2014 | Johnson et al. | |
| 2014/0329704 A1 | 11/2014 | Melton et al. | |
| 2015/0299797 A1* | 10/2015 | Bild | C12Q 1/6886 506/9 |
| 2015/0307947 A1* | 10/2015 | Basu | C12Q 1/6886 506/2 |
| 2015/0366835 A1 | 12/2015 | Pogue-Geile et al. | |
| 2016/0097102 A1 | 4/2016 | Suh et al. | |
| 2016/0146818 A1 | 5/2016 | Goodison et al. | |
| 2016/0153053 A1 | 6/2016 | Skog et al. | |
| 2016/0258960 A1 | 9/2016 | Kruk | |
| 2017/0218455 A1 | 8/2017 | Steelman | |

FOREIGN PATENT DOCUMENTS

| | | | |
|---|---|---|---|
| EP | 1312682 A1 | 5/2003 | |
| EP | 1420069 A1 | 5/2004 | |

(Continued)

OTHER PUBLICATIONS

Cobb et al (Crit Care Med 2002 vol. 30 p. 2711) (Year: 2002).*

(Continued)

*Primary Examiner* — Katherine D Salmon
(74) *Attorney, Agent, or Firm* — Larisa Migachyov

(57) ABSTRACT

Described herein are improved methods, compositions, and kits for analysis of minimal residual solid tumor.

29 Claims, 17 Drawing Sheets
Specification includes a Sequence Listing.

(56) References Cited

FOREIGN PATENT DOCUMENTS

| | | |
|---|---|---|
| EP | 2028270 B1 | 2/2012 |
| EP | 2032722 B1 | 8/2013 |
| EP | 3158085 A2 | 4/2017 |
| GB | 2513275 A | 10/2014 |
| WO | WO-2008043987 A2 | 4/2008 |
| WO | WO-2008043987 A3 | 9/2008 |
| WO | WO-2010009074 A2 | 1/2010 |
| WO | WO-2012001607 A1 | 1/2012 |
| WO | WO-2013010134 A2 | 1/2013 |
| WO | WO-2013025952 A2 | 2/2013 |
| WO | WO-2014093934 A1 | 6/2014 |
| WO | WO-2015171741 A1 | 11/2015 |
| WO | WO-2015195949 A2 | 12/2015 |
| WO | WO-2015195949 A3 | 2/2016 |
| WO | WO-2016115530 A1 | 7/2016 |
| WO | WO-2017106790 A1 | 6/2017 |
| WO | WO-2019245587 A1 | 12/2019 |

OTHER PUBLICATIONS

Lucentini (The Scientist, 2004, vol. 18, p. 20) (Year: 2004).*
Buchholz, et al. Margins for breast-conserving surgery with whole-breast irradiation in stage I and II invasive breast cancer: American Society of Clinical Oncology endorsement of the Society of Surgical Oncology/American Society for Radiation Oncology consensus guideline. J Clin Oncol. May 10, 2014;32(14):1502-6. PMID: 24711553.
Dabbs, D. J. Breast Pathology. Elsevier Health Sciences, Nov. 4, 2016, p. 107.
Prowell, et al. Pathological complete response and accelerated drug approval in early breast cancer. N Engl J Med. Jun. 28, 2012;366(26):2438-41. doi: 10.1056/NEJMp1205737. Epub May 30, 2012.
Rose, et al. Perils of the Pathologic Complete Response. J Clin Oncol. Nov. 20, 2016;34(33):3959-3962. doi: 10.1200/JCO.2016. 68.1718. Epub Oct. 31, 2016. PMID: 27551115.
Voogd, et al. Differences in risk factors for local and distant recurrence after breast-conserving therapy or mastectomy for stage I and II breast cancer: pooled results of two large European randomized trials. J Clin Oncol. Mar. 15, 2001;19(6):1688-97.
Yared, et al. Recommendations for sentinel lymph node processing in breast cancer. Am J Surg Pathol. Mar. 2002;26(3):377-82. PMID: 11859211.
Bastien, et al. PAM50 breast cancer subtyping by RT-qPCR and concordance with standard clinical molecular markers. BMC Med Genomics. Oct. 4, 2012;5:44. PMCID: PMC3487945.
Boldisen, et al. Importance of margin width in breast-conserving treatment of early breast cancer. J Surg Oncol. May 2016;113(6):609-15. PMID: 26991020.
Co-pending U.S. Appl. No. 16/061,517, filed Jun. 12, 2018.
Cortazar, et al. Pathological complete response and long-term clinical benefit in breast cancer: the CTNeoBC pooled analysis. Lancet. Jul. 12, 2014;384(9938):164-72. doi: 10.1016/S0140-6736(13)62422-8. Epub Feb. 14, 2014.
Cserni, et al. Discrepancies in current practice of pathological evaluation of sentinel lymph nodes in breast cancer. Results of a questionnaire based survey by the European Working Group for Breast Screening Pathology. J Clin Pathol. Jul. 2004;57(7):695-701. PMCID: PMC1770358.
Cserni, G. Complete sectioning of axillary sentinel nodes in patients with breast cancer. Analysis of two different step sectioning and immunohistochemistry protocols in 246 patients. J Clin Pathol. Dec. 2002;55(12):926-31. PMID: 12461060.
Cserni, G. Metastases in axillary sentinel lymph nodes in breast cancer as detected by intensive histopathological work up. J Clin Pathol. Dec. 1999;52(12):922-4. PMID: 10711258.
Dibiase, et al. Influence of radiation dose on positive surgical margins in women undergoing breast conservation therapy. Int J Radiat Oncol Biol Phys. Jul. 1, 2002;53(3):680-6. PMID: 12062612.

Gradishar, et al. Invasive Breast Cancer Version 1.2016. National Comprehensive Cancer Network (NCCN). NCCN Clinical Practice Guidelines in Oncology (NCCN Guidelines). 2016.
Houssami, et al. Meta-analysis of the impact of surgical margins on local recurrence in women with early-stage invasive breast cancer treated with breast-conserving therapy. Eur J Cancer. Dec. 2010;46(18):3219-32. PMID: 20817513.
Houssami, et al. The association of surgical margins and local recurrence in women with early-stage invasive breast cancer treated with breast-conserving therapy: a meta-analysis. Ann Surg Oncol. Mar. 2014;21(3):717-30. PMID: 24473640.
Koboldt, et al. Comprehensive molecular portraits of human breast tumours. Nature 2012 vol. 490, pp. 61-70.
Lalkhen, et al. Clinical Tests: Sensitivity and Specificity. Continuing Education in Anaesthesia Critical Care and Pain. 2008;8(6):221-3. doi: 10.1093/bjaceaccp/mkn041.
Meric, et al. Positive surgical margins and ipsilateral breast tumor recurrence predict disease-specific survival after breast-conserving therapy. Cancer. Feb. 15, 2003;97(4):926-33. PMID: 12569592.
Moran, et al. Society of Surgical Oncology-American Society for Radiation Oncology consensus guideline on margins for breast-conserving surgery with whole-breast irradiation in stages I and II invasive breast cancer.Int J Radiat Oncol Biol Phys. Mar. 1, 2014;88(3):553-64. doi: 10.1016/j.ijrobp.2013.11.012.
Radmacher, et al. (2003). Pitfalls in the Use of DNA Microarray Data for Diagnostic and Prognostic Classification. Journal of the National Cancer Institute, 95(1), 14-18.
Singletary, SE. Surgical margins in patients with early-stage breast cancer treated with breast conservation therapy. Am J Surg. Nov. 2002; 184(5):383-93. PMID: 12433599.
Chagpar, et al. A Randomized, Controlled Trial of Cavity Shave Margins in Breast Cancer. N Engl J Med. Aug. 6, 2015;373(6):503-10.
Steelman, B. Trump: polls right, models wrong. Nature. Nov. 30, 2016;540(7631):39. PMID: 27905426.
Tang, et al. Lumpectomy specimen margins are not reliable in predicting residual disease in breast conserving surgery. Am J Surg. Jul. 2015;210(1):93-8. PMID: 25613784.
The American Society of Breast Surgeons. Position Statement on Breast Cancer Lumpectomy Margins. Approved Jan. 16, 2013. Last accessed May 22, 2016. Available at: https://www.breastsurgeons. org/new_layout/about/statements/PDF_Statements/Lumpectomy_Margins.pdf.
Treseler, et al. Pathologic analysis of the sentinel lymph node. Surg Clin North Am. Dec. 2000;80(6):1695-719. PMID: 11140868.
U.S. Department of Health and Human Services, Food and Drug Administration. BLA Approval Letter to Genetech, Inc. Dated Jun. 8, 2012. Available at: https://www.accessdata.fda.gov/drugsatfda_docs/appletter/2012/125409Orig1s000ltr.pdf.
U.S. Department of Health and Human Services, Food and Drug Administration, Center for Drug Evaluation and Research. Guidance for Industry: Pathological Complete Response in Neoadjuvant Treatment of High-Risk Early-Stage Breast Cancer: Use as an Endpoint to Support Accelerated Approval. Oct. 2014. https://www.fda.gov/downloads/Drugs/GuidanceComplianceRegulatoryInformation/Guidances/UCM305501.pdf.
Van Diest, P.J. Histopathological workup of sentinel lymph nodes: how much is enough? J Clin Pathol. Dec. 1999;52(12):871-3. PMID: 10711247.
Viale, et al. Intraoperative examination of axillary sentinel lymph nodes in breast carcinoma patients. Cancer. Jun. 1, 1999;85(11):2433-8. PMID: 10357414.
Weaver, D. L. Pathology evaluation of sentinel lymph nodes in breast cancer: protocol recommendations and rationale. Modern Pathology (2010) 23, S26-S32; doi:10.1038/modpathol.2010.36.
Aha et al. Instance-Based Learning Algorithms Machine Learning 1991 vol. 6: pp. 37-66.
Amancio et al. A Systematic Comparison of Supervised Classifiers. PLoS One 2014 vol. 9: e94137.
Ausubel, et al. Current Protocols in Molecular Biology (1987).
Bakhshandeh, et al. Use of imprint cytology for assessment of surgical margins in lumpectomy specimens of breast cancer patients. Diagn Cytopathol. Oct. 2007; 35(10) :656-9.

(56) References Cited

OTHER PUBLICATIONS

Bignotti, et al. Gene expression profile of ovarian serous papillary carcinomas: identification of metastasis-associated genes. Am J Obstet Gynecol. Mar. 2007;196(3):245.e1-11.

Castano-Alvarez, et al. Electroactive intercalators for DNA analysis on microchip electrophoresis. Electrophoresis. Dec. 2007;28(24):4679-89.

Cooney, et al. A plastic, disposable microfluidic flow cell for coupled on-chip PCR and microarray detection of infectious agents. Biomed Microdevices. Feb. 2012;14(1):45-53. doi: 10.1007/s10544-011-9584-9.

Cox, et al. Touch Preparation Cytology of Breast Lumpectomy Margins with Histologic Correlation. Arch Surg. 1991. vol. 126, pp. 490-493.

Crawley. Statistics: An Introduction Using R, (John Wiley and Sons, Ltd, 2005).

Creager, et al. Intraoperative evaluation of lumpectomy margins by imprint cytology with histologic correlation: a community hospital experience. Archives of Pathology & Laboratory Medicine. 2002. vol. 126, No. 7, pp. 846-848.

Defever, et al. Real-time electrochemical PCR with a DNA intercalating redox probe. Anal Chem. Mar. 1, 2011;83(5):1815-21. doi: 10.1021/ac1033374. Epub Jan. 31, 2011.

Dhage, et al. A genomic ruler to assess oncogenic transition between breast tumor and stroma. PLoS One. 2018; 13(10): e0205602.

D'halluin F, et al. Intra-operative touch preparation cytology following lumpectomy for breast cancer: a series of 400 procedures. Breast. Aug. 2009; 18(4):248-53.

Dogan, et al. Use of touch imprint cytology as a simple method to enrich tumor cells for molecular analysis. Cancer cytopathology 121.7 (2013): 354-360.

EP 15809388.0 Extended European Search Report and Search Opinion dated Dec. 21, 2017.

EP15809388 The extended European Search Report dated Dec. 21, 2017.

EP16876870.3 The Extended European Search Report dated Apr. 23, 2019.

Ferrario, et al. Prospective of Using Nano-Structured High Performances Sensors Based on Polymer Nano-Imprinting Technology for Chemical and Biomedical Applications. Sensors and Biosensors 54; 2010, pp. 197-200.

Freshney, et al. Culture of Animal Cells: A Manual of Basic Technique and Specialized Applications, 6th Edition. 2010.

Gage, et al. Pathologic margin involvement and the risk of recurrence in patients treated with breast-conserving therapy. Cancer. Nov. 1, 1996;78(9):1921-8.

Gansen, et al. Digital Lamp in a sample self-digitization (SD) chip. Lab Chip. Jun. 21, 2012;12(12):2247-54. doi: 10.1039/c2lc21247a. Epub Mar. 7, 2012.

Genbank Accession NM_080282: *Homo sapiens* ATP-Binding Cassette, Sub-Family A (ABC1) Member 10 mRNA. Feb. 26, 2014; pp. 1-7.

Gill, et al. Nucleic acid isothermal amplification technologies: a review. Nucleosides Nucleotides Nucleic Acids. Mar. 2008;27(3):224-43. doi: 10.1080/15257770701845204.

Hastie, et al. Elements of Statistical Learning, 2nd edition (2009).

Hayashi, et al. Paired Box 5 Methylation Detection by Droplet Digital PCR for Ultra-Sensitive Deep Surgical Margins Analysis of Head and Neck Squamous Cell Carcinoma. Cancer Prev Res, Aug. 24, 2015 (Aug. 24, 2015), vol. 8, pp. 1017-1026.

Horvath, et al. Novel insights into breast cancer genetic variance through RNA sequencing. Scientific reports 3 (2013).

Huan, et al. Micro-NMR for Rapid Molecular Analysis of Human Tumor Samples. Sci Transl Med. Feb. 23, 2011; 3(71): 71ra16. doi:10.1126/scitranslmed.3002048.

Huang, et al. fM to aM nucleic acid amplification for molecular diagnostics in a non-stick-coated metal microfluidic bioreactor. Scientific Reports 4, Article No. 7344. Dec. 2014.).

International search report and written opinion dated Dec. 8, 2015 for PCT Application No. PCT/US15/36480.

Invitrogen. ChargeSwitch® Forensic DNA Purification Kits: For purification of genomic DNA from forensic samples. Version A. Jan. 3, 2005.

Johnson & Johnson. Instructions for Use for GeneSearch Breast Lymph Node (BLN) Test Kit and GeneSearch RNA Sample Preparation Kit. Apr. 28, 2006. Available at http://www.fda.gov/ohrms/dockets/ac/06/briefing/2006-4249b1_02.pdf. Accessed Feb. 2, 2017.

Kale, et al. Cross-Validation and Mean-Square Stability. Symposium on Innovations in Computer Science. Jan. 7, 2011.).

Kim, et al. Ultrafast colorimetric detection of nucleic acids based on the inhibition of the oxidase activity of cerium oxide nanoparticles. Chem. Commun., 2014,50, 9577-9580.

Kinkaid, et al. Can touch imprint cytology replace fine needle aspiration within current clinical practice? Breast Cancer Research 2010, 12(3):P14. doi:10.1186/bcr2667.

Kivlehan, et al. Real-time electrochemical monitoring of isothermal helicase-dependent amplification of nucleic acids.Analyst. Sep. 21, 2011;136(18):3635-42. doi: 10.1039/c1an15289k. Epub Jul. 27, 2011.

Klimberg Vs, et al. Use of touch preps for diagnosis and evaluation of surgical margins in breast cancer. Ann Surg Oncol. 1998;5: 220-226.

Liu, et al. A low-cost microfluidic chip for rapid genotyping of malaria-transmitting mosquitoes. PLoS One. 2012;7(8):e42222. doi: 10.1371/journal.pone.0042222. Epub Aug. 3, 2012.

McPherson, et al. PCR 2: A Practical Approach (1995).

Narrandes, et al. Gene Expression Detection Assay for Cancer Clinical Use. J Cancer. 2018; 9(13): 2249-2265.

Neuzil, et al. Ultra fast miniaturized real-time PCR: 40 cycles in less than six minutes. Nucleic Acids Research, 2006, vol. 34, No. 11 e77.

Noguchi, et al. Detection of Breast Cancer Micrometastases in Axillary Lymph Nodes by Means of Reverse Transcriptase-Polymerase Chain Reaction. American Journal of Pathology, vol. 148, No. 2, Feb. 1996.

Notomi, et al. Loop-mediated isothermal amplification of DNA. Nucleic Acids Res. Jun. 15, 2000;28(12):E63.

Park, et al. Advances in microfluidic PCR for point-of-care infectious disease diagnostics. Biotechnology advances 29.6 (2011): 830-839.

Parker, et al. Supervised risk predictor of breast cancer based on intrinsic subtypes. J Clin Oncol. Mar. 10, 2009;27(8):1160-7.

PCT/US2016/067381 International Search Report and Written Opinion dated Apr. 3, 2017.

Pearch, et al. Tumour sampling method can significantly influence gene expression profiles derived from neoadjuvant window studies. Sci Rep. 2016; 6: 29434.

Sambrook, et al. Molecular cloning: a laboratory manual, 4th edition (2012).

Sharma, et al. High-Throughput Ultrasonic DNA Shearing for NGS Sample Preparation.

Tan, et al. Quantitative methylation analyses of resection margins predict local recurrences and disease-specific deaths in patients with head and neck squamous cell carcinomas. Br J Cancer. Jul. 22, 2008; 99(2): 357-363.

Tanner et al. Loop-mediated isothermal amplification for detection of nucleic acids. Current Protocols in Molecular Biology 15.14.1-15.14.14, Jan. 2014.

U.S. Appl. No. 15/317,068 Office Action dated Jul. 31, 2019.

U.S. Appl. No. 15/317,068 Restriction Requirement Office Action dated May 14, 2019 (with reference).

Valdes, et al. Intra-operative touch preparation cytology; does it have a role in re-excision lumpectomy? Ann Surg Oncol. Mar. 2007; 14(3) :1045-50.

Vivek, et al. Novel Acoustic-Wave Micromixer device for mixing, solubilization, and isothermal thawing of microplates.

Wang, et al. Distinct molecular mechanisms underlying clinically relevant subtypes of breast cancer: gene expression analyses across three different platforms. BMC Genomics 2006 vol. 7, p. 127.

Wei et al., DNA diagnostics: Nanotechnology-enhanced electrochemical detection of nucleic acids, Pediatric Research (2010) 67, 458-468.

Westin et al. Anchored multiplex amplification on a microelectronic chip array. 2000, Nature Biotechnology, 18, 199-202.

(56) References Cited

OTHER PUBLICATIONS

Wick, MR, MD et al. Diagnostic Histochemistry, Chapter 1: Tissue Procurement, Processing, and Staining Techniques. Aug. 2008; pp. 1-10; ISBN: 9780521874106; figure 1.3, p. 10, paragraph 4; p. 4, paragraph 2, p. 2, paragraph 2.
Witten, et al. Data Mining: Practical Machine Learning Tools and Techniques, 3rd edition (2011).
U.S. Appl. No. 15/317,068 Office Action dated Dec. 9, 2019.
PCT/US2018/039163 International Search Report and Written Opinion dated Nov. 19, 2018.
Zhang, et al. Insights into the distinct roles of MMP-11 in tumor biology and future therapeutics (Review). Int J Oncol. May 2016;48(5):1783-93. doi: 10.3892/ijo.2016.3400. Epub Feb. 18, 2016.
Pedersen, et al. Differential effect of surgical manipulation on gene expression in normal breast tissue and breast tumor tissue. Mol Med. 2018; 24: 57, pp. 1-8.
Pedersen, et al. Supplement—Differential effect of surgical manipulation on gene expression in normal breast tissue and breast tumor tissue. Mol Med. 2018; 24: 57, p. 1.
U.S. Appl. No. 15/317,068 Notice of Allowance dated Feb. 24, 2021.
U.S. Appl. No. 15/317,068 Office Action dated Jun. 23, 2020.
U.S. Serial No. 16/061,517 Office Action dated Mar. 31, 2021.
Bellahcène, A. and V. Castronovo. Expression of bone matrix proteins in human breast cancer: potential roles in microcalcification formation and in the genesis of bone metastases. Bulletin du cancer vol. 84,1 (1997): 17-24.
Co-pending U.S. Application No. 202117328979, inventor Steelman; Brandon, filed on May 24, 2021.
EP18923183 extended European Search Report dated Dec. 20, 2021.
EP20202815 extended European Search Report dated Apr. 23, 2021.
Giussani, Marta et al. Extracellular matrix proteins as diagnostic markers of breast carcinoma. Journal of cellular physiology vol. 233,8 (2018): 6280-6290. doi:10.1002/jcp.26513.
Koga, Takaomi et al. Identification of MGB1 as a marker in the differential diagnosis of lung tumors in patients with a history of breast cancer by analysis of publicly available SAGE data. The Journal of molecular diagnostics: JMD vol. 6,2 (2004): 90-5. doi:10.1016/S1525-1578(10)60495-3.
Krishnamurthy et al. Intraoperative Evaluation of Axillary Sentinel Lymph Nodes in Breast Cancer, Breast Diseases: A Year Book Quarterly, Mosby, ST. Louis, MO, US, vol. 19, No. 3, Jan. 1, 2008 (Jan. 1, 2008), pp. 211-217, XP026032607, ISSN: 1043-321X, Doi: 10.1016/S1043-321X (09)79246-X.
Maitra, A et al. Enrichment of epithelial cells for molecular studies. Nature medicine vol. 5,4 (1999): 459-63. doi:10.1038/7458.
Mangia, Anita et al. Touch imprint cytology in tumor tissue banks for the confirmation of neoplastic cellularity and for DNA extraction. Archives of pathology & laboratory medicine vol. 132,6 (2008): 974-8. doi:10.5858/2008-132-974-TICITT.
Tamiolakis, D. et al. Bilateral metastatic rhabdomyosarcoma to the breast in an adolescent female: touch imprint cytology and implication of MyoD1 nuclear antigen. Onkologie vol. 27,5 (2004): 469-71. doi:10.1159/000080367.
U.S. Appl. No. 16/061,517 Notice of Allowance dated Dec. 3, 2021.
Wang, Yong-sheng et al. GeneSearch™ BLN Assay could replace frozen section and touch imprint cytology for intra-operative assessment of breast sentinel lymph nodes. Breast cancer (Tokyo, Japan) vol. 21,5 (2014): 583-9. doi:10.1007/s12282-012-0437-z.
Tian, Xiuyun et al. Expression of CD147 and matrix metalloproteinase-11 in colorectal cancer and their relationship to clinicopathological features. Journal of translational medicine vol. 13, 337 (2015).

\* cited by examiner

SEQUENCE LISTING

```
<160> NUMBER OF SEQ ID NOS: 359

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cacagggtat acagggttag ctg                                            23

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgaaaaatt tgcatcgaag ag                                             22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcaaaataga ggattctgaa ga                                             22
```

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caatctgtgc cactcactgc                                                   20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
actgccttga gcctgcttc                                                    19

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agaggaggag gaagaagag                                                    19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgagtgagtg agagggcaga                                                   20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agtgagtgag agggcagagg                                                   20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgctttaatt ttgctcagca tt                                                22

<210> SEQ ID NO 10
```

<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgggaatgg cctgtgcttt ctca                                            24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aagcaatcac caaaatgaag ac                                              22

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgaagaaaat ggg                                                        13

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
acagggttag ctgcaatcca                                                 20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtctttaagt acaggccacg at                                              22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
attatcttta caagcatgcc ta                                              22

<210> SEQ ID NO 16
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gagacttcaa atgaaggaga aa                                                 22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
acaatgaaga atcgaatgaa ga                                                 22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgaagactct gaggctgaga at                                                 22

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
accacacttt ctgctacaac ac                                                 22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgggctatgg agaggacgcc ac                                                 22

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
caacactggg ctatggagag g                                                  21

<210> SEQ ID NO 22
<211> LENGTH: 22
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 22
gcctggcaca gggtatacag gg                                        22

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gagtgagagg gcagaggaaa                                           20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
cttttatcct catttaaaac ga                                        22

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ttagctgcaa tccagcttcc caagaag                                   27

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ctcaatctgt gccactcact gc                                        22

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
ctgcttcctc actccaggac                                           20

<210> SEQ ID NO 28
<211> LENGTH: 23
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 28
caagcatgcc tactttttatc ctc                                            23

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cttgagcctg cttcctcact                                                 20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtctttaagt acaggccacg a                                               21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
acaacactgg gctatggaga gg                                              22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gagtgagtga gagggcagag ga                                              22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aatactcaat ctgtgccact ca                                              22

<210> SEQ ID NO 34
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 34
ctgccttgag cctgcttcct ca                                              22

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtgagagggc agaggaaata c                                               21

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctccaggact gccagagg                                                   18

<210> SEQ ID NO 37
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tttccagttc ag                                                         12

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggcagtagtg actcatccga ag                                              22

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtctttaagt acaggccacg a                                               21

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                                 primer

<400> SEQUENCE: 40
aaaatggaga tgacagttca ga                                              22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ttctgcctct gtgctgttgg ta                                              22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctggtgccgt ttatgccttg tt                                              22

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agctttattt gttatatccc cagc                                            24

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gatgcaaatt tttcat                                                     16

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tcctcttctt cttcatcact ttcc                                            24

<210> SEQ ID NO 46
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 46
agaaagcaca ggccattcc                                                    19

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgagaaagca caggccattc cc                                                22

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
attttgactc ttcgatgcaa at                                                22

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggtgccgttt atgccttgtt                                                   20

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cttcttggga agctggattg ca                                                22

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ctgaactgga aatcgtttta aa                                                22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 52
gctaaccctg tataccctgt gc                                              22

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaactgtcat ctccattttc tt                                              22

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
catctccatt ttcttcggat g                                               21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gccgtttatg ccttgttcgt                                                 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gccattccca aaatgctgag                                                 20

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tcctcttcct cctcttcttc tt                                              22

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
```
cagtcttcat tttggtgatt gc                                              22

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cttcatcttc attcgattct tc                                              22

<210> SEQ ID NO 60
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tccccttctt ctccattgtc tc                                              22

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcccagtgtt gtagcagaaa gt                                              22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gcagtcctgg agtgaggaag                                                 20

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
aaaatgctga gcaaaattaa ag                                              22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cgttttcatc cacttctgct tc                                              22

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cagtcctgga gtgaggaagc                                                 20

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gtggtattct cagcctcaga gt                                              22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gctttcttcg ttttcatttc ct                                              22

<210> SEQ ID NO 68
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtacttaaag ac                                                         12

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69 cccatttttct tcagaatcct ct                                             22

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tctccatttt cttcggatga g                                               21

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
attgttttct ccttcatttg aagtctc                                        27

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cttctgcttc gctttcttcg                                                20

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cttctgaact gtcatctcca ttttc                                          25

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
tgtaaagata atatcgtggc ct                                             22

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
tccattttct tcggatgagt c                                              21

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
catcactttc cttctctttt gt                                             22

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agtcctggag tgaggaagca                                                  20

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgaggataaa agtaggcatg ct                                               22

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cggatgagtc actactgcc                                                   19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tcttaccctc tggcagtcct                                                  20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctgagaaagc acaggccatt                                                  20

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctcttcttcc tcctcctctt ct                                               22

```
<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ctccgctgct gccgttgccg tt                                              22

<210> SEQ ID NO 84
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
caggcgtggc gtcctctcca ta                                              22

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
catctccatt ttcttcggat g                                               21

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cgaggcgagc tcttttct                                                   19

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
cctggactat cggggatgac cagg                                            24

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
ataaggggcg gcggcccgga gc                                              22

<210> SEQ ID NO 89
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gcccccaggc tgggatagac ac                                              22

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ttggttcttc caaggtgagg                                                 20

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agggccgtgc tgacatcatg at                                              22

<210> SEQ ID NO 92
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gtactggcat ggggacgacc tg                                              22

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
ccgtttgatg ggcctggggg ca                                              22

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
tacccagcat tggcctctc                                                  19

<210> SEQ ID NO 95
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gtgaggcctc ctttgacgcg gt                                              22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ctgagtctca gcccagatga ct                                              22

<210> SEQ ID NO 97
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
acctccagga ccccagccct gg                                              22

<210> SEQ ID NO 98
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
gctgcagccc ggctacccag ca                                              22

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
taggtgcctg catctgtctg                                                 20

<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gatccttcgg ttcccatggc ag                                              22

<210> SEQ ID NO 101
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 101
tgtggcgcct ccgtgggggc ca                                              22

<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
agacgatggc agaggcccta aa                                              22

<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ctccaccatc cgaggcgagc tc                                              22

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
atccgaggcg agctcttttt                                                 20

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
tcctggccca tgccttcttc cc                                              22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
caatgagatt gcaccgctgg ag                                              22

<210> SEQ ID NO 107
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 107
cagccaaggc cctgatgtcc gc                                              22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gtgaggcctc ctttgacgcg gt                                              22

<210> SEQ ID NO 109
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
cacatttggt tcttccaag                                                  19

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
tgccttcgag gatgcccagg gc                                              22

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cgcgccctcc tgccccgat gc                                               22

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gtttccaccc cagcacc                                                    17

<210> SEQ ID NO 113
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 113
cttctacacc tttcgctacc ca                                              22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gactgcccag ccctgtggac gc                                              22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cggggcggat ggctccggcc gc                                              22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tgctgctgct gctccagccg cc                                              22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gcacagacct gctgcaggtg gc                                              22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tttttcttca aagcgggctt tg                                              22

<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 119
cacatttggt tcttccaag                                                    19

<210> SEQ ID NO 120
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
cgacttcgcc ag                                                           12

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ctgtggacgc tgccttc                                                      17

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ctacccagca ttggcctc                                                     18

<210> SEQ ID NO 123
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ttggcctctc gccactggca gg                                                22

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
tgtggcgcct ccgtgggggc ca                                                22

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 125
tggccagccc tggcccactg tc                                              22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ctcaccttta ctgaggtgca cg                                              22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
caagactcac cgagaagggg at                                              22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
agcccatgaa tttggccacg tg                                              22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tttttcttca aagcgggctt tg                                              22

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggcgagctct ttttcttcaa                                                 20

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 131
ggcccagcaa gcccagcagc cc                                              22

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gtccacttcg actatgatga ga                                              22

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
ccagacgccc cgccagatgc ct                                              22

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gccgctgctg gcccgggctc tgccgccg                                        28

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gactgcccag ccctgtggac gc                                              22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
tgccttcgag gatgcccagg gc                                              22

<210> SEQ ID NO 137
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
```

```
ctacccagca ttggcctctc                                              20

<210> SEQ ID NO 138
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
ctgtggacgc tgccttc                                                 17

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
ccagacgccc cgccagatgc ct                                           22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gctgcagccc ggctacccag ca                                           22

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ttggtgcagg agcaggtgcg gc                                           22

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ggccactgac tggagagg                                                18

<210> SEQ ID NO 143
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
```
ctccaccatc cgaggcgagc tc                                                22

<210> SEQ ID NO 144
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144 gcagggcgt tcaacaccta ta                                                 22

<210> SEQ ID NO 145
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
ctggggctgc agcacacaac ag                                                22

<210> SEQ ID NO 146
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
ggtatggagc gatgtgacgc ca                                                22

<210> SEQ ID NO 147
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
ctggctccgc agcgcggccg cg                                                22

<210> SEQ ID NO 148
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
ttggcctctc gccactggca gg                                                22

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
aggcgagctc tttttcttca                                                   20

<210> SEQ ID NO 150
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gcgagctctt tttcttcaa                                              19

<210> SEQ ID NO 151
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
cttggaagaa ccaaatgtgg cc                                          22

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
cctgcctcgg aagaagtaga                                             20

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ctgtaggtga ggtccgtctt ct                                          22

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gcggacatca gggccttggc tg                                          22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
cgggcacgcc acagcgggga gg                                          22

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 156
cacccctctc cagtcagtg                                            19

<210> SEQ ID NO 157
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 157
catcagcatc ctggaaggca gc                                        22

<210> SEQ ID NO 158
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 158
ccagaccaag gcagcatgga cc                                        22

<210> SEQ ID NO 159
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
ggtggaaacg ccagtagtcc                                           20

<210> SEQ ID NO 160
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
tggcttttca ccgtcgtaca                                           20

<210> SEQ ID NO 161
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
gactggcttt tcaccgtcgt ac                                        22

-continued

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
catctggcgg ggcgtctgg                                                19

<210> SEQ ID NO 163
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
ctgttgtgtg ctgcagcccc ag                                            22

<210> SEQ ID NO 164
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
acatcccctt ctcggtgagt ct                                            22

<210> SEQ ID NO 165
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
ctgggcatcc tcgaaggcag cg                                            22

<210> SEQ ID NO 166
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tagtccctgc ctcggaagaa gt                                            22

<210> SEQ ID NO 167
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
cctggtcatc cccgatagtc ca                                            22

<210> SEQ ID NO 168

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gacagtgggc cagggctggc ca                                              22

<210> SEQ ID NO 169
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ggctgcatgc cagggctgtg gc                                              22

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
ctccagcggt gcaatctcat tg                                              22

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
agaatacccc tccccatttg                                                 20

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gccacctgca gcaggtctgt gc                                              22

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gggtggaaac gccagtagt                                                  19

<210> SEQ ID NO 174
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ggtgctgggg tggaaacgcc ag                                            22

<210> SEQ ID NO 175
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
cccccacgga ggcgccacac aa                                            22

<210> SEQ ID NO 176
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
acccagtact gagcac                                                   16

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gggaacctca ccaggcccag ct                                            22

<210> SEQ ID NO 178
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gactggcttt tcaccgtcgt ac                                            22

<210> SEQ ID NO 179
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gtcgatctca gagggcaccc ct                                            22

<210> SEQ ID NO 180
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 180
ggggcttcct gcgtggcagg gg                                                   22

<210> SEQ ID NO 181
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gatgccccca ggcccatcaa ac                                                   22

<210> SEQ ID NO 182
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
agatcttgtt cttctcggga cc                                                   22

<210> SEQ ID NO 183
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ccaaggtgag gggcctggtg ag                                                   22

<210> SEQ ID NO 184
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
ggtgctgggg tggaaacgcc ag                                                   22

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
cctgaggctg ctggcaggcc gg                                                   22

<210> SEQ ID NO 186
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 186
ggcaggtcgt ccccatgcca gtac                                              24

<210> SEQ ID NO 187
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
agtcatctgg gctgagactc ag                                                22

<210> SEQ ID NO 188
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
agatcttgtt cttctcggga cc                                                22

<210> SEQ ID NO 189
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gaacctcttc tgtcggttgc gg                                                22

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
tgggtagcga aaggtgtaga ag                                                22

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
gactggcttt tcaccgtcgt                                                   20

<210> SEQ ID NO 192
<211> LENGTH: 18
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 192
tacttcttcc gaggcagg                                                     18

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 193
ctcgcctcgg atggtggaga cc                                                22

<210> SEQ ID NO 194
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 194
cggtgagggg tgcggggccc ag                                                22

<210> SEQ ID NO 195
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 195
gcactcagcc catcagatgg gt                                                22

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gtgtctatcc cagcctgggg gc                                                22

<210> SEQ ID NO 197
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
acccagtact gagcac                                                       16

<210> SEQ ID NO 198
<211> LENGTH: 19
<212> TYPE: DNA
<213> ORGANISM: Artificial Sequence
<220> FEATURE:
<223> OTHER INFORMATION: Description of Artificial Sequence: Synthetic

```
                                primer

<400> SEQUENCE: 198
gcgcaggaag taggcatag                                                     19

<210> SEQ ID NO 199
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
gcacgggact gtctacacgc cg                                                 22

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
cggtgagggg tgcggggccc ag                                                 22

<210> SEQ ID NO 201
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
ctacccagca ttggcctc                                                      18

<210> SEQ ID NO 202
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
tgggtagccg ggctgcagct gg                                                 22

<210> SEQ ID NO 203
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
gtcgatctca gagggcaccc ct                                                 22

<210> SEQ ID NO 204
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 204
ctccagtcag tggccctgcg gg                                    22

<210> SEQ ID NO 205
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
cccctcctct cggcatggag gt                                    22

<210> SEQ ID NO 206
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
ctccagtcag tggccctgcg gg                                    22

<210> SEQ ID NO 207
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
gggaacctca ccaggcccag ct                                    22

<210> SEQ ID NO 208
<211> LENGTH: 10
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
ggtgggcgtc                                                  10

<210> SEQ ID NO 209
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
tataggtgtt gaacgcccct gc                                    22

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 210
tagtccctgc ctcggaagaa gt                                            22

<210> SEQ ID NO 211
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gcacgggact gtctacacgc cg                                            22

<210> SEQ ID NO 212
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
ggtctcatca tagtcgaagt gg                                            22

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
gtcaaacttc cagtagaggc g                                             21

<210> SEQ ID NO 214
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
cctcaccttg gaagaaccaa                                               20

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
gccagtggcg agaggccaat gc                                            22

<210> SEQ ID NO 216
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
```
tccacagggc tgggcagtcc ct                                             22

<210> SEQ ID NO 217
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
cacgtggcca aattcatggg ct                                             22

<210> SEQ ID NO 218
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
ccagggctgg ggtcctggag gt                                             22

<210> SEQ ID NO 219
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
caggtgccgg gctactgggc ag                                             22

<210> SEQ ID NO 220
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
agcccgcttt gaagaaaaag ag                                             22

<210> SEQ ID NO 221
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
catcagcatc ctggaaggca gc                                             22

<210> SEQ ID NO 222
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
gcgtcaaagg aggcctcaca gg                                              22

<210> SEQ ID NO 223
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 223
atggaccggg aacctcac                                                   18

<210> SEQ ID NO 224
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
ccagaccaag gcagcatgga cc                                              22

<210> SEQ ID NO 225
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
cccagcgccc gccagaaagc ac                                              22

<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
atggaccggg aacctcac                                                   18

<210> SEQ ID NO 227
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tggggaagaa ggcatgggcc ag                                              22

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
cttctgcact gctcatctgg                                                 20

<210> SEQ ID NO 229
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
agcttcagaa agctgccaag                                               20

<210> SEQ ID NO 230
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gccacaaata ccctttttgc                                               20

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cccaacacca agacacagtt c                                             21

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
tgctgccaca aatacccttt                                               20

<210> SEQ ID NO 233
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
actcccagca cgcag                                                    15

<210> SEQ ID NO 234
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
taccccaccc tacaaaatgc                                               20

<210> SEQ ID NO 235
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ggcagaggaa gcttcagaaa gc                                              22

<210> SEQ ID NO 236
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
acgataccaa atgcccacag                                                 20

<210> SEQ ID NO 237
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
actcccagca cgcag                                                      15

<210> SEQ ID NO 238
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
ggcagaggaa gcttcagaaa                                                 20

<210> SEQ ID NO 239
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tgccaaggca ccatctccag ga                                              22

<210> SEQ ID NO 240
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
ggcagaggaa gcttcagaaa                                                 20

```
<210> SEQ ID NO 241
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
caccttctgc actgctcatc tg                                              22

<210> SEQ ID NO 242
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
ggcagaggaa gcttcagaaa gc                                              22

<210> SEQ ID NO 243
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
agcttcagaa agctgccaag                                                 20

<210> SEQ ID NO 244
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
ggcagaggaa gcttcagaaa                                                 20

<210> SEQ ID NO 245
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
acgataccaa atgcccacag                                                 20

<210> SEQ ID NO 246
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
tgccaaggca ccatctccag ga                                              22

<210> SEQ ID NO 247
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
caccttctgc actgctcatc tg                                              22

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
caaggcacca tctccaggaa                                                 20

<210> SEQ ID NO 249
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
ctttactctt tatggtgtag gg                                              22

<210> SEQ ID NO 250
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
cgttgctgct cacttttcag                                                 20

<210> SEQ ID NO 251
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
gtgggcattt ggtatcgttc                                                 20

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
agcagcaaaa agggtatttg tgg                                             23

<210> SEQ ID NO 253
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
ggacttccgt agcctggttt tc                                              22

<210> SEQ ID NO 254
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
gtaccttgct ctcctcttac tg                                              22

<210> SEQ ID NO 255
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
aatgaagaac tgtgtcttgg tg                                              22

<210> SEQ ID NO 256
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
gtgccctcga ggtccagcag gg                                              22

<210> SEQ ID NO 257
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
atggtcccgg tggtcctggc aa                                              22

<210> SEQ ID NO 258
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
acacctggtt tccctacagc tg                                              22

<210> SEQ ID NO 259
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 259
cagatggatt ctgcgtgct                                                      19

<210> SEQ ID NO 260
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
ttttatgcct gtgggcattt                                                     20

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
ggcagcatat tctcagatgg a                                                   21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
gctctcctct tactgctata c                                                   21

<210> SEQ ID NO 263
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
aagttcaagg atactagcag ca                                                  22

<210> SEQ ID NO 264
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
ttttatgcct gtgggcattt                                                     20

<210> SEQ ID NO 265
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 265
ctggtggtcc agaaggacct gg                                              22

<210> SEQ ID NO 266
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
gtgggcattt ggtatcgttc                                                 20

<210> SEQ ID NO 267
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
aagggtattt gtggcagca                                                  19

<210> SEQ ID NO 268
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
ccctggctct ccttggagtc ca                                              22

<210> SEQ ID NO 269
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
aaaagggtat ttgtggcagc at                                              22

<210> SEQ ID NO 270
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
ttgggtagtg ggcctttat gc                                               22

<210> SEQ ID NO 271
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 271
gtgggcattt ggtatcgttc                                                    20

<210> SEQ ID NO 272
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 272
tggttttcct gggagtcctg gc                                                 22

<210> SEQ ID NO 273
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
gtagcctggt tttcctggtg                                                    20

<210> SEQ ID NO 274
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
agcgtaaaac actccatgaa cc                                                 22

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
tgggcatttg gtatcgttca g                                                  21

<210> SEQ ID NO 276
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
attctcagat ggatt                                                         15

<210> SEQ ID NO 277
<211> LENGTH: 22
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 277
gtaccttgct ctcctcttac tg                                              22

<210> SEQ ID NO 278
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 278
cctggtggac caggagtacc tt                                              22

<210> SEQ ID NO 279
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ctgtgggcat ttggtatcgt tc                                              22

<210> SEQ ID NO 280
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
gcttcccatt caccactagc                                                 20

<210> SEQ ID NO 281
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
tctccactcg aacactgga                                                  19

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
ggccagaacc ctaagatctc c                                               21

<210> SEQ ID NO 283
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
ctggagctca agccactgag                                                  20

<210> SEQ ID NO 284
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 284
aggcttccca ttcaccacta                                                  20

<210> SEQ ID NO 285
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
gtagccattc ctgagccc                                                    18

<210> SEQ ID NO 286
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
ttgtgctgaa ttcggtg                                                     17

<210> SEQ ID NO 287
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
tccactcgaa cactggaaaa                                                  20

<210> SEQ ID NO 288
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
tctccactcg aacactggaa aa                                               22

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 289
tctccactcg aacactggaa                                               20

<210> SEQ ID NO 290
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 290
gcttcaccga attcagcaca                                               20

<210> SEQ ID NO 291
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
caccgaattc agcacaaagg                                               20

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
ccctttactt ctctactggc c                                             21

<210> SEQ ID NO 293
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
ctgagtacgc ttcagcctg                                                19

<210> SEQ ID NO 294
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
ttcagatgaa ggtcaggatt gc                                            22

<210> SEQ ID NO 295
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
```
gaggcttccc attcaccact                          20

<210> SEQ ID NO 296
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 296
tcagatgaag gtcaggattg ct                       22

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tctgtagcca ttcctgagc                           19

<210> SEQ ID NO 298
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
tcagatgaag gtcaggattg ct                       22

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
gcttttctgt caactttctc tgc                      23

<210> SEQ ID NO 300
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
tggaccttgc tatgcagtga                          20

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301

```
ttggcctggt agattcagat g                                          21
```

<210> SEQ ID NO 302
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302

```
ctgtagccat tcctgagccc                                            20
```

<210> SEQ ID NO 303
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303

```
ttcaccgaat tcagcacaaa                                            20
```

<210> SEQ ID NO 304
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304

```
gcttcaccga attcagcaca                                            20
```

<210> SEQ ID NO 305
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305

```
tcaccgaatt cagcacaaag                                            20
```

<210> SEQ ID NO 306
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306

```
tgtacaccat cactgcatag c                                          21
```

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307

```
cccattcacc actagcagga g                                          21
```

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
ttggcctggt agattcagat g                                            21

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
caccgaattc agcacaaagg                                              20

<210> SEQ ID NO 310
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
ctgtagccat tcctgagc                                                18

<210> SEQ ID NO 311
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
gaagcaccgc tcttttttca                                              20

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
tttaccatca cagagaagca c                                            21

<210> SEQ ID NO 313
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
ctgagcctta gtttacca                                                18

```
<210> SEQ ID NO 314
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
gccatagaag ctccattagc ac                                              22

<210> SEQ ID NO 315
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
ccgtctgcat aatgggaaga                                                 20

<210> SEQ ID NO 316
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
atgtagcatt tcaatgagag aa                                              22

<210> SEQ ID NO 317
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
caaaccgtct gcataatggg                                                 20

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
gccaaaagtc tgctgaact                                                  19

<210> SEQ ID NO 319
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
agagaagcac cgctcttttt                                                 20
```

-continued

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
atttcaatga gagaaaggcc aaa                                              23

<210> SEQ ID NO 321
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
tctggtaaat gatgtgaaca ta                                               22

<210> SEQ ID NO 322
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
cagagaagca ccgctctt                                                    18

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ggtgcttctc tgtgatggta a                                                21

<210> SEQ ID NO 324
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
atgtagcatt tcaatgag                                                    18

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
cagagaagca ccgctctttt t                                                21

<210> SEQ ID NO 326

-continued

<210> SEQ ID NO 326
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tgtggctgtg aaggttaacg                                                 20

<210> SEQ ID NO 327
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 327
accgtctgca taatggg                                                    17

<210> SEQ ID NO 328
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 328
accgtctgca taatggga                                                   18

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 329
tttcctaacc cagctccatc                                                 20

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 330
gtgtatccac tctctcaaga t                                               21

<210> SEQ ID NO 331
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 331
caagatcttc cttatgttc                                                  19

<210> SEQ ID NO 332
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 332
accgtctgca taatgggaag                                              20

<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
caagatcttc cttatgttca                                              20

<210> SEQ ID NO 334
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
tatgttcaca tcattta                                                 17

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
tatgttcaca tcatttacc                                               19

<210> SEQ ID NO 336
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
gctgaactgt actgagcctt ag                                           22

<210> SEQ ID NO 337
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
aaccgtctgc ataatgggaa ga                                           22

<210> SEQ ID NO 338
<211> LENGTH: 20
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 338
gaaatcctct tcagtgtatc                                                   20

<210> SEQ ID NO 339
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
ttggtggttt gtatgggt                                                     18

<210> SEQ ID NO 340
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
ggcttgcctc cgaattctat                                                   20

<210> SEQ ID NO 341
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
ggtggtttgt atgggtcaa                                                    19

<210> SEQ ID NO 342
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
ttggtggttt gtatgggtca                                                   20

<210> SEQ ID NO 343
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
gcttgcctcc gaattctatg                                                   20

<210> SEQ ID NO 344
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 344
tggtacgtgc ctcagaacag                                              20

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
aatcctgctc acctttctga g                                            21

<210> SEQ ID NO 346
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
gcttgcctcc gaattctatg                                              20

<210> SEQ ID NO 347
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
tagtcccagg aggtggtacg                                              20

<210> SEQ ID NO 348
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348 aacgttttact agccccacca                                             20

<210> SEQ ID NO 349
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
aggtggtctc tggagggtct                                              20

<210> SEQ ID NO 350
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 350
cctctgcata atccactgtc tg                                              22

<210> SEQ ID NO 351
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 351
aggtggtctc tggagggtct                                                 20

<210> SEQ ID NO 352
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 352
ggtggtctct ggagggtc                                                   18

<210> SEQ ID NO 353
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 353
gccacttggc tcctaacaga                                                 20

<210> SEQ ID NO 354
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 354
agccacttgg ctcctaac                                                   18

<210> SEQ ID NO 355
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 355
ccacttggct cctaacag                                                   18

<210> SEQ ID NO 356
<211> LENGTH: 19
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 356
aacgtttact agccccacc                                                19

<210> SEQ ID NO 357
<211> LENGTH: 2306
<212> TYPE: DNA
<213> ORGANISM: Homo sapiens

<400> SEQUENCE: 357

```
ataaggggcg gcggcccgga gcggcccagc aagcccagca gccccggggc ggatggctcc     60
ggccgcctgg ctccgcagcg cggccgcgcg cgccctcctg cccccgatgc tgctgctgct    120
gctccagccg ccgccgctgc tggcccgggc tctgccgccg acgcccacc acctccatgc    180
cgagaggagg gggccacagc cctggcatgc agccctgccc agtagcccgg cacctgcccc    240
tgccacgcag gaagccccc ggcctgccag cagcctcagg cctccccgct gtggcgtgcc    300
cgacccatct gatgggctga gtgcccgcaa ccgacagaag aggttcgtgc tttctggcgg    360
gcgctgggag aagacggacc tcacctacag gatccttcgg ttcccatggc agttggtgca    420
ggagcaggtg cggcagacga tggcagaggc cctaaaggta tggagcgatg tgacgccact    480
caccttact gaggtgcacg agggccgtgc tgacatcatg atcgacttcg ccaggtactg    540
gcatgggac gacctgccgt ttgatgggcc tggggggcatc ctggcccatg ccttcttccc    600
caagactcac cgagaagggg atgtccactt cgactatgat gagacctgga ctatcgggga    660
tgaccagggc acagacctgc tgcaggtggc agcccatgaa tttggccacg tgctggggct    720
gcagcacaca acagcagcca aggccctgat gtccgccttc tacacctttc gctacccact    780
gagtctcagc ccagatgact gcaggggcgt tcaacaccta tatggccagc cctggcccac    840
tgtcacctcc aggaccccag ccctgggccc caggctggg atagacacca atgagattgc    900
accgctggag ccagacgccc cgccagatgc ctgtgaggcc tcctttgacg cggtctccac    960
catccgaggc gagctctttt tcttcaaagc gggctttgtg tggcgcctcc gtggggggcca   1020
gctgcagccc ggctacccag cattggcctc tcgccactgg caggggactgc ccagccctgt   1080
ggacgctgcc ttcgaggatg cccagggcca catttggttc ttccaaggtg ctcagtactg   1140
ggtgtacgac ggtgaaaaagc cagtcctggg ccccgcaccc ctcaccgagc tgggcctggt   1200
gaggttcccg gtccatgctg ccttggtctg gggtcccgag aagaacaaga tctacttctt   1260
ccgaggcagg gactactggc gtttccaccc cagcacccgg cgtgtagaca gtcccgtgcc   1320
ccgcagggcc actgactgga gagggtgcc ctctgagatc gacgctgcct tccaggatgc   1380
tgatggctat gcctacttcc tgcgcggccg cctctactgg aagtttgacc ctgtgaaggt   1440
gaaggctctg gaaggcttcc cccgtctcgt gggtcctgac ttctttggct gtgccgagcc   1500
tgccaacact ttcctctgac catggcttgg atgccctcag gggtgctgac ccctgccagg   1560
ccacgaatat caggctagag acccatggcc atctttgtgg ctgtgggcac caggcatggg   1620
actgagccca tgtctcctca ggggatgg gtggggtaca accaccatga caactgccgg   1680
gagggccacg caggtcgtgg tcacctgcca gcgactgtct cagactgggc agggaggctt   1740
tggcatgact taagaggaag ggcagtcttg ggcccgctat gcaggtcctg gcaaacctgg   1800
ctgccctgtc tccatccctg tccctcaggg tagcaccatg gcaggactgg gggaactgga   1860
gtgtccttgc tgtatccctg ttgtgaggtt ccttccaggg gctggcactg aagcaagggt   1920
gctggggccc catggccttc agccctggct gagcaactgg gctgtagggc agggccactt   1980
```

```
cctgaggtca ggtcttggta ggtgcctgca tctgtctgcc ttctggctga caatcctgga     2040
aatctgttct ccagaatcca ggccaaaaag ttcacagtca aatggggagg ggtattcttc     2100
atgcaggaga ccccaggccc tggaggctgc aacatacctc aatcctgtcc caggccggat     2160
cctcctgaag ccctttcgc agcactgcta tcctccaaag ccattgtaaa tgtgtgtaca      2220
gtgtgtataa accttcttct tcttttttt ttttaaact gaggattgtc attaaacaca       2280
gttgttttct aaaaaaaaaa aaaaaa                                           2306

<210> SEQ ID NO 358
<211> LENGTH: 1595
<212> TYPE: DNA
<213> ORGANISM: Homo sapiens

<400> SEQUENCE: 358
gagtgagtga gagggcagag gaaatactca atctgtgcca ctcactgcct tgagcctgct      60
tcctcactcc aggactgcca gaggaagcaa tcaccaaaat gaagactgct ttaattttgc     120
tcagcatttt gggaatggcc tgtgcttct caatgaaaaa tttgcatcga agagtcaaaa      180
tagaggattc tgaagaaaat ggggtcttta agtacaggcc acgatattat ctttacaagc     240
atgcctactt ttatcctcat ttaaaacgat ttccagttca gggcagtagt gactcatccg     300
aagaaaatgg agatgacagt tcagaagagg aggaggaaga agaggagact tcaaatgaag     360
gagaaaacaa tgaagaatcg aatgaagatg aagactctga ggctgagaat accacacttt     420
ctgctacaac actgggctat ggagaggacg ccacgcctgg cacagggtat acagggttag     480
ctgcaatcca gcttcccaag aaggctgggg atataacaaa taaagctaca aagagaaagg     540
aaagtgatga agaagaagag gaggaagagg aaggaaatga aaacgaagaa agcgaagcag     600
aagtggatga aaacgaacaa gcataaacg gcaccagtac caacagcaca gaggcagaaa     660
acggcaacgg cagcagcgga ggagacaatg agaagaagg ggaagaagaa agtgtcactg      720
gagccaatgc agaagacacc acagagaccg gaaggcaggg caagggcacc tcgaagacaa     780
caacctctcc aaatggtggg tttgaaccta caaccccacc acaagtctat agaaccactt     840 ccccacctt tgggaaaaacc accaccgttg aatacgaggg ggagtacgaa tacacgggcg     900
ccaatgaata cgacaatgga tatgaaatct atgaaagtga aacggggaa cctcgtgggg     960 acaattaccg agcctatgaa gatgagtaca gctactttaa aggacaaggc tacgatggct    1020
atgatggtca gaattactac caccaccagt gaagctccag cctgggatga attcatccat    1080
tctggctttg catccggcta ccattttcga agttcaactc aggaaggtgc aatataacaa    1140
atgtgcatat tataatgagg aatggtacta ccgttccaga ttttctgtaa ttgcttctgc    1200
aaagtaatag gcttcttgtc cctttttttt ctggcatgtt atggaatgat cattgtaaat    1260
caggaccatt tatcaagcag tacaccaact cataagatca aatttcattg aatggtttga    1320
ggttgtagct ctataaatag tagttttta catgcctgta gtattgctaa ctgcaaaaac    1380
atactctttg tacaagaagt gcttctaaga atttcattga cattaatgac actgtataca    1440
ataaatgtgt agtttcttaa tcgcactacc tatgcaacac tgtgtattag gtttatcatc    1500
ctcatgtatt tttatgtgac ctgtatgtat attctaatct acgagtttta tcacaaataa    1560
aaatgcaatc cttcaaatgt gttataatta aaaaa                                1595

<210> SEQ ID NO 359
<211> LENGTH: 3307
<212> TYPE: RNA
```

<213> ORGANISM: Homo sapiens

<400> SEQUENCE: 359

| | | | | | |
|---|---|---|---|---|---|
| caccuucugc | acugcucauc | ugggcagagg | aagcuucaga | aagcugccaa | ggcaccaucu | 60 |
| ccaggaacuc | ccagcacgca | gaauccaucu | gagaauaugc | ugccacaaau | acccuuuuug | 120 |
| cugcuaguau | ccuugaacuu | gguucaugga | uguuuuacg  | cugaacgaua | ccaaaugccc | 180 |
| acaggcauaa | aaggcccacu | acccaacacc | aagacacagu | ucuucauucc | cuacaccaua | 240 |
| aagaguaaag | guauagcagu | aagaggagag | caagguacuc | cugguccacc | aggcccugcu | 300 |
| ggaccucgag | ggcacccagg | uccuucugga | ccaccaggaa | aaccaggcua | cggaaguccu | 360 |
| ggacuccaag | gagagccagg | guugccagga | ccaccgggac | caucagcugu | agggaaacca | 420 |
| ggugugccag | gacucccagg | aaaaccagga | gagagaggac | cauauggacc | aaaaggagau | 480 |
| guuggaccag | cuggccuacc | aggaccccgg | ggcccaccag | gaccaccugg | aaucccugga | 540 |
| ccggcuggaa | uuucugugcc | aggaaaaaccu | ggacaacagg | gacccacagg | agccccagga | 600 |
| cccaggggcu | uccuggaga  | aaggggugca | ccaggaguce | cugguaugaa | uggacagaaa | 660 |
| ggggaaaugg | gauauggugc | uccuggucgu | ccaggugaga | ggggucuucc | aggcccucag | 720 |
| ggucccacag | gaccaucugg | cccuccugga | gugggaaaaa | gaggugaaaa | uggggucca  | 780 |
| ggacagccag | gcaucaaagg | ugauagaggu | uuccgggag  | aaaugggacc | aauuggccca | 840 |
| ccaggucccc | aaggcccucc | ugggaacga  | gggcagaag  | gcauuggaaa | gccaggagcu | 900 |
| gcuggagccc | caggccagcc | agggauucca | ggaacaaaag | gucucccugg | ggcuccagga | 960 |
| auagcugggc | cccagggcc  | uccugcuuu  | gggaaaccag | gcuugccagg | ccugaaggga | 1020 |
| gaaagaggac | cugcuggccu | uccuggggu  | ccaggugcca | aggggaaca  | agggccagca | 1080 |
| ggucuuccug | ggaagccagg | ucugacugga | ccccugggag | auauggaccc | ccaaggacca | 1140 |
| aaaggcaucc | cgguagcca  | uggucuccca | ggcccuaaag | gugagacagg | gccagcuggg | 1200 |
| ccugcaggau | acccgggc   | uaagggugaa | agggguccc  | cugggucaga | uggaaaacca | 1260 |
| ggguacccag | gaaaaccagg | ucucgauggu | ccuaagggua | acccagggu  | accaggucca | 1320 |
| aaaggugauc | cuggaguugg | aggaccuccu | ggucucccag | gcccugggg  | cccagcagga | 1380 |
| gcaaagggaa | ugcccggaca | caaauggagag | gcuggcccaa | gaggugcccc | uggaauacca | 1440 |
| gguacuagag | gcccuauugg | gccaccaggc | auuccaggau | ucccggguc  | uaaagggau  | 1500 |
| ccaggaaguc | ccggucccuc | uggcccagcu | ggcauagcaa | cuaagggccu | caauggaccc | 1560 |
| accgggccac | cagggccucc | agguccaaga | ggccacucug | gagagccugg | ucuuccaggg | 1620 |
| ccccugggc  | cuccaggccc | accaggucaa | gcagucaugc | cugaggguuu | auaaaggca  | 1680 |
| ggccaaaggc | ccagucuuuc | ugggaccccu | cuuguuagug | ccaaccaggg | gguaacagga | 1740 |
| augccugugu | cugcuuuuac | uguuauucuc | uccaaagcuu | acccagcaau | aggaacuccc | 1800 |
| auaccauuug | auaaaauuuu | guauaacagg | caacagcauu | augacccaag | gacuggaauc | 1860 |
| uuuacuugc  | agauaccagg | aauauacuau | uuucauacc  | acgugcaugu | gaaagggacu | 1920 |
| caugguuggg | uaggccugua | uaagaauggc | accccuguaa | uguacaccua | ugaugaauac | 1980 |
| accaaaggcu | accuggauca | ggcuucaggg | agugccauca | ucgaucucac | agaaaaugac | 2040 |
| caggugugge | uccagcuucc | caaugccgag | ucaaauggcc | uauacccuc  | ugaguauguc | 2100 |
| cacuccucuu | ucucaggauu | ccuaguggcu | ccaaugugag | uacacacaga | gcuaaucaa  | 2160 |
| aucuugugcu | agaaaagca  | uucucuaacu | cuacccacc  | cuacaaaug  | cauuggagg  | 2220 |
| uaggcugaaa | agaauguaau | uuuuauuuc  | ugaaauacag | auuugagcua | ucagaccaac | 2280 |

```
aaaccuuccc ccugaaaagu gagcagcaac guaaaaacgu augugaagcc ucucuugaau    2340
uucuaguuag caaucuuaag gcucuuuaag guuuucucca auauuaaaaa auaucaccaa    2400
agaaguccug cuauguuaaa aacaaacaac aaaaaacaaa caacaaaaaa aaaauuaaaa    2460
aaaaaaacag aaauagagcu cuaaguuaug ugaaauuuga uuugagaaac ucggcauuuc    2520
cuuuuuaaaa aagccuguuu cuaacuauga auaugagaac uucuaggaaa cauccaggag    2580
guaucauaua acuuuguaga acuuaaauac uugaauauuc aaauuuaaaa gacacuguau    2640
ccccuaaaau auuucugaug gugcacuacu cugaggccug uauggcccu uucaucaaua     2700 ucuauucaaa uauacaggug cauauauacu uguuaaagcu cuuauauaaa aaagccccaa    2760
aauauugaag uucaucugaa augcaaggug cuuucaucaa ugaaccuuuu caaacuuuuc    2820
uaugauugca gagaagcuuu uuauauaccc agcauaacuu ggaaacaggu aucugaccua    2880
uucuuauuua guuaacacaa gugugauuaa uuugauuucu uuaauuccuu auugaaucuu    2940
augugauaug auuuucugga uuuacagaac auuagcacau guaccuugug ccucccauuc    3000
aagugaaguu auaauuuaca cugagguuuu caaaauucga cuagaagugg agauauauua    3060
uuuauuuaug cacuguacug uauuuuuaua uugcuguuua aaacuuuuaa gcugugccuc    3120
acuuauuaaa gcacaaaaug uuuuaccuac uccuuauuua cgacgcaaua aaauaacauc    3180
aauagauuuu uaggcugaau uaauuugaaa gcagcaauuu gcuguucuca accauucuuu    3240
caaggcuuuu cauuguucaa aguuaauaaa aaaguaggac aauaaaguga aaaaaaaaaa    3300
aaaaaaa                                                              3307
```

METHODS AND COMPOSITIONS FOR THE ANALYSIS OF CANCER BIOMARKERS

CROSS-REFERENCE TO RELATED APPLICATIONS

This application claims the benefit of U.S. Provisional Application No. 62/523,709, filed Jun. 22, 2017, which is incorporated by reference herein in its entirety.

SEQUENCE LISTING

The instant application contains a Sequence Listing which has been filed electronically in ASCII format and is hereby incorporated by reference in its entirety. Said ASCII copy, created on Jul. 5, 2018, is named 45901_703_201_SL.txt and is 90,970 bytes in size.

BACKGROUND

Molecular tests can detect residual disease after a treatment. The presence of residual disease indicates that the treatment did not completely eliminate a tumor, where treatment may include surgery, radiotherapy, chemotherapy, endocrine therapy, or targeted molecular therapy.

Following surgical treatments, positive surgical margins are defined as tumor cells on the surface of an excised tissue specimen. Since the surface of the excised specimen is topologically equivalent to the wall of the incision, tumor cells on the surface of the incision indicate the presence of residual tumor in a patient after surgical treatment.

Following medical treatments, Pathologic Complete Response (pCR) is defined as the absence of residual tumor in tissue from patients who were previously diagnosed with invasive cancer. pCR is used as a primary endpoint to determine the success of emerging breast cancer treatments in the neoadjuvant setting. Innovative clinical trial designs have validated pathologic complete response (pCR) as a surrogate endpoint, and are now validating pCR as a therapeutic endpoint.

SUMMARY

Described herein are methods and compositions that are useful for an improved RNA-based test suitable for analysis of tumor margins from surgical samples for residual disease, or for analysis of residual disease in post-treatment cancer patients from other samples.

In some aspects, the disclosure provides a method of distinguishing a cancer from adjacent healthy tissue, said method comprising: (a) obtaining a specimen from a human subject, (b) detecting a presence of a set of markers in said specimen by performing an amplification reaction in a plurality of polynucleotides from said specimen, wherein said set of markers is selected from the group consisting essentially of: Matrix Metallopeptidase 11 (MMP11), integrin binding sialoprotein (IBSP), and collagen type X alpha 1 chain (COL10A1); and (c) distinguishing said cancer when a threshold level of said set of markers is detected. In some instances, said plurality of polynucleotides comprise RNA, cDNA, or DNA. In some instances, the detecting comprises using a DNA-intercalating dye or a fluorescent probe, such as a TaqMan probe. In some instances said amplification reaction is a PCR reaction, such as a qPCR reaction or an RTqPCR reaction. In some instances, said method can distinguish said cancer in at least 10 ng of said plurality of polynucleotides from specimen. In some instances, said method can distinguish said cancer in at least 250 cells of said specimen. In some instances, said amplification reaction uses at least one primer sequence that has at least 90% identity to SEQ ID NO: 1-SEQ ID NO: 356, for example to convert RNA into cDNA and/or to amplify a cDNA. In some instances, the specimen is a frozen specimen, a fresh specimen, or a fixed specimen. In some instances, the specimen is a biopsy specimen, such as a liquid biopsy, a solid tissue biopsy, or a surgical excision. In some instances, said specimen is obtained by imprint cytology, with for example a touch-preparation. In some instances said specimen is obtained by scrape preparation, a nipple aspiration, or a ductal lavage. In some instances said cancer is breast cancer, including, but not-limited to, invasive adenocarcinoma, invasive ductal breast cancer, and invasive lobular breast cancer. In some instances, said method distinguishes said breast cancer from adjacent healthy tissue with greater than 90% accuracy, greater than 90% sensitivity, or greater than 90% specificity. In some instances, said method quantitates an amount of said cancer. In some instances said method further comprises outputting a percentage of said plurality of polynucleotides expressing said markers from said specimen. In some instances, the method further comprises comparing said set of markers from said specimen to said set of markers from said control specimen, such as a second specimen from said human subject or a synthetic nucleotide control. In some instances, the method further comprises performing a second assay to distinguish said cancer, such as an immunohistochemistry assay. In some instances, said threshold level of said MMP11 is 1,000 copies per microliter, said threshold level of said IBSP is 25 copies per microliter, and said threshold level of said COL10A1 is 700 copies per microliter. In some instances, said set of markers is selected from the group consisting of: Matrix Metallopeptidase 11 (MMP11), integrin binding sialoprotein (IBSP), and collagen type X alpha 1 chain (COL10A1). In some aspects, said amplification reaction can be a singleplex reaction or a multiplex reaction.

In some aspects, the disclosure provides a kit comprising, at least one primer sequence that has at least 90% identity to any one of SEQ ID NO: 1-SEQ ID NO: 356, and a buffer system. In some instances said buffer system is a PCR buffer system. In some instances, the kits further comprise a DNA-intercalating dye, a fluorescent probe, such as a TaqMan compatible probe. In some instances the kit also comprises a negative control sample, a positive control sample, or a synthetic nucleotide control.

In some aspects, the disclosure provides isolated nucleic acid comprising a primer sequence that has at least 90%, at least 95%, or at least 99% identity to SEQ ID NO: 1-SEQ ID NO: 356.

In some aspects the disclosure provides a method of identifying a biomarker for a cancer comprising: (a) analyzing, by a computer system, a cohort of biomarkers from a population of subjects afflicted with a cancer; (b) applying, by said computer system, a first filter to said cohort of said biomarkers to identify a first subset of biomarkers from said cohort that has at least a 3-fold higher expression level in said cancer as compared to a healthy control biomarker; (c) applying, by said computer system, a second filter to said first subset of biomarkers to identify a second subset of biomarkers that have a false discovery rate for said cancer that is less than 0.000001; and (d) applying, by said computer system, a correlation based filter selection to said second subset of biomarkers to identify the biomarkers that classify the largest number of different types of said cancer. In some aspects, said correlation based filter is an anti-correlation based method. In some aspects, the method further comprises using the identified biomarkers as features input into a machine learning algorithm that distinguishes clinical specimens based on predefined attributes. In some aspects said cancer is breast cancer, including, but not-limited to invasive adenocarcinoma, invasive ductal breast cancer, and invasive lobular breast cancer. In some aspects, said one or more biomarkers identify said cancer with greater than 90% accuracy, greater than 90% sensitivity, or greater than 90% specificity. In some aspects, said one or more biomarkers are therapeutic targets. In some aspects, said false discovery rate is a p-value for said cancer that is less than 0.0000001.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7A panel a depicts amplification plots of 20 microliter qPCR reactions. 12 concentrations of synthetic cDNA template 1.1 million copies per microliter to 0 copies per microliter), including 10-fold dilutions for 6 high concentrations (5 technical replicates) and 2-fold dilutions for 5 low concentrations (7 technical replicates). One concentration point overlapped in the high and low concentration series. Each primer pair includes 24 replicates of no-template controls. Error bars at each cycle represent 95% CI of technical replicates.

FIG. 7A panel b depict fluorescence versus cycle plots to determine Ct for MMP11. A 4-parameter linear model was fitted to 5 technical replicates (circles). The maximum of the second derivative was used to define the Ct (CtD2).

FIG. 7B panel c depicts threshold cycle versus template dilution plots to calculate linear range. The linear range is defined as the range of concentrations where CtD2 fit a straight line with R-squared >0.995. Red lines indicate 95% Confidence Intervals calculated from 200 bootstraps. FIG. 7B panel d depicts melt plots confirm to specificity of the primers. Increasing temperature denatures PCR amplicons, which decreases fluorescence. A single peak of the negative first derivative confirms the presence of a single amplicon. The peak corresponds to the expected melting temperature (dashed line).

FIG. 7A and FIG. 7B panels e-h depict charts showing analytic validation of qPCR assays for IBSP RNA as for MMP11. All assays used clinical-grade reagents. Panel e depicts amplification plots of 20 microliter qPCR reactions. 12 concentrations of synthetic cDNA template (1.1M to 0 copies per microliter), including 10-fold dilutions for 6 high concentrations (5 technical replicates) and 2-fold dilutions for 5 low concentrations (7 technical replicates). One concentration point overlapped in the high and low concentration series. Each primer pair includes 24 replicates of no-template controls. Error bars at each cycle represent 95% Confidence Intervals of technical replicates.

FIG. 7A Panel f depicts fluorescence versus cycle plots to determine Ct for IBSP. A 4-parameter linear model was fitted to 5 technical replicates (circles). The maximum of the second derivative was used to define the Ct (CtD2). FIG. 7B panel g depicts threshold cycle versus template dilution plots to calculate linear range. The linear range is defined as the range of concentrations where CtD2 fit a straight line with R-squared >0.995. Red lines indicate 95% Confidence Intervals calculated from 200 bootstraps.

FIG. 7B panel h depict melt plots that demonstrate the specificity of the primers. Increasing temperature denatures PCR amplicons, which decreases fluorescence. A single peak of the negative first derivative confirms the presence of a single amplicon. The peak corresponds to the expected melting temperature (dashed line).

FIG. 7A and FIG. 7B panels i-l depict analytic validation of qPCR assays for COL10A1 RNA as for MMP11. All assays use clinical-grade reagents. FIG. 7A panel i depict amplification plots of 20 microliter qPCR reactions. 12 concentrations of synthetic cDNA template (1.1M to 0 copies per microliter), including 10-fold dilutions for 6 high concentrations (5 technical replicates) and 2-fold dilutions for 5 low concentrations (7 technical replicates). One concentration point overlapped in the high and low concentration series. Each primer pair included 24 replicates of no-template controls. Error bars at each cycle represent 95% Confidence Intervals of technical replicates. FIG. 7A Panel j depicts fluorescence versus cycle plots to determine Ct for COL10A1. A 4-parameter linear model was used to fit all 5 technical replicates (circles). The maximum of the second derivative (green curve) was used to define the Ct (CtD2). FIG. 7A panel k depicts threshold cycle versus template dilution plots to calculate linear range. The linear range is defined as the range of concentrations where CtD2 fit a straight line with R-squared >0.995. Red lines indicate 95% Confidence Intervals calculated from 200 bootstraps. Panel l depicts melt plots confirm to specificity of the primers. Increasing temperature denatures PCR amplicons, which decreases fluorescence (black line). A single peak of the negative first derivative (red line) confirms the presence of a single amplicon. The peak corresponds to the expected melting temperature (dashed line).

DETAILED DESCRIPTION

I. Overview of Pathologic Complete Response

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

pCR has quickly become the primary endpoint for ~50% of enrolling phase II rectal cancer trials, and 45% of phase III preoperative breast cancer trials. Unpublished results from the I-SPY 2 TRIAL of high-risk breast cancer patients indicate that pCR was statistically associated with 3-year outcomes on pooled patients across all treatment arms. After 3 years, patients who achieved pCR had a 6% recurrence risk (event-free survival), compared to 24% recurrence risk for those who did not achieve pCR.

Improving surrogate endpoints will help to replace treatment regimens with ones that are more effective, less toxic, and that improve survival. However, existing technologies are subjective, qualitative, and underpowered because they are based on visual analysis of a limited number of tissue sections. Moreover, pCR is labor intensive and currently only provided by specialty clinical centers as part of research protocols. Pathology labs routinely examine 3-5 microscopic tissue sections. If therapeutic response is ultimately verified as a therapeutic goal, busy pathology practices will be overwhelmed by requests to examine thousands of sections from hundreds of thousands of U.S. patients with invasive breast cancer. Described herein is a quantitative molecular analysis of residual tumor for identifying improved treatment regimens and complete excision of malignant tissue from patients.

II. Overview of Positive Surgical Margins

Figure 1:
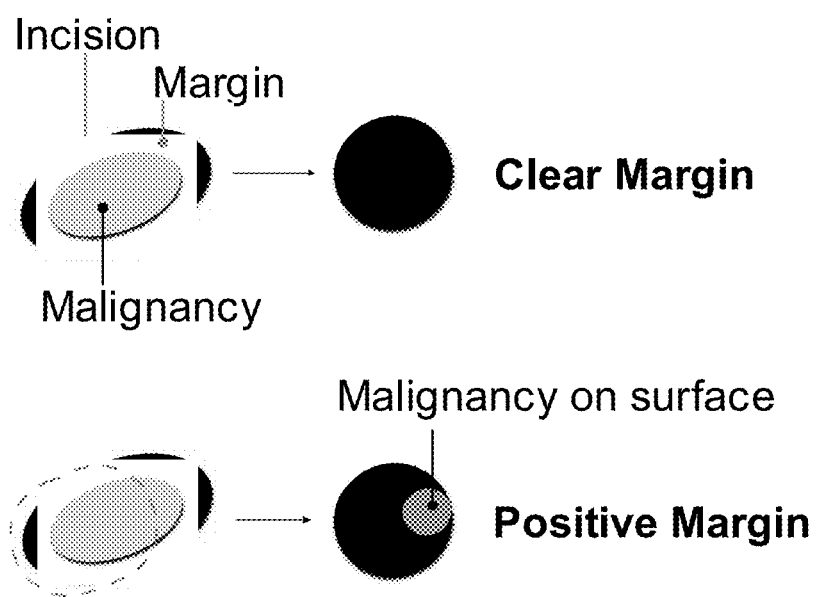
FIG. 1 is a diagram illustrating positive versus clear surgical margins.

Most U.S. breast cancer patients are treated with breast conservation surgery (lumpectomy), where the goal is to remove the entire tumor, bounded by a thin margin of healthy tissue (FIG. 1a). Positive margins are defined as malignant cells that touch the cut surface of a specimen (FIG. 1b), indicating residual tumor in the bed of the incision. Positive margins increase the risk of recurrence and disease-specific mortality. As an example, in a cohort of 1,043 consecutive patients, positive margins were the strongest risk factor of disease-specific mortality among patients with early-stage breast tumors: the 10-year risk of death from breast cancer was 3.9× higher for patients with positive margins, relative to patients with negative margins (95% CI: 1.4-11.5, p=0.011). See, e.g., Meric F, Mirza N Q, Vlastos G, Buchholz T A, Kuerer H M, Babiera G V, Singletary S E, Ross M I, Ames F C, Feig B W, Krishnamurthy S, Perkins G H, McNeese M D, Strom E A, Valero V, Hunt K K. Positive surgical margins and ipsilateral breast tumor recurrence predict disease-specific survival after breast-conserving therapy, Cancer, 2003 Feb. 15; 97(4):926-33.

Patients with positive margins have a higher risk of recurrence (HR: 2.52, 95% CI: 1.04-6.09) than patients with 10 positive lymph nodes (HR: 2.32, 95% CI: 1.29-4.14). These findings hold, even under modern treatment protocols that include localized radiation, endocrine therapy, targeted molecular therapy, and the option of systemic chemotherapy. Detecting and treating positive margins is important because the risk of recurrence typically cannot be mitigated by additional chemotherapy or a radiation boost. Obtaining clear margins is a canon of surgical oncology, and is codified in clinical guidelines (ASCO and NCCN) and consensus statements (SSO and ASRO).

There is a need to improve the evaluation of surgical margins. Histopathology has been the best way to examine tumors for over a century, but it is not an ideal way to hunt for residual disease on the surface of a specimen. A retrospective analysis of 1,201 lumpectomy margins from Harvard's Brigham and Women's Hospital found that when microscopy was used to detect positive margins, it had a 51% sensitivity, 69.5% specificity, 19% false negative rate, and 65% false positive rate. See, e.g., Tang R, Coopey S B, Specht M C, Lei L, Gadd M A, Hughes K S, Brachtel E F, Smith B L. Lumpectomy specimen margins are not reliable in predicting residual disease in breast conserving surgery. Am J Surg. 2015 July; 210(1):93-8. These results were consistent with a prospective, randomized-control trial at Yale, where microscopy of the primary specimen had a false negative rate of 20%. Undersampling is likely to be a primary culprit; microscopic sections only sample a small portion of a specimen's surface. Some pathologists therefore conclude that margin analysis is the weak link in breast cancer care.

Many have tried to reduce reexcisions by testing margins during an operation, but these technologies have failed to reach a clinical impact. This is primarily due to the preliminary nature of rapid intraoperative test results—surgeons use them to predict post-operative test results. Since the relevant reference-standard has a 51% sensitivity and 70% specificity, test discordance has created an insurmountable barrier for adoption—even a perfect intraoperative test cannot predict which margins pathology will call positive. Accordingly, we describe herein a method using nucleic acid tests to improve post-operative testing.

Improved testing has the potential to reduce Type I & II Errors. Type I errors are known as false positives. False positives have proven a significant barrier in the adoption of analysis of tumor margins by microscopy/histology; in a previous study of lumpectomy margin analysis by Tang et al. only 149 (32%) of 462 positive microscopy results actually had residual tumor along the margin. See, e.g., Tang R, Coopey S B, Specht M C, Lei L, Gadd M A, Hughes K S, Brachtel E F, Smith B L. Lumpectomy specimen margins are not reliable in predicting residual disease in breast conserving surgery. Am J Surg. 2015 July; 210(1):93-8.

The 313 false positives triggered an alarming number of unnecessary surgeries. Type II errors are known as false negatives; in the same Tang et al. study, false negatives also presented a problem as traditional microscopy only detected 149 (51%) of the 293 margins that contained residual disease. The 144 patients with false negative results had a high risk of recurrence and mortality, which could have been mitigated by surgical excision. Improving post-operative testing could reduce reexcisions and improve long-term outcomes.

Clinical utility involves a balance between Type I and II errors. The clinical consequence of Type II errors (False Negatives) is that undetected positive margins place patients at high risk of recurrence. Some estimate that microscopy has a Type II error rate of 19% (patients who have positive margins but test negative). Assuming RNA Seq performance is a reasonable indicator of clinical performance, a Type II error rate <5% represents a 75-100% improvement over existing methods. However, exclusive focus on Type II errors would be insufficient; high Type I errors (False Positives) would result in overtreatment. Surgeons may even avoid using a test with high Type I errors (False Positives) because it would trigger unnecessary reexcisions. Some estimates have placed Type I errors (False Positives) as 65% using existing microscopy methods. Reducing Type I errors from 65% to 5% would reduce unnecessary surgical reexcisions >90%.

III. Overview of Ductal Lavage

There is an urgent need to improve breast cancer screening and evaluation. Current screening tests have rates of false negative results, which fail to detect potentially lethal tumors. Current screening tests also have high rates of false positive results, which lead to invasive biopsies in patients who do not have breast cancer. Error rates of existing tests are not uniform. For example, it is not clear from current evidence whether the tradeoff is beneficial for screening mammography in women less than 50 years old. In the U.S., only 0.5% of women who are screened have cancer, but approximately 10% of women who undergo breast cancer screening require additional tests. On a population level, the false positive rate of breast cancer screening is therefore approximately 9.5%.

Mammography is the most widely used screening modality for the detection of breast cancer. There is conflicting evidence about whether screening mammography decreases breast cancer mortality. The evidence is strongest for women aged 50 to 69 years. However, screening in all age groups is also associated with harms. Harms can include unnecessary invasive procedures for patients who do not have breast cancer, and overdiagnosis, which is the detection of tumors that are not clinically significant. The error rates for mammography in women less than 50 are so high relative to the incidence of invasive breast cancers that the benefit of mammography is uncertain for women between 40 to 49 years old. In 2014, the Canadian National Breast Screening Study completed 25 years of follow-up and found no survival benefit associated with screening mammograms for women of all ages. While it is debatable how these findings should be applied to individual patients, it is clear that screening technologies are insufficient.

Alternative imaging technologies sometimes provide benefit for high-risk populations, or as adjuncts to mammography, but are not recommended as primary screening tools for the general population. This group of technologies includes molecular breast imaging, ultrasound, and magnetic resonance imaging.

In the past, patients were advised to perform breast self-exams, but subsequent studies found that breast self-exams have no mortality benefit. Breast exams performed by clinicians (Clinical Breast Exams, CBE) have not been evaluated as an independent screening test. This leaves patients with poor options for early cancer detection, and limited options to determine whether a suspicious screening result warrants an invasive diagnostic procedure.

IV. Overview of a Molecular Test for Complete Response

Described herein is a method for analysis of residual tumor cells. The method and kits disclosed herein can identify improved treatment regimens. Accordingly, disclosed herein are post-operative devices and methods for obtaining and analyzing gene expression from cells from patient samples (e.g. from an excisional surgical biopsy) for residual disease. A panel of one to three cDNAs can serve as biomarkers to distinguish invasive breast cancer from adjacent healthy tissue with an accuracy of 96-100%. When cross-validated on 939 RNA Seq samples, the disclosed 3-gene test had a 96% Accuracy, 96% Sensitivity, and 94% Specificity. On an independent test set of 75 RNA Seq samples, the 3-gene test had a 97% Accuracy, 98% Sensitivity, 96% Specificity, 98% Positive Predictive Value, and 96% Negative Predictive Value. We used The Cancer Genome Atlas (TCGA) project from the National Cancer Institute for biomarker discovery to identify a cohort of biomarkers from a population of subjects afflicted with a cancer. In contrast to many freely available datasets, the Biospecimen Core maintains rigorous protocols and quality controls that increase our confidence in pre-analytical variables. mRNA was profiled by RNA Seq (n=1,218) and microarray (n=132). Subsets from the cohort of biomarkers were identified in subsequent analysis and informed a selection of biomarkers that correctly identified a cancer with high sensitivity and specificity.

V. Overview of a Molecular Test for Positive Surgical Margins mRNAs are promising biomarkers because changes in cell and tissue morphology necessarily involve changes in gene activity and are therefore ideally situated to improve margin analysis. Moreover, we can now catalog tumor mRNAs across the genome. Finally, clinical labs routinely perform sensitive nucleic acid tests, positioning this qPCR assay for rapid adoption.

Prosigna® (PAM50 gene expression test) has 510K clearance from the FDA as a prognostic test for the risk of recurrence, in conjunction with clinical factors. However, by design, half of the 50 mRNAs in PAM50 are expressed at lower levels in tumors than in healthy tissues, and PAM50 is only valid when at least 50% of the sample is tumor. The PAM50 strategy of using genes that are downregulated in tumors could therefore not be used to detect rare tumor cells. Since our clinical indication involves detecting tumor cells in a population of healthy cells, we validated tumor-specific mRNAs with high expression in tumors.

Described herein is a method for analysis of residual tumor cells. The method and kits disclosed herein can identify complete excision of malignant tissue from patients. Accordingly, disclosed herein are post-operative devices and methods for obtaining and analyzing gene expression from cells from patient samples (e.g. on the surface of surgical specimens) for residual disease. Nucleic acid tests for residual tumor cells provide a powerful solution to address positive surgical margins when combined with methods to acquire samples from the surface of a surgical sample.

VI. Overview of Molecular Test for Breast Cancer Screening

Described herein is a method for analysis of rare tumor cells. The method and kits disclosed herein can identify rare cancer cells, even when those tumor cells are not found in the context of healthy tissue. Accordingly, disclosed herein are screening devices and methods for obtaining and analyzing gene expression from cells from patient samples (e.g. nipple aspirates from ductal lavage) for disease. Disclosed herein are also adjuvant devices and methods to determine whether a screening test result warrants further investigation.

VII. Definitions

As used in the specification and in the claims, the singular form "a," "an," and "the" include plural referents unless the context clearly dictates otherwise.

The term "subject" or "patient" can include human or non-human animals. Thus, the methods and described herein are applicable to both human and veterinary disease and animal models. Preferred subjects are "patients," e.g., living humans that are receiving medical care for a disease or condition (e.g., cancer). This includes persons with no defined illness who are being investigated for signs of pathology. The methods described herein are particularly useful for the evaluation of patients having or suspected of having breast adenocarcinomas.

Biomarkers broadly refer to any characteristics that are objectively measured and evaluated as indicators of normal biological processes, pathogenic processes, or pharmacologic responses to therapeutic intervention. Unless otherwise noted, the term biomarker as used herein specifically refers to biomarkers that have biophysical properties, which allow their measurements in biological samples (e.g., plasma, serum, lavage, biopsy). Unless otherwise noted, the term biomarker is used interchangeably with "molecule biomarker" or "molecular markers." Examples of biomarkers include nucleic acid biomarkers (e.g., oligonucleotides or polynucleotides), peptides or protein biomarkers, lipids, and lipopolysaccharide markers.

The term "polynucleotide" or "nucleic acid" as used herein refers to a polymeric form of nucleotides of any length, either ribonucleotides or deoxyribonucleotides, that comprise purine and/or pyrimidine bases, or other naturally modified nucleotide bases. Polynucleotides of the embodiments of the invention include sequences of deoxyribonucleic acid (DNA), ribonucleic acid (RNA), or DNA copies of ribonucleic acid (cDNA), all of which may be isolated from natural sources, recombinantly produced, or artificially synthesized. The polynucleotides and nucleic acids may exist as single-stranded or double-stranded.

The term "primer" as used herein refers to an oligonucleotide which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-35 or more nucleotides, although it may vary for certain biomarkers or applications.

"Biological sample" as used herein is a sample of biological tissue or chemical fluid that is suspected of containing a biomarker or an analyte of interest. The sample may be an ex vivo sample or in vivo sample. Samples include, for example, tissue biopsies, e.g., from the breast or any other tissue suspected to be affected by, for instance, a metastasis of a cancer. The biopsy can be a liquid biopsy or a solid tissue biopsy. The sample can be a surgical excision from a tissue margin or another area suspected to be affected. A sample may be suspended or dissolved in, e.g., buffers, extractants, solvents, and the like. The terms sample and specimen can be used interchangeably herein.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

VIII. Samples

Methods for detecting molecules (e.g., nucleic acids, proteins, etc.) in a subject in order to detect, diagnose, monitor, or evaluate the presence of residual cancer are described in this disclosure. In some cases, the molecules are circulating molecules. In some cases, the molecules are expressed in the cytoplasm of blood, endothelial, or organ cells. In some cases, the molecules are expressed on the surface of blood, endothelial, or organ cells.

The methods, kits, and systems disclosed herein can be used to classify one or more samples from one or more subjects. A sample can be any material containing tissues, cells, nucleic acids, genes, gene fragments, expression products, polypeptides, exosomes, gene expression products, or gene expression product fragments of a subject to be tested. A sample can include but is not limited to, tissue, cells, or biological material from cells or derived from cells of an individual. The sample can be a heterogeneous or homogeneous population of cells or tissues. The sample can be a fluid that is acellular or depleted of cells (e.g., serum). In some cases, the sample is from a single patient. In some cases, the method comprises analyzing multiple samples at once, e.g., via massively parallel multiplex expression analysis on protein arrays or the like.

The sample may be obtained using any suitable method. The sample may be obtained by a minimally-invasive method, e.g., venipuncture or ductal lavage. The sample obtained by venipuncture may comprise whole blood or a component thereof (e.g. serum, white blood cells). Ductal lavage may be performed by e.g. the method described in US20020058887A1, which is incorporated by reference herein. Alternatively, the sample may be obtained an invasive method, such as by biopsy. Biopsies could include core biopsies, punch biopsies, incisional biopsies and excisional biopsies. A sample obtained by surgical excision may comprise a subsection of an excised tissue chunk (e.g. a representative cross-section of tissue). A sample obtained by surgical excision may comprise a cell-dissociated or homogenized chunk of some or all of the excised tissue. A sample obtained by surgical excision may comprise a surface sample of excised tissue. A surface sample of excised tissue may comprise a "touch prep" sample which reflects the population of cells along the margins of the excised tissue (e.g. tumor).

In some embodiments, obtaining a sample comprises directly isolating a sample from a patient. In some embodiments, obtaining a sample comprises obtaining a sample previously isolated from a patient. In some embodiments, obtaining a sample comprises obtaining polynucleotides isolated from a sample previously isolated from a patient.

The cellular specimen may be obtained using imprint cytology acquisition strategies, one form of which is a 'touch prep' or similar method. A 'touch prep' is known as a type of imprint cytology. Generally, the term 'touch prep' refers to both the process of preparing the slide, rapid staining the slide, and analyzing the slide under a microscope. The 'touch prep' method may involve smearing or spreading the obtained cellular specimen onto a slide or a plurality of slides. The 'touch prep' method may involve pressing the slide to the biological sample. The 'touch prep' method may involve pressing the slide to the excised tissue. The 'touch prep' method may involve pressing the slide to a tissue on or within the subject. The 'touch prep' method may involve pressing the slide to an area, wall or margin surrounding a tissue or biological sample on or within the subject. The 'touch prep' method may involve pressing the slide to an area, wall or margin surrounding a site where a tissue was excised. Touch prep may be performed in, e.g. less than about 60 minutes, less than about 55 minutes, less than about 50 minutes, less than about 45 minutes, about less than 40 minutes, about less than 35 minutes, about less than 30 minutes, about less than 25 minutes, less than about 20 minutes, less than about 15 minutes, less than about 10 minutes, less than about 5 minutes, less than about 3 minutes, less than about 2 minutes, less than about 1 minute, less than about 30 seconds, less than about 10 seconds, less than about 5 seconds, less than about 2 seconds, or less than about 1 second. The 'touch prep' method may be performed in a few seconds per slide. The 'touch prep' method may be performed by a surgeon, a nurse, an assistant, a cytopathologist, a person with no medical training or the subject. The 'touch prep' method may be operated manually. The 'touch prep' method may be operated automatically by a machine. The 'touch prep' method may be performed intraoperatively to detect or rule out malignant cells along the surgical margin (e.g. during a breast lumpectomy). During the 'touch prep' method, the excised tissue may be pressed against a sample collection unit which is a glass slide coated with poly-Lysine, or other surface. The cellular specimen obtained by a touch prep method may be used to determine the presence or absence of malignant cells along the margin of excised tissue. In some cases, the surface comprises sample collection unit. In some cases, the sample is then applied to a sample input unit of a device. In some embodiments, the touch prep sample may be obtained according to the methodology described in US20040030263A1, which is incorporated by reference herein.

In some embodiment, the samples comprise tissue samples and are prepared by tumor dissociation/homogenization. In some embodiments, this is accomplished using the Miltenyi Biotec Tumor Dissociation Kit in combination with a gentleMACS Tissue Dissociator to homogenize tissue samples in a sterile environment. The Tissue Dissociator uses disposable Miltenyi M tubes with rotor-stators that are built into the tube lids. Frozen samples may be used to achieve more comsistent yields. Tissue is added to cell lysis in buffer directly in the disruptor tube. After dissociation and lysis, RNA is isolated using an RNA isolation kit, such as Qiagen RNeasy Mini Kit. This method can isolate high-quality RNA from both tumor and adipose-based tissues. Larger specimens may be divided into smaller pieces depending on maximum tissue input. If tissue dissociation alone does not collect enough high-quality RNA for RTqPCR, samples may be pre-incubated with enzymatic treatments (e.g. Collagenases). Enzymatic treatments may be applied during mechanical dissociation, which others have validated for the GentleMACS Tissue Dissociator.

In some embodiments, the methods or compositions herein are capable of detecting breast cancer in a sample from a cancer patient, detecting residual breast cancer in a sample from a cancer patient (e.g. post-chemotherapy/radiation/surgery), or distinguishing between breast cancer and surrounding healthy breast tissue. In some embodiments, the detection is based on a minimal amount of polynucleotides or nucleic acids isolated from a sample.

In some embodiments the minimal amount of polynucleotides or nucleic acids isolated from the sample is at least 10 ng, 50 ng, 100 ng, 200 ng, 500 ng, 1 mg, 2 mg, 3 mg, 4 mg, 5 mg, 10 mg, 15 mg, 20 mg, 50 mg, or 500 ng. In some embodiments, the methods or compositions herein are capable of detecting residual cancer in a sample from a patient, or distinguishing between cancer and surrounding healthy tissue, based on a minimal weight of tissue sample used to isolate polynucleotides or nucleic acids. In some embodiments, the minimal amount of tissue sample is at least 100 ng, 200 ng, 500 ng, 1 mg, 2 mg, 3 mg, 4 mg, 5 mg, 10 mg, 15 mg, 20 mg, 50 mg, 100 mg, 200 mg, 300 mg, or 500 mg.

IX. Biomarkers

The term "biomarker" as used herein refers to a measurable indicator of some biological state or condition. In some instances, a biomarker can be a substance found in a subject, a quantity of the substance, or some other indicator. For example, a biomarker can be the amount of a protein and/or other gene expression products in a sample. In some embodiments, a biomarker is a total level of protein in a sample. In some embodiments, a biomarker is a total level of a particular type of nucleic acid (e.g. RNA, cDNA) in a sample. In some embodiments, a biomarker is a therapeutic target, or an indicator of response to therapy.

The methods, compositions and systems as described here also relate to the use of biomarker panels for purposes of research, identification, diagnosis, classification, treatment or to otherwise characterize the status of cancer in a patient. Sets of biomarkers useful for classifying biological samples are provided, as well as methods of obtaining such sets of biomarkers. Often, the pattern of levels of biomarkers in a panel (also known as a signature) is determined from a control sample or population and then used to evaluate the signature of the same panel of biomarkers in an experimental sample or population, such as by a measure of similarity between the sample signature and the reference signature.

In some embodiments, the panels of biomarkers described herein are useful for the detection of breast cancer (e.g. detection of positive surgical margins on a biopsy sample, detection of residual disease in a cancer patient post-radiation/chemotherapy/surgery, or detection of disease in a patient suspected of having cancer). In some embodiments the breast cancer is invasive adenocarcinoma, invasive ductal breast cancer, invasive lobular breast cancer, or a combination thereof. In some embodiments, the breast cancer is HER2 positive, ER (estrogen receptor) positive, or PR (progesterone receptor) positive, or a combination thereof.

In some embodiments, the breast cancer is HER2 negative, ER (estrogen receptor) negative, or PR (progesterone receptor) negative, or a combination thereof.

In some embodiments, the methods herein comprise measuring expression levels of genes selected from the group consisting essentially of Matrix Metallopeptidase 11 (MMP11), integrin binding sialoprotein (IBSP), and collagen type X alpha 1 chain (COL10A1). In some embodiments, the methods herein comprise measuring expression levels of genes selected from the group consisting of Matrix Metallopeptidase 11 (MMP11), integrin binding sialoprotein (IBSP), and collagen type X alpha 1 chain (COL10A1). In some embodiments the methods herein comprise measuring expression levels of genes selected from the group consisting essentially of Matrix Metallopeptidase 11 (MMP11) and integrin binding sialoprotein (IBSP). In some embodiments the methods herein comprise measuring expression levels of genes selected from the group consisting of Matrix Metallopeptidase 11 (MMP11) and integrin binding sialoprotein (IBSP).

The biomarkers that form the basis for the 3-gene test described herein (MMP11, IBSP, and COL10A1) particularly useful in that their expression is higher (upregulated) in cancerous tissues than in normal tissues. As a result, the fraction of a sample that must contain cancerous cells for the sample to be labeled as positive is much lower than for a test that depends on genes that have decreased expression (downregulated) in cancerous tissue. In some embodiments, the methods, compositions and systems as described here also relate to the use of a biomarker test of research, identification, diagnosis, classification, treatment or to otherwise characterize the status of cancer in a patient, wherein at least one of Matrix Metallopeptidase 11 (MMP11), integrin binding sialoprotein (IBSP), and collagen type X alpha 1 chain (COL10A1) are higher in said cancer than in healthy tissue. In some embodiments, at least two of Matrix Metallopeptidase 11 (MMP11), integrin binding sialoprotein (IBSP), and collagen type X alpha 1 chain (COL10A1) are higher in said cancer than in healthy tissue. In some embodiments, the levels of each of Matrix Metallopeptidase 11 (MMP11), integrin binding sialoprotein (IBSP), and collagen type X alpha 1 chain (COL10A1) are higher in said cancer than in healthy tissue.

X. Biomarker Expression Profiles

The methods, kits, and systems disclosed herein may comprise specifically detecting, profiling, or quantitating biomolecules (e.g., nucleic acids, DNA, RNA, polypeptides, etc.) that are within the biological samples to determine an expression profile. In some instances, genomic expression products, including RNA, or polypeptides, may be isolated from the biological samples. In some cases, nucleic acids, DNA, RNA, polypeptides may be isolated from a cell-free source. In some cases, nucleic acids, DNA, RNA, polypeptides may be isolated from cells derived from the cancer patient. In some cases, the molecules detected are derived from molecules endogenously present in the sample via an enzymatic process (e.g., cDNA derived from reverse transcription of RNA from the biological sample followed by amplification).

Expression profiles are preferably measured at the nucleic acid level, meaning that levels of mRNA or nucleic acid derived therefrom (e.g., cDNA or RNA) are measured. An expression profile refers to the expression levels of a plurality of genes in a sample. A nucleic acid derived from mRNA means a nucleic acid synthesized using mRNA as a template. Methods of isolation and amplification of mRNA are described in, e.g., Chapter 3 of Laboratory Techniques in Biochemistry and Molecular Biology: Hybridization With Nucleic Acid Probes, Part I. Theory and Nucleic Acid Preparation, (P. Tijssen, ed.) Elsevier, N.Y. (1993). If mRNA or a nucleic acid therefrom is amplified, the amplification is performed under conditions that approximately preserve the relative proportions of mRNA in the original samples, such that the levels of the amplified nucleic acids can be used to establish phenotypic associations representative of the mRNAs.

In some embodiments, expression levels are determined by direct detection of nucleic acids. Such methods include e.g. gel or capillary electrophoresis, wherein specifically amplified DNA is detected by its intrinsic fluorescence/absorbance, or by complexing with a suitable absorbent or fluorescent DNA-binding dye. Such methods can be used alongside PCR or RT-PCR with forward and reverse primers against specific genes to detect levels of genes within nucleic acids isolated from a sample.

In other methods, expression levels are determined by Nano String™ assay. Nano String™ based assays are described in the U.S. Pat. Nos. 8,415,102, 8,519,115, and 7,919,237, which are herein incorporated by reference in their entirety. NanoString's NCOUNTER technology is a variation on the DNA microarray. It uses molecular "barcodes" and microscopic imaging to detect and count up to several hundred unique transcripts in one hybridization reaction. Each color-coded barcode is attached to a single target-specific probe corresponding to a target of interest. The protocol typically includes hybridization (employing two ~50 base probes per mRNA that hybridize in solution; the reporter probe carries the signal, while the capture probe allows the complex to be immobilized for data collection); purification and immobilization (after hybridization, the excess probes are removed and the probe/target complexes are aligned and immobilized in the cartridge); and data collection (sample cartridges are placed in a digital analyzer instrument for data collection; color codes on the surface of the cartridge are counted and tabulated for each target molecule). The protocol is carried out with a prep station, which is an automated fluidic instrument that immobilizes code set complexes for data collection, and a digital analyzer, which derives data by counting fluorescent barcodes. Code set complexes are custom-made or pre-designed sets of color-coded probes pre-mixed with a set of system controls. Probes for the barcode-based assay can be designed according to desired variables such as melting temperature (Tm) and specificity for the template mRNA/cDNA to be detected.

In other methods, expression levels are determined by so-called "real time amplification" methods also known as quantitative PCR (qPCR) or Taqman. The basis for this method of monitoring the formation of amplification product formed during a PCR reaction with a template using oligonucleotide probes/oligos specific for a region of the template to be detected. In some embodiments, qPCR or Taqman are used immediately following a reverse-transcriptase reaction performed on isolated cellular mRNA; this variety serves to quantitate the levels of individual mRNAs during qPCR.

Taqman uses a dual-labeled fluorogenic oligonucleotide probe. The dual labeled fluorogenic probe used in such assays is typically a short (ca. 20-25 bases) polynucleotide that is labeled with two different fluorescent dyes. The 5' terminus of the probe is typically attached to a reporter dye and the 3' terminus is attached to a quenching dye. Regardless of labelling or not, the qPCR probe is designed to have at least substantial sequence complementarity with a site on the target mRNA or nucleic acid derived from. Upstream and downstream PCR primers that bind to flanking regions of the locus are also added to the reaction mixture. When the probe is intact, energy transfer between the two fluorophores occurs and the quencher quenches emission from the reporter. During the extension phase of PCR, the probe is cleaved by the 5' nuclease activity of a nucleic acid polymerase such as Taq polymerase, thereby releasing the reporter from the polynucleotide-quencher and resulting in an increase of reporter emission intensity which can be measured by an appropriate detector. The recorded values can then be used to calculate the increase in normalized reporter emission intensity on a continuous basis and ultimately quantify the amount of the mRNA being amplified. mRNA levels can also be measured without amplification by hybridization to a probe, for example, using a branched nucleic acid probe, such as a QuantiGene® Reagent System from Panomics. This format of test is particularly useful for the multiplex detection of multiple genes from a single sample reaction, as each fluorophore/quencher pair attached to an individual probe may be spectrally orthogonal to the other probes used in the reaction such that multiple probes (each directed against a different gene product) can be detected during the amplification/detection reaction.

qPCR can also be performed without a dual-labeled fluorogenic probe by using a fluorescent dye (e.g. SYBR Green) specific for dsDNA that reflects the accumulation of dsDNA amplified specific upstream and downstream oligonucleotide primers. The increase in fluorescence during the amplification reaction is followed on a continuous basis and can be used to quantify the amount of mRNA being amplified.

For qPCR or Taqman, the levels of particular genes may be expressed relative to one or more internal control gene measured from the same sample using the same detection methodology. Internal control genes may include so-called "housekeeping" genes (e.g. ACTB, B2M, UBC, GAPD and HPRT1). In some embodiments, the one or more internal control gene is TTC5, C2orf44, or Chr3.

In some embodiments, for qPCR or Taqman detection, a "pre-amplification" step is performed on cDNA transcribed from cellular RNA prior to the quantitatively monitored PCR reaction. This serves to increase signal in conditions where the natural level of the RNA/cDNA to be detected is very low. Suitable methods for pre-amplification include but are not limited LM-PCR, PCR with random oligonucleotide primers (e.g. random hexamer PCR), PCR with poly-A specific primers, and any combination thereof.

In some embodiments, for qPCR or Taqman detection, an RT-PCR step is first performed to generate cDNA from cellular RNA. Such amplification by RT-PCR can either be general (e.g. amplification with partially/fully degenerate oligonucleotide primers) or targeted (e.g. amplification with oligonucleotide primers directed against specific genes which are to be analyzed at a later step).

In other methods, expression levels are determined by sequencing, such as by RNA sequencing or by DNA sequencing (e.g., of cDNA generated from reverse-transcribing RNA (e.g., mRNA) from a sample). Sequencing may also be general (e.g. with amplification using partially/fully degenerate oligonucleotide primers) or targeted (e.g. with amplification using oligonucleotide primers directed against specific genes which are to be analyzed at a later step). Sequencing may be performed by any available method or technique. Sequencing methods may include: Next Generation sequencing, high-throughput sequencing, pyrosequencing, classic Sanger sequencing methods, sequencing-by-ligation, sequencing by synthesis, sequencing-by-hybridization, RNA-Seq (Illumina), Digital Gene Expression (Helicos), next generation sequencing, single molecule sequencing by synthesis (SMSS) (Helicos), Ion Torrent Sequencing Machine (Life Technologies/Thermo-Fisher), massively-parallel sequencing, clonal single molecule Array (Solexa), shotgun sequencing, Maxim-Gilbert sequencing, primer walking, and any other sequencing methods known in the art.

Measuring gene expression levels may comprise reverse transcribing RNA (e.g., mRNA) within a sample in order to produce cDNA. The cDNA may then be measured using any of the methods described herein (e.g., qPCR, sequencing, etc.).

Alternatively, or additionally, expression levels of genes can be determined at the protein level, meaning that levels of proteins encoded by the genes discussed above are measured. Several methods and devices are well known for determining levels of proteins including immunoassays such as sandwich, competitive, or non-competitive assay formats, to generate a signal that is related to the presence or amount of a protein analyte of interest. Immunoassays such as, but not limited to, lateral flow, enzyme-linked immunoassays (ELISA), radioimmunoassays (RIAs), and competitive binding assays may be utilized. Numerous formats for antibody arrays have been described proposed employing antibodies. Other ligands having specificity for a particular protein target can also be used, such as synthetic antibodies.

XI: Sensitivity, Specificity, Accuracy and Other Measures of Performance

The methods provided herein can detect the presence of residual disease, such as a positive margin on a surgical cancer biopsy or presence of disease (e.g. of in a sample from a cancer patient with a high degree of accuracy, sensitivity, and/or specificity. In some cases, the accuracy (e.g., for detecting residual disease, or distinguishing between residual disease and surrounding healthy tissue) is at least about 75%, 80%, 85%, 90%, 91%, 92%, 93%, 94%, 95%, 96%, 97% 98% or 99%. In some cases, the sensitivity (e.g., for detecting residual disease, or distinguishing between residual disease and surrounding healthy tissue) is at least about 75%, 80%, 85%, 90%, 91%, 92%, 93%, 94%, 95%, 96%, 97% 98% or 99%. In some cases, the specificity (e.g., for detecting residual disease, or distinguishing between residual disease and surrounding healthy tissue) is at least about 75%, 80%, 85%, 90%, 91%, 92%, 93%, 94%, 95%, 96%, 97% 98% or 99%. In some cases, the positive predictive value (e.g., for detecting residual disease, or distinguishing between residual disease and surrounding healthy tissue) of the method at least 75%, 80%, 85%, 90%, 91%, 92%, 93%, 94%, 95%, 96%, 97% 98% or 99%. The AUC after thresholding in any of the methods provided herein may be at least about 0.7, 0.75, 0.8, 0.85, 0.9, 0.91, 0.92, 0.93, 0.94, 0.95. 0.96, 0.97, 0.98, 0.99, 0.995, or 0.999. In some embodiments, the methods disclosed herein have a positive predictive value of at least about 60%, 65%, 70%, 75%, 80%, 85%, 90%, 95%, or 99%. In some embodiments, the methods disclosed herein have a negative predictive value of at least about 60%, 65%, 70%, 75%, 80%, 85%, 90%, 95%, or 99%.

XII. Clinical Applications

The methods, compositions, systems and kits provided herein can be used to detect, diagnose, predict or monitor a condition of a pregnant patient. In some instances, the methods, compositions, systems and kits described herein provide information to a medical practitioner that can be useful in making a therapeutic decision. Therapeutic decisions can include decisions to: continue with a particular therapy, modify a particular therapy, alter the dosage of a particular therapy, stop or terminate a particular therapy, altering the frequency of a therapy, introduce a new therapy, introduce a new therapy to be used in combination with a current therapy, or any combination of the above. In some cases, the methods provided herein can be applied in an experimental setting, e.g., a clinical trial. In some embodiments, the guidance of a test result herein (e.g. presence of residual disease) may be used to determine the end of a course of therapy (e.g. standard chemotherapy regimens). In some embodiments, the guidance of a test result herein (e.g. presence of residual disease) may be used to indicate the location of a further tumor excision to be performed on the patient (e.g. in the case where the test is used in combination with touch prep multiple touch prep samples derived as described above to indicate where surgical margins have been insufficient in an excised sample).

XIII. Monitoring a Condition of a Patient

Provided herein are methods, systems, kits and compositions for monitoring a condition of a cancer patient (e.g. presence of residual disease). Often, the monitoring is conducted by serial testing, such as serial non-invasive tests, serial minimally-invasive tests (e.g., blood draws, ductal lavage), or some combination thereof.

In some instances, the cancer patient is monitored as needed using the methods described herein. Alternatively the cancer patient can be monitored weekly, monthly, or at any pre-specified intervals. In some instances, the cancer patient is monitored at least once every 24 hours. In some instances the cancer patient is monitored at least once every 1 day to 30 days. In some instances the cancer patient is monitored at least once every at least 1 day. In some instances the cancer patient is monitored at least once every at most 30 days. In some instances the cancer patient is monitored at least once every 1 day to 5 days, 1 day to 10 days, 1 day to 15 days, 1 day to 20 days, 1 day to 25 days, 1 day to 30 days, 5 days to 10 days, 5 days to 15 days, 5 days to 20 days, 5 days to 25 days, 5 days to 30 days, 10 days to 15 days, 10 days to 20 days, 10 days to 25 days, 10 days to 30 days, 15 days to 20 days, 15 days to 25 days, 15 days to 30 days, 20 days to 25 days, 20 days to 30 days, or 25 days to 30 days. In some instances the cancer patient is monitored at least once every 1, 2, 3, 4, 5, 6, 7, 8, 9, 10, 11,12, 13, 14, 15, 16, 17, 18, 19, 20, 21, 28, 29, 30 or 31 days. In some instances, the cancer patient is monitored at least once every 1, 2, 3, or 6 months.

XIV. Sequences and Embodiments of Combinations of Sequences

The primers disclosed herein, such as a pair of primers as described herein, specifically a forward primer ("F") and a reverse primer ("R") for both strands to be detected, can be in a composition in amounts effective to permit detection of native, mutant, reference, or control sequences. Detection of native, mutant, reference, or control sequences is accomplished using any of the methods described herein or known by one of ordinary skill in the art in the art for detecting a specific nucleic acid molecule in a sample. The primers disclosed herein may be provided as part of a kit. A kit can also comprise buffers, nucleotide bases and other compositions to be used in hybridization and/or amplification reactions. In other cases, the primers described herein may be part of a device.

In some embodiments a panel of nucleic acids is detected in a sample from a patient. A panel of one to three cDNAs can serve as biomarkers to distinguish invasive breast cancer from adjacent healthy tissue. A panel of one to three cDNAs can serve to residual breast cancer post-chemotherapy, post-radiation treatment, or post-surgical excision of tumor(s). Such cDNA panels may comprise IBSP, MMP11, and/or COL10A1 cDNA. A panel may comprise two or three genes selected from IBSP, MMP11, and COL10A1, which can be amplified using the primers disclosed herein. In some embodiments, the relative levels of cDNA panels may be assessed relative to the cDNA levels of a reference gene panel. Such reference gene panel may comprise TTC5 and/or C2orf44, which can be amplified using the primers disclosed herein. In some cases, the single genes or gene panels are compared to a negative control for genomic DNA, for example, chr3 gDNA, which can be amplified using the primers disclosed herein.

XV. Primers

Exemplary Forward Primers for IBSP cDNA

TABLE 1

| SEQ ID NO: | F primers Ref Code: | Sequence |
|---|---|---|
| SEQ ID NO: 1 | A21 | CACAGGGTATACAGGGTTAGCTG |
| SEQ ID NO: 2 | A27 | ATGAAAAATTTGCATCGAAGAG |
| SEQ ID NO: 3 | A6 | TCAAAATAGAGGATTCTGAAGA |
| SEQ ID NO: 4 | A19 | CAATCTGTGCCACTCACTGC |
| SEQ ID NO: 5 | A32 | ACTGCCTTGAGCCTGCTTC |
| SEQ ID NO: 6 | A30 | AGAGGAGGAGGAAGAAGAG |
| SEQ ID NO: 7 | A12 | TGAGTGAGTGAGAGGGCAGA |
| SEQ ID NO: 8 | A35 | AGTGAGTGAGAGGGCAGAGG |
| SEQ ID NO: 9 | A22 | TGCTTTAATTTTGCTCAGCATT |
| SEQ ID NO: 10 | A23 | TTGGGAATGGCCTGTGCTTTCTCA |
| SEQ ID NO: 11 | A36 | AAGCAATCACCAAAATGAAGAC |
| SEQ ID NO: 12 | A8 | TGAAGAAAATGGG |
| SEQ ID NO: 13 | A16 | ACAGGGTTAGCTGCAATCCA |
| SEQ ID NO: 14 | A5 | GTCTTTAAGTACAGGCCACGAT |
| SEQ ID NO: 15 | A7 | ATTATCTTTACAAGCATGCCTA |
| SEQ ID NO: 16 | A13 | GAGACTTCAAATGAAGGAGAAA |
| SEQ ID NO: 17 | A26 | ACAATGAAGAATCGAATGAAGA |
| SEQ ID NO: 18 | A25 | TGAAGACTCTGAGGCTGAGAAT |
| SEQ ID NO: 19 | A4 | ACCACACTTTCTGCTACAACAC |
| SEQ ID NO: 20 | A20 | TGGGCTATGGAGAGGACGCCAC |
| SEQ ID NO: 21 | A24 | CAACACTGGGCTATGGAGAGG |
| SEQ ID NO: 22 | A1 | GCCTGGCACAGGGTATACAGGG |

TABLE 1-continued

| SEQ ID NO: | F primers Ref Code: | Sequence |
|---|---|---|
| SEQ ID NO: 23 | A17 | GAGTGAGAGGGCAGAGGAAA |
| SEQ ID NO: 24 | A29 | CTTTTATCCTCATTTAAAACGA |
| SEQ ID NO: 25 | A38 | TTAGCTGCAATCCAGCTTCCCAAGAAG |
| SEQ ID NO: 26 | A14 | CTCAATCTGTGCCACTCACTGC |
| SEQ ID NO: 27 | A11 | CTGCTTCCTCACTCCAGGAC |
| SEQ ID NO: 28 | A18 | CAAGCATGCCTACTTTTATCCTC |
| SEQ ID NO: 29 | A37 | CTTGAGCCTGCTTCCTCACT |
| SEQ ID NO: 30 | A39 | GTCTTTAAGTACAGGCCACGA |
| SEQ ID NO: 31 | A9 | ACAACACTGGGCTATGGAGAGG |
| SEQ ID NO: 32 | A10 | GAGTGAGTGAGAGGGCAGAGGA |
| SEQ ID NO: 33 | A40 | AATACTCAATCTGTGCCACTCA |
| SEQ ID NO: 34 | A31 | CTGCCTTGAGCCTGCTTCCTCA |
| SEQ ID NO: 35 | A3 | GTGAGAGGGCAGAGGAAATAC |
| SEQ ID NO: 36 | A28 | CTCCAGGACTGCCAGAGG |
| SEQ ID NO: 37 | A34 | TTTCCAGTTCAG |
| SEQ ID NO: 38 | A15 | GGCAGTAGTGACTCATCCGAAG |
| SEQ ID NO: 39 | A2 | GTCTTTAAGTACAGGCCACGA |
| SEQ ID NO: 40 | A33 | AAAATGGAGATGACAGTTCAGA |

Exemplary Reverse Primers for IBSP cDNA

TABLE 2

| SEQ ID NO: | R primers Ref Code: | Sequence |
|---|---|---|
| SEQ ID NO: 41 | B1 | TTCTGCCTCTGTGCTGTTGGTA |
| SEQ ID NO: 42 | B2 | CTGGTGCCGTTTATGCCTTGTT |
| SEQ ID NO: 43 | B3 | AGCTTTATTTGTTATATCCCCAGC |
| SEQ ID NO: 44 | B4 | GATGCAAATTTTTCAT |
| SEQ ID NO: 45 | B5 | TCCTCTTCTTCTTCATCACTTTCC |
| SEQ ID NO: 46 | B6 | AGAAAGCACAGGCCATTCC |
| SEQ ID NO: 47 | B7 | TGAGAAAGCACAGGCCATTCCC |
| SEQ ID NO: 48 | B8 | ATTTTGACTCTTCGATGCAAAT |
| SEQ ID NO: 49 | B9 | GGTGCCGTTTATGCCTTGTT |
| SEQ ID NO: 50 | B10 | CTTCTTGGGAAGCTGGATTGCA |
| SEQ ID NO: 51 | B11 | CTGAACTGGAAATCGTTTTAAA |
| SEQ ID NO: 52 | B12 | GCTAACCCTGTATACCCTGTGC |
| SEQ ID NO: 53 | B13 | GAACTGTCATCTCCATTTTCTT |
| SEQ ID NO: 54 | B14 | CATCTCCATTTTCTTCGGATG |
| SEQ ID NO: 55 | B15 | GCCGTTTATGCCTTGTTCGT |
| SEQ ID NO: 56 | B16 | GCCATTCCCAAAATGCTGAG |

TABLE 2-continued

| SEQ ID NO: | Ref Code: | R primers Sequence |
|---|---|---|
| SEQ ID NO: 57 | B17 | TCCTCTTCCTCCTCTTCTTCTT |
| SEQ ID NO: 58 | B18 | CAGTCTTCATTTTGGTGATTGC |
| SEQ ID NO: 59 | B19 | CTTCATCTTCATTCGATTCTTC |
| SEQ ID NO: 60 | B20 | TCCCCTTCTTCTCCATTGTCTC |
| SEQ ID NO: 61 | B21 | GCCCAGTGTTGTAGCAGAAAGT |
| SEQ ID NO: 62 | B22 | GCAGTCCTGGAGTGAGGAAG |
| SEQ ID NO: 63 | B23 | AAAATGCTGAGCAAAATTAAAG |
| SEQ ID NO: 64 | B24 | CGTTTTCATCCACTTCTGCTTC |
| SEQ ID NO: 65 | B25 | CAGTCCTGGAGTGAGGAAGC |
| SEQ ID NO: 66 | B26 | GTGGTATTCTCAGCCTCAGAGT |
| SEQ ID NO: 67 | B27 | GCTTTCTTCGTTTTCATTTCCT |
| SEQ ID NO: 68 | B28 | GTACTTAAAGAC |
| SEQ ID NO: 69 | B29 | CCCATTTTCTTCAGAATCCTCT |
| SEQ ID NO: 70 | B30 | TCTCCATTTTCTTCGGATGAG |
| SEQ ID NO: 71 | B31 | ATTGTTTTCTCCTTCATTTGAAGTCTC |
| SEQ ID NO: 72 | B32 | CTTCTGCTTCGCTTTCTTCG |
| SEQ ID NO: 73 | B33 | CTTCTGAACTGTCATCTCCATTTTC |
| SEQ ID NO: 74 | B34 | TGTAAAGATAATATCGTGGCCT |
| SEQ ID NO: 75 | B35 | TCCATTTTCTTCGGATGAGTC |
| SEQ ID NO: 76 | B36 | CATCACTTTCCTTCTCTTTTGT |
| SEQ ID NO: 77 | B37 | AGTCCTGGAGTGAGGAAGCA |
| SEQ ID NO: 78 | B38 | TGAGGATAAAAGTAGGCATGCT |
| SEQ ID NO: 79 | B39 | CGGATGAGTCACTACTGCC |
| SEQ ID NO: 80 | B40 | TCTTACCCTCTGGCAGTCCT |
| SEQ ID NO: 81 | B41 | CTGAGAAAGCACAGGCCATT |
| SEQ ID NO: 82 | B42 | CTCTTCTTCCTCCTCTTCT |
| SEQ ID NO: 83 | B43 | CTCCGCTGCTGCCGTTGCGTT |
| SEQ ID NO: 84 | B44 | CAGGCGTGGCGTCCTCTCCATA |
| SEQ ID NO: 85 | B45 | CATCTCCATTTTCTTCGGATG |

Exemplary Forward Primers for MMP11 cDNA

TABLE 3

| SEQ ID NO: | Ref Code: | F primers Sequence |
|---|---|---|
| SEQ ID NO: 86 | C1 | CGAGGCGAGCTCTTTTTCT |
| SEQ ID NO: 87 | C2 | CCTGGACTATCGGGGATGACCAGG |
| SEQ ID NO: 88 | C3 | ATAAGGGGCGGCGGCCCGGAGC |
| SEQ ID NO: 89 | C4 | GCCCCCAGGCTGGGATAGACAC |
| SEQ ID NO: 90 | C5 | TTGGTTCTTCCAAGGTGAGG |

TABLE 3-continued

| SEQ ID NO: | Ref Code: | F primers Sequence |
|---|---|---|
| SEQ ID NO: 91 | C6 | AGGGCCGTGCTGACATCATGAT |
| SEQ ID NO: 92 | C7 | GTACTGGCATGGGGACGACCTG |
| SEQ ID NO: 93 | C8 | CCGTTTGATGGGCCTGGGGGCA |
| SEQ ID NO: 94 | C9 | TACCCAGCATTGGCCTCTC |
| SEQ ID NO: 95 | C10 | GTGAGGCCTCCTTTGACGCGGT |
| SEQ ID NO: 96 | C11 | CTGAGTCTCAGCCCAGATGACT |
| SEQ ID NO: 97 | C12 | ACCTCCAGGACCCCAGCCCTGG |
| SEQ ID NO: 98 | C13 | GCTGCAGCCCGGCTACCCAGCA |
| SEQ ID NO: 99 | C14 | TAGGTGCCTGCATCTGTCTG |
| SEQ ID NO: 100 | C15 | GATCCTTCGGTTCCCATGGCAG |
| SEQ ID NO: 101 | C16 | TGTGGCGCCTCCGTGGGGGCCA |
| SEQ ID NO: 102 | C17 | AGACGATGGCAGAGGCCCTAAA |
| SEQ ID NO: 103 | C18 | CTCCACCATCCGAGGCGAGCTC |
| SEQ ID NO: 104 | C19 | ATCCGAGGCGAGCTCTTTTT |
| SEQ ID NO: 105 | C20 | TCCTGGCCCATGCCTTCTTCCC |
| SEQ ID NO: 106 | C21 | CAATGAGATTGCACCGCTGGAG |
| SEQ ID NO: 107 | C22 | CAGCCAAGGCCCTGATGTCCGC |
| SEQ ID NO: 108 | C23 | GTGAGGCCTCCTTTGACGCGGT |
| SEQ ID NO: 109 | C24 | CACATTTGGTTCTTCCAAG |
| SEQ ID NO: 110 | C25 | TGCCTTCGAGGATGCCCAGGGC |
| SEQ ID NO: 111 | C26 | CGCGCCCTCCTGCCCCCGATGC |
| SEQ ID NO: 112 | C27 | GTTTCCACCCCAGCACC |
| SEQ ID NO: 113 | C28 | CTTCTACACCTTTCGCTACCCA |
| SEQ ID NO: 114 | C29 | GACTGCCCAGCCCTGTGGACGC |
| SEQ ID NO: 115 | C30 | CGGGGCGGATGGCTCCGGCCGC |
| SEQ ID NO: 116 | C31 | TGCTGCTGCTGCTCCAGCCGCC |
| SEQ ID NO: 117 | C32 | GCACAGACCTGCTGCAGGTGGC |
| SEQ ID NO: 118 | C33 | TTTTTCTTCAAAGCGGGCTTTG |
| SEQ ID NO: 119 | C34 | CACATTTGGTTCTTCCAAG |
| SEQ ID NO: 120 | C35 | CGACTTCGCCAG |
| SEQ ID NO: 121 | C36 | CTGTGGACGCTGCCTTC |
| SEQ ID NO: 122 | C37 | CTACCCAGCATTGGCCTC |
| SEQ ID NO: 123 | C38 | TTGGCCTCTCGCCACTGGCAGG |
| SEQ ID NO: 124 | C39 | TGTGGCGCCTCCGTGGGGGCCA |
| SEQ ID NO: 125 | C40 | TGGCCAGCCCTGGCCCACTGTC |
| SEQ ID NO: 126 | C41 | CTCACCTTTACTGAGGTGCACG |
| SEQ ID NO: 127 | C42 | CAAGACTCACCGAGAAGGGGAT |
| SEQ ID NO: 128 | C43 | AGCCCATGAATTTGGCCACGTG |

TABLE 3-continued

| SEQ ID NO: | F primers Ref Code: | Sequence |
|---|---|---|
| SEQ ID NO: 129 | C44 | TTTTTCTTCAAAGCGGGCTTTG |
| SEQ ID NO: 130 | C45 | GGCGAGCTCTTTTTCTTCAA |
| SEQ ID NO: 131 | C46 | GGCCCAGCAAGCCCAGCAGCCC |
| SEQ ID NO: 132 | C47 | GTCCACTTCGACTATGATGAGA |
| SEQ ID NO: 133 | C48 | CCAGACGCCCCGCCAGATGCCT |
| SEQ ID NO: 134 | C49 | GCCGCTGCTGGCCCGGGCTCTGCCGCCG |
| SEQ ID NO: 135 | C50 | GACTGCCCAGCCCTGTGGACGC |
| SEQ ID NO: 136 | C51 | TGCCTTCGAGGATGCCCAGGGC |
| SEQ ID NO: 137 | C52 | CTACCCAGCATTGGCCTCTC |
| SEQ ID NO: 138 | C53 | CTGTGGACGCTGCCTTC |
| SEQ ID NO: 139 | C54 | CCAGACGCCCCGCCAGATGCCT |
| SEQ ID NO: 140 | C55 | GCTGCAGCCCGGCTACCCAGCA |
| SEQ ID NO: 141 | C56 | TTGGTGCAGGAGCAGGTGCGGC |
| SEQ ID NO: 142 | C57 | GGCCACTGACTGGAGAGG |
| SEQ ID NO: 143 | C58 | CTCCACCATCCGAGGCGAGCTC |
| SEQ ID NO: 144 | C59 | GCAGGGGCGTTCAACACCTATA |
| SEQ ID NO: 145 | C60 | CTGGGGCTGCAGCACACAACAG |
| SEQ ID NO: 146 | C61 | GGTATGGAGCGATGTGACGCCA |
| SEQ ID NO: 147 | C62 | CTGGCTCCGCAGCGCGGCCGCG |
| SEQ ID NO: 148 | C63 | TTGGCCTCTCGCCACTGGCAGG |
| SEQ ID NO: 149 | C64 | AGGCGAGCTCTTTTTCTTCA |
| SEQ ID NO: 150 | C65 | GCGAGCTCTTTTTCTTCAA |

Exemplary Reverse Primers for MMP11 cDNA

TABLE 4

| SEQ ID NO: | R primers Ref Code: | Sequence |
|---|---|---|
| SEQ ID NO: 151 | D1 | CTTGGAAGAACCAAATGTGGCC |
| SEQ ID NO: 152 | D2 | CCTGCCTCGGAAGAAGTAGA |
| SEQ ID NO: 153 | D3 | CTGTAGGTGAGGTCCGTCTTCT |
| SEQ ID NO: 154 | D4 | GCGGACATCAGGGCCTTGGCTG |
| SEQ ID NO: 155 | D5 | CGGGCACGCCACAGCGGGGAGG |
| SEQ ID NO: 156 | D6 | CACCCCTCTCCAGTCAGTG |
| SEQ ID NO: 157 | D7 | CATCAGCATCCTGGAAGGCAGC |
| SEQ ID NO: 158 | D8 | CCAGACCAAGGCAGCATGGACC |
| SEQ ID NO: 159 | D9 | GGTGGAAACGCCAGTAGTCC |
| SEQ ID NO: 160 | D10 | TGGCTTTTCACCGTCGTACA |
| SEQ ID NO: 161 | D11 | GACTGGCTTTTCACCGTCGTAC |
| SEQ ID NO: 162 | D12 | CATCTGGCGGGCGTCTGG |

TABLE 4-continued

| SEQ ID NO: | R primers Ref Code: | Sequence |
|---|---|---|
| SEQ ID NO: 163 | D13 | CTGTTGTGTGCTGCAGCCCCAG |
| SEQ ID NO: 164 | D14 | ACATCCCCTTCTCGGTGAGTCT |
| SEQ ID NO: 165 | D15 | CTGGGCATCCTCGAAGGCAGCG |
| SEQ ID NO: 166 | D16 | TAGTCCCTGCCTCGGAAGAAGT |
| SEQ ID NO: 167 | D17 | CCTGGTCATCCCCGATAGTCCA |
| SEQ ID NO: 168 | D18 | GACAGTGGGCCAGGGCTGGCCA |
| SEQ ID NO: 169 | D19 | GGCTGCATGCCAGGGCTGTGGC |
| SEQ ID NO: 170 | D20 | CTCCAGCGGTGCAATCTCATTG |
| SEQ ID NO: 171 | D21 | AGAATACCCCTCCCCATTTG |
| SEQ ID NO: 172 | D22 | GCCACCTGCAGCAGGTCTGTGC |
| SEQ ID NO: 173 | D23 | GGGTGGAAACGCCAGTAGT |
| SEQ ID NO: 174 | D24 | GGTGCTGGGGTGGAAACGCCAG |
| SEQ ID NO: 175 | D25 | CCCCCACGGAGGCGCCACACAA |
| SEQ ID NO: 176 | D26 | ACCCAGTACTGAGCAC |
| SEQ ID NO: 177 | D27 | GGGAACCTCACCAGGCCCAGCT |
| SEQ ID NO: 178 | D28 | GACTGGCTTTTCACCGTCGTAC |
| SEQ ID NO: 179 | D29 | GTCGATCTCAGAGGGCACCCCT |
| SEQ ID NO: 180 | D30 | GGGGCTTCCTGCGTGGCAGGGG |
| SEQ ID NO: 181 | D31 | GATGCCCCCAGGCCCATCAAAC |
| SEQ ID NO: 182 | D32 | AGATCTTGTTCTTCTCGGGACC |
| SEQ ID NO: 183 | D33 | CCAAGGTGAGGGCCTGGTGAG |
| SEQ ID NO: 184 | D34 | GGTGCTGGGGTGGAAACGCCAG |
| SEQ ID NO: 185 | D35 | CCTGAGGCTGCTGGCAGGCCGG |
| SEQ ID NO: 186 | D36 | GGCAGGTCGTCCCCATGCCAGTAC |
| SEQ ID NO: 187 | D37 | AGTCATCTGGGCTGAGACTCAG |
| SEQ ID NO: 188 | D38 | AGATCTTGTTCTTCTCGGGACC |
| SEQ ID NO: 189 | D39 | GAACCTCTTCTGTCGGTTGCGG |
| SEQ ID NO: 190 | D40 | TGGGTAGCGAAAGGTGTAGAAG |
| SEQ ID NO: 191 | D41 | GACTGGCTTTTCACCGTCGT |
| SEQ ID NO: 192 | D42 | TACTTCTTCCGAGGCAGG |
| SEQ ID NO: 193 | D43 | CTCGCCTCGGATGGTGGAGACC |
| SEQ ID NO: 194 | D44 | CGGTGAGGGGTGCGGGGCCCAG |
| SEQ ID NO: 195 | D45 | GCACTCAGCCCATCAGATGGGT |
| SEQ ID NO: 196 | D46 | GTGTCTATCCCAGCCTGGGGC |
| SEQ ID NO: 197 | D47 | ACCCAGTACTGAGCAC |
| SEQ ID NO: 198 | D48 | GCGCAGGAAGTAGGCATAG |
| SEQ ID NO: 199 | D49 | GCACGGGACTGTCTACACGCCG |
| SEQ ID NO: 200 | D50 | CGGTGAGGGGTGCGGGGCCCAG |

TABLE 4-continued

| SEQ ID NO: | R primers Ref Code: | Sequence |
|---|---|---|
| SEQ ID NO: 201 | D51 | CTACCCAGCATTGGCCTC |
| SEQ ID NO: 202 | D52 | TGGGTAGCCGGGCTGCAGCTGG |
| SEQ ID NO: 203 | D53 | GTCGATCTCAGAGGGCACCCCT |
| SEQ ID NO: 204 | D54 | CTCCAGTCAGTGGCCCTGCGGG |
| SEQ ID NO: 205 | D55 | CCCCTCCTCTCGGCATGGAGGT |
| SEQ ID NO: 206 | D56 | CTCCAGTCAGTGGCCCTGCGGG |
| SEQ ID NO: 207 | D57 | GGGAACCTCACCAGGCCCAGCT |
| SEQ ID NO: 208 | D58 | GGTGGGCGTC |
| SEQ ID NO: 209 | D59 | TATAGGTGTTGAACGCCCCTGC |
| SEQ ID NO: 210 | D60 | TAGTCCCTGCCTCGGAAGAAGT |
| SEQ ID NO: 211 | D61 | GCACGGGACTGTCTACACGCCG |
| SEQ ID NO: 212 | D62 | GGTCTCATCATAGTCGAAGTGG |
| SEQ ID NO: 213 | D63 | GTCAAACTTCCAGTAGAGGCG |
| SEQ ID NO: 214 | D64 | CCTCACCTTGGAAGAACCAA |
| SEQ ID NO: 215 | D65 | GCCAGTGGCGAGAGGCCAATGC |
| SEQ ID NO: 216 | D66 | TCCACAGGGCTGGGCAGTCCCT |
| SEQ ID NO: 217 | D67 | CACGTGGCCAAATTCATGGGCT |
| SEQ ID NO: 218 | D68 | CCAGGGCTGGGGTCCTGGAGGT |
| SEQ ID NO: 219 | D69 | CAGGTGCCGGGCTACTGGGCAG |
| SEQ ID NO: 220 | D70 | AGCCCGCTTTGAAGAAAAAGAG |
| SEQ ID NO: 221 | D71 | CATCAGCATCCTGGAAGGCAGC |
| SEQ ID NO: 222 | D72 | GCGTCAAAGGAGGCCTCACAGG |
| SEQ ID NO: 223 | D73 | ATGGACCGGGAACCTCAC |
| SEQ ID NO: 224 | D74 | CCAGACCAAGGCAGCATGGACC |
| SEQ ID NO: 225 | D75 | CCCAGCGCCCGCCAGAAAGCAC |
| SEQ ID NO: 226 | D76 | ATGGACCGGGAACCTCAC |
| SEQ ID NO: 227 | D77 | TGGGGAAGAAGGCATGGGCCAG |

Exemplary Forward Primers for COL10A1 cDNA

TABLE 5

| SEQ ID NO: | F primers Ref Code: | Sequence |
|---|---|---|
| SEQ ID NO: 228 | E1 | CTTCTGCACTGCTCATCTGG |
| SEQ ID NO: 229 | E2 | AGCTTCAGAAAGCTGCCAAG |
| SEQ ID NO: 230 | E3 | GCCACAAATACCCTTTTGC |
| SEQ ID NO: 231 | E4 | CCCAACACCAAGCACAGTTC |
| SEQ ID NO: 232 | E5 | TGCTGCCACAAATACCCTTT |
| SEQ ID NO: 233 | E6 | ACTCCCAGCACGCAG |
| SEQ ID NO: 234 | E7 | TACCCCACCCTACAAAATGC |

TABLE 5-continued

| SEQ ID NO: | F primers Ref Code: | Sequence |
|---|---|---|
| SEQ ID NO: 235 | E8 | GGCAGAGGAAGCTTCAGAAAGC |
| SEQ ID NO: 236 | E9 | ACGATACCAAATGCCCACAG |
| SEQ ID NO: 237 | E10 | ACTCCCAGCACGCAG |
| SEQ ID NO: 238 | E11 | GGCAGAGGAAGCTTCAGAAA |
| SEQ ID NO: 239 | E12 | TGCCAAGGCACCATCTCCAGGA |
| SEQ ID NO: 240 | E13 | GGCAGAGGAAGCTTCAGAAA |
| SEQ ID NO: 241 | E14 | CACCTTCTGCACTGCTCATCTG |
| SEQ ID NO: 242 | E15 | GGCAGAGGAAGCTTCAGAAAGC |
| SEQ ID NO: 243 | E16 | AGCTTCAGAAAGCTGCCAAG |
| SEQ ID NO: 244 | E17 | GGCAGAGGAAGCTTCAGAAA |
| SEQ ID NO: 245 | E18 | ACGATACCAAATGCCCACAG |
| SEQ ID NO: 246 | E19 | TGCCAAGGCACCATCTCCAGGA |
| SEQ ID NO: 247 | E20 | CACCTTCTGCACTGCTCATCTG |
| SEQ ID NO: 248 | E21 | CAAGGCACCATCTCCAGGAA |

Exemplary Reverse Primers for COL10A1 cDNA

TABLE 6

| SEQ ID NO: | R primers Ref Code: | Sequence |
|---|---|---|
| SEQ ID NO: 249 | F1 | CTTTACTCTTTATGGTGTAGGG |
| SEQ ID NO: 250 | F2 | CGTTGCTGCTCACTTTTCAG |
| SEQ ID NO: 251 | F3 | GTGGGCATTTGGTATCGTTC |
| SEQ ID NO: 252 | F4 | AGCAGCAAAAGGGTATTTGTGG |
| SEQ ID NO: 253 | F5 | GGACTTCCGTAGCCTGGTTTTC |
| SEQ ID NO: 254 | F6 | GTACCTTGCTCTCCTCTTACTG |
| SEQ ID NO: 255 | F7 | AATGAAGAACTGTGTCTTGGTG |
| SEQ ID NO: 256 | F8 | GTGCCCTCGAGGTCCAGCAGGG |
| SEQ ID NO: 257 | F9 | ATGGTCCCGGTGGTCCTGGCAA |
| SEQ ID NO: 258 | F10 | ACACCTGGTTTCCCTACAGCTG |
| SEQ ID NO: 259 | F11 | CAGATGGATTCTGCGTGCT |
| SEQ ID NO: 260 | F12 | TTTTATGCCTGTGGGCATTT |
| SEQ ID NO: 261 | F13 | GGCAGCATATTCTCAGATGGA |
| SEQ ID NO: 262 | F14 | GCTCTCCTCTTACTGCTATAC |
| SEQ ID NO: 263 | F15 | AAGTTCAAGGATACTAGCAGCA |
| SEQ ID NO: 264 | F16 | TTTTATGCCTGTGGGCATTT |
| SEQ ID NO: 265 | F17 | CTGGTGGTCCAGAAGGACCTGG |
| SEQ ID NO: 266 | F18 | GTGGGCATTTGGTATCGTTC |
| SEQ ID NO: 267 | F19 | AAGGGTATTTGTGGCAGCA |
| SEQ ID NO: 268 | F20 | CCCTGGCTCTCCTTGGAGTCCA |

TABLE 6-continued

Exemplary Forward Primers for TTC5 cDNA

| SEQ ID NO: | R primers Ref Code: | Sequence |
|---|---|---|
| SEQ ID NO: 269 | F21 | AAAAGGGTATTTGTGGCAGCAT |
| SEQ ID NO: 270 | F22 | TTGGGTAGTGGGCCTTTTATGC |
| SEQ ID NO: 271 | F23 | GTGGGCATTTGGTATCGTTC |
| SEQ ID NO: 272 | F24 | TGGTTTTCCTGGGAGTCCTGGC |
| SEQ ID NO: 273 | F25 | GTAGCCTGGTTTTCCTGGTG |
| SEQ ID NO: 274 | F26 | AGCGTAAAACACTCCATGAACC |
| SEQ ID NO: 275 | F27 | TGGGCATTTGGTATCGTTCAG |
| SEQ ID NO: 276 | F28 | ATTCTCAGATGGATT |
| SEQ ID NO: 277 | F29 | GTACCTTGCTCTCCTCTTACTG |
| SEQ ID NO: 278 | F30 | CCTGGTGGACCAGGAGTACCTT |
| SEQ ID NO: 279 | F31 | CTGTGGGCATTTGGTATCGTTC |

TABLE 7

Exemplary Reverse Primers for TTC5 cDNA

| SEQ ID NO: | F primers Ref Code: | Sequence |
|---|---|---|
| SEQ ID NO: 280 | G1 | GCTTCCCATTCACCACTAGC |
| SEQ ID NO: 281 | G2 | TCTCCACTCGAACACTGGA |
| SEQ ID NO: 282 | G3 | GGCCAGAACCCTAAGATCTCC |
| SEQ ID NO: 283 | G4 | CTGGAGCTCAAGCCACTGAG |
| SEQ ID NO: 284 | G5 | AGGCTTCCCATTCACCACTA |
| SEQ ID NO: 285 | G6 | GTAGCCATTCCTGAGCCC |
| SEQ ID NO: 286 | G7 | TTGTGCTGAATTCGGTG |
| SEQ ID NO: 287 | G8 | TCCACTCGAACACTGGAAAA |
| SEQ ID NO: 288 | G9 | TCTCCACTCGAACACTGGAAAA |
| SEQ ID NO: 289 | G10 | TCTCCACTCGAACACTGGAA |
| SEQ ID NO: 290 | G11 | GCTTCACCGAATTCAGCACA |
| SEQ ID NO: 291 | G12 | CACCGAATTCAGCACAAAGG |
| SEQ ID NO: 292 | G13 | CCCTTTACTTCTCTACTGGCC |
| SEQ ID NO: 293 | G14 | CTGAGTACGCTTCAGCCTG |

TABLE 8

| SEQ ID NO: | R primers Ref Code: | Sequence |
|---|---|---|
| SEQ ID NO: 294 | H1 | TTCAGATGAAGGTCAGGATTGC |
| SEQ ID NO: 295 | H2 | GAGGCTTCCCATTCACCACT |
| SEQ ID NO: 296 | H3 | TCAGATGAAGGTCAGGATTGCT |
| SEQ ID NO: 297 | H4 | TCTGTAGCCATTCCTGAGC |
| SEQ ID NO: 298 | H5 | TCAGATGAAGGTCAGGATTGCT |

TABLE 8-continued

| SEQ ID NO: | R primers Ref Code: | Sequence |
|---|---|---|
| SEQ ID NO: 299 | H6 | GCTTTTCTGTCAACTTTCTCTGC |
| SEQ ID NO: 300 | H7 | TGGACCTTGCTATGCAGTGA |
| SEQ ID NO: 301 | H8 | TTGGCCTGGTAGATTCAGATG |
| SEQ ID NO: 302 | H9 | CTGTAGCCATTCCTGAGCCC |
| SEQ ID NO: 303 | H10 | TTCACCGAATTCAGCACAAA |
| SEQ ID NO: 304 | H11 | GCTTCACCGAATTCAGCACA |
| SEQ ID NO: 305 | H12 | TCACCGAATTCAGCACAAAG |
| SEQ ID NO: 306 | H13 | TGTACACCATCACTGCATAGC |
| SEQ ID NO: 307 | H14 | CCCATTCACCACTAGCAGGAG |
| SEQ ID NO: 308 | H15 | TTGGCCTGGTAGATTCAGATG |
| SEQ ID NO: 309 | H16 | CACCGAATTCAGCACAAAGG |
| SEQ ID NO: 310 | H17 | CTGTAGCCATTCCTGAGC |

Exemplary Forward Primers for C2orf44 cDNA

TABLE 9

| SEQ ID NO: | F primers Ref Code: | Sequence |
|---|---|---|
| SEQ ID NO: 311 | I1 | GAAGCACCGCTCTTTTTTCA |
| SEQ ID NO: 312 | I2 | TTTACCATCACAGAGAAGCAC |
| SEQ ID NO: 313 | I3 | CTGAGCCTTAGTTTACCA |
| SEQ ID NO: 314 | I4 | GCCATAGAAGCTCCATTAGCAC |
| SEQ ID NO: 315 | I5 | CCGTCTGCATAATGGGAAGA |
| SEQ ID NO: 316 | I6 | ATGTAGCATTTCAATGAGAGAA |
| SEQ ID NO: 317 | I7 | CAAACCGTCTGCATAATGGG |
| SEQ ID NO: 318 | I8 | GCCAAAAGTCTGCTGAACT |
| SEQ ID NO: 319 | I9 | AGAGAAGCACCGCTCTTTTT |
| SEQ ID NO: 320 | I10 | ATTTCAATGAGAGAAAGGCCAAA |
| SEQ ID NO: 321 | I11 | TCTGGTAAATGATGTGAACATA |
| SEQ ID NO: 322 | I12 | CAGAGAAGCACCGCTCTT |
| SEQ ID NO: 323 | I13 | GGTGCTTCTCTGTGATGGTAA |
| SEQ ID NO: 324 | I14 | ATGTAGCATTTCAATGAG |

Exemplary Reverse Primers for C2orf44 cDNA

TABLE 10

| SEQ ID NO: | R primers Ref Code: | Sequence |
|---|---|---|
| SEQ ID NO: 325 | J1 | CAGAGAAGCACCGCTCTTTTT |
| SEQ ID NO: 326 | J2 | TGTGGCTGTGAAGGTTAACG |
| SEQ ID NO: 327 | J3 | ACCGTCTGCATAATGGG |
| SEQ ID NO: 328 | J4 | ACCGTCTGCATAATGGGA |

TABLE 10-continued

| SEQ ID NO: | R primers Ref Code: | Sequence |
|---|---|---|
| SEQ ID NO: 329 | J5 | TTTCCTAACCCAGCTCCATC |
| SEQ ID NO: 330 | J6 | GTGTATCCACTCTCTCAAGAT |
| SEQ ID NO: 331 | J7 | CAAGATCTTCCTTATGTTC |
| SEQ ID NO: 332 | J8 | ACCGTCTGCATAATGGGAAG |
| SEQ ID NO: 333 | J9 | CAAGATCTTCCTTATGTTCA |
| SEQ ID NO: 334 | J10 | TATGTTCACATCATTTA |
| SEQ ID NO: 335 | J11 | TATGTTCACATCATTTACC |
| SEQ ID NO: 336 | J12 | GCTGAACTGTACTGAGCCTTAG |
| SEQ ID NO: 337 | J13 | AACCGTCTGCATAATGGGAAGA |
| SEQ ID NO: 338 | J14 | GAAATCCTCTTCAGTGTATC |

Exemplary Forward Primers for Chr3 gDNA

TABLE 11

| SEQ ID NO: | F primers Ref Code: | Sequence |
|---|---|---|
| SEQ ID NO: 339 | K1 | TTGGTGGTTTGTATGGGT |
| SEQ ID NO: 340 | K2 | GGCTTGCCTCCGAATTCTAT |
| SEQ ID NO: 341 | K3 | GGTGGTTTGTATGGGTCAA |
| SEQ ID NO: 342 | K4 | TTGGTGGTTTGTATGGGTCA |
| SEQ ID NO: 343 | K5 | GCTTGCCTCCGAATTCTATG |
| SEQ ID NO: 344 | K6 | TGGTACGTGCCTCAGAACAG |
| SEQ ID NO: 345 | K7 | AATCCTGCTCACCTTTCTGAG |
| SEQ ID NO: 346 | K8 | GCTTGCCTCCGAATTCTATG |
| SEQ ID NO: 347 | K9 | TAGTCCCAGGAGGTGGTACG |

Exemplary Reverse Primers for Chr3 gDNA

TABLE 12

| SEQ ID NO: | R primers Ref Code: | Sequence |
|---|---|---|
| SEQ ID NO: 348 | L1 | AACGTTTACTAGCCCCACCA |
| SEQ ID NO: 349 | L2 | AGGTGGTCTCTGGAGGGTCT |
| SEQ ID NO: 350 | L3 | CCTCTGCATAATCCACTGTCTG |
| SEQ ID NO: 351 | L4 | AGGTGGTCTCTGGAGGGTCT |
| SEQ ID NO: 352 | L5 | GGTGGTCTCTGGAGGGTC |
| SEQ ID NO: 353 | L6 | GCCACTTGGCTCCTAACAGA |
| SEQ ID NO: 354 | L7 | AGCCACTTGGCTCCTAAC |
| SEQ ID NO: 355 | L8 | CCACTTGGCTCCTAACAG |
| SEQ ID NO: 356 | L9 | AACGTTTACTAGCCCCACC |

XVI. Exemplary Forward/Reverse Primer Combinations for RTqPCR Measurement of IBSP cDNA

TABLE 13

| Combination | IBSP Primer Combinations |
|---|---|
| 1 | A3 + B16 |
| 2 | A18 + B33 |
| 3 | A2 + B45 |
| 4 | A16 + B5 |
| 5 | A24 + B15 |
| 6 | A21 + B32 |
| 7 | A9 + B14 |
| 8 | A24 + B9 |
| 9 | A2 + B30 |
| 10 | A2 + B35 |
| 11 | A19 + B22 |
| 12 | A32 + B25 |
| 13 | A17 + B37 |
| 14 | A12 + B40 |
| 15 | A11 + B41 |
| 16 | A37 + B6 |
| 17 | A39 + B45 |
| 18 | A10 + B7 |
| 19 | A40 + B23 |
| 20 | A31 + B18 |
| 21 | A28 + B18 |
| 22 | A36 + B29 |
| 23 | A22 + B8 |
| 24 | A23 + B4 |
| 25 | A27 + B11 |
| 26 | A6 + B38 |
| 27 | A8 + B34 |
| 28 | A8 + B28 |
| 29 | A5 + B42 |
| 30 | A7 + B13 |
| 31 | A29 + B39 |
| 32 | A34 + B39 |
| 33 | A15 + B10 |
| 34 | A33 + B12 |
| 35 | A30 + B44 |
| 36 | A30 + B21 |
| 37 | A30 + B26 |
| 38 | A30 + B19 |
| 39 | A30 + B31 |
| 40 | A13 + B20 |
| 41 | A26 + B43 |
| 42 | A25 + B1 |
| 43 | A4 + B2 |
| 44 | A20 + B24 |
| 45 | A1 + B27 |
| 46 | A38 + B17 |
| 47 | A38 + B36 |
| 48 | A38 + B3 |

Exemplary Forward/Reverse Primer Combinations for RTqPCR/qPCR Measurement of MMP11 cDNA

TABLE 14

| Combination | MMP11 Primer Combinations |
|---|---|
| 1 | C19 + D10 |
| 2 | C57 + D48 |
| 3 | C14 + D21 |
| 4 | C37 + D41 |
| 5 | C27 + D63 |
| 6 | C36 + D76 |
| 7 | C37 + D76 |
| 8 | C27 + D51 |
| 9 | C53 + D73 |
| 10 | C5 + D23 |
| 11 | C52 + D64 |
| 12 | C9 + D9 |
| 13 | C1 + D2 |
| 14 | C64 + D6 |

TABLE 14-continued

| Combination | MMP11 Primer Combinations |
|---|---|
| 15 | C45 + D33 |
| 16 | C65 + D42 |
| 17 | C3 + D3 |
| 18 | C46 + D75 |
| 19 | C30 + D39 |
| 20 | C62 + D45 |
| 21 | C26 + D5 |
| 22 | C31 + D35 |
| 23 | C49 + D30 |
| 24 | C49 + D69 |
| 25 | C49 + D19 |
| 26 | C49 + D55 |
| 27 | C49 + D58 |
| 28 | C3 + D77 |
| 29 | C46 + D78 |
| 30 | C30 + D79 |
| 31 | C62 + D80 |
| 32 | C26 + D81 |
| 33 | C31 + D82 |
| 34 | C49 + D83 |
| 35 | C15 + D17 |
| 36 | C56 + D62 |
| 37 | C17 + D14 |
| 38 | C61 + D77 |
| 39 | C41 + D31 |
| 40 | C6 + D36 |
| 41 | C35 + D36 |
| 42 | C7 + D20 |
| 43 | C8 + D46 |
| 44 | C20 + D68 |
| 45 | C42 + D18 |
| 46 | C47 + D59 |
| 47 | C2 + D37 |
| 48 | C2 + D40 |
| 49 | C2 + D4 |
| 50 | C2 + D13 |
| 51 | C2 + D67 |
| 52 | C2 + D22 |
| 53 | C32 + D1 |
| 54 | C43 + D15 |
| 55 | C60 + D66 |
| 56 | C22 + D65 |
| 57 | C28 + D52 |
| 58 | C11 + D25 |
| 59 | C59 + D70 |
| 60 | C40 + D43 |
| 61 | C12 + D72 |
| 62 | C4 + D12 |
| 63 | C21 + D12 |
| 64 | C54 + D7 |
| 65 | C23 + D29 |
| 66 | C58 + D54 |
| 67 | C33 + D49 |
| 68 | C39 + D34 |
| 69 | C13 + D60 |
| 70 | C63 + D38 |
| 71 | C50 + D8 |
| 72 | C25 + D57 |
| 73 | C34 + D50 |
| 74 | C34 + D28 |
| 75 | C34 + D26 |
| 76 | C48 + D71 |
| 77 | C10 + D53 |
| 78 | C18 + D56 |
| 79 | C44 + D61 |
| 80 | C16 + D24 |
| 81 | C55 + D16 |
| 82 | C38 + D32 |
| 83 | C29 + D74 |
| 84 | C51 + D27 |
| 85 | C24 + D44 |
| 86 | C66 + D44 |
| 87 | C67 + D44 |

Exemplary Forward/Reverse Primer Combinations for RTqPCR/qPCR Measurement of COL10A1 cDNA

TABLE 15

| Combination | COL10A1 For/Rev Primer Combinations |
|---|---|
| 1 | E21 + F27 |
| 2 | E4 + F25 |
| 3 | E7 + F2 |
| 4 | E18 + F29 |
| 5 | E21 + F4 |
| 6 | E9 + F6 |
| 7 | E3 + F23 |
| 8 | E13 + F11 |
| 9 | E16 + F13 |
| 10 | E5 + F19 |
| 11 | E2 + F16 |
| 12 | E11 + F18 |
| 13 | E17 + F12 |
| 14 | E1 + F3 |
| 15 | E20 + F1 |
| 16 | E8 + F7 |
| 17 | E19 + F22 |
| 18 | E10 + F31 |
| 19 | E10 + F26 |
| 20 | E10 + F15 |
| 21 | E10 + F21 |
| 22 | E10 + F28 |
| 23 | E14 + F24 |
| 24 | E15 + F10 |
| 25 | E12 + F9 |
| 26 | E6 + F20 |
| 27 | E6 + F5 |
| 28 | E6 + F17 |
| 29 | E6 + F8 |
| 30 | E6 + F30 |
| 31 | E6 + F14 |

Exemplary Forward/Reverse Primer Combinations for RTqPCR/qPCR Measurement of TTC5 cDNA

TABLE 16

| Combination | TTC5 Primer Combinations |
|---|---|
| 1 | G11 + H2 |
| 2 | G14 + H13 |
| 3 | G12 + H14 |
| 4 | G3 + H1 |
| 5 | G13 + H6 |
| 6 | G4 + H3 |
| 7 | G3 + H5 |
| 8 | G14 + H11 |
| 9 | G8 + H4 |
| 10 | G10 + H7 |
| 11 | G1 + H12 |
| 12 | G5 + H10 |
| 13 | G9 + H17 |
| 14 | G2 + H9 |
| 15 | G6 + H15 |
| 16 | G7 + H8 |

Exemplary Forward/Reverse Primer Combinations for RTqPCR/qPCR Measurement of C2orf44 cDNA

TABLE 17

| Combination | C2orf44 Primer Combinations |
|---|---|
| 1 | I7 + J12 |
| 2 | I13 + J2 |
| 3 | I5 + J1 |
| 4 | I4 + J5 |
| 5 | I9 + J8 |
| 6 | I12 + J4 |
| 7 | I10 + J3 |
| 8 | I11 + J7 |
| 9 | I14 + J10 |
| 10 | I6 + J11 |
| 11 | I8 + J9 |

TABLE 17-continued

| Combination | C2orf44 Primer Combinations |
|---|---|
| 12 | I2 + J6 |
| 13 | I1 + J13 |
| 14 | I3 + J14 |

Exemplary Forward/Reverse Primer Combinations for RTqPCR/qPCR/RTPCR of Chr3 gDNA

TABLE 18

| Combination | gDNA chr3 Primer Combinations |
|---|---|
| 1 | K7 + L3 |
| 2 | K5 + L2 |
| 3 | K9 + L1 |
| 4 | K4 + L6 |
| 5 | K1 + L7 |
| 6 | K2 + L4 |
| 7 | K3 + L8 |
| 8 | K8 + L5 |
| 9 | K6 + L9 |

In some embodiments, the nucleic acids disclosed herein may be used a biomarker. For example, a portion of the cDNA sequence of MMP11, IBSP, or COL10A1 may be used as a biomarker to detect cancer.

In some embodiments, the sequence of an MMP11 cDNA is according to:

(SEQ ID NO: 357)
ATAAGGGGCGGCGGCCCGGAGCGGCCCAGCAAGCCCAGCAGCCCCGGGGC

GGATGGCTCCGGCCGCCTGGCTCCGCAGCGCGGCCGCGCGCGCCCTCCTG

CCCCCGATGCTGCTGCTGCTGCTCCAGCCGCCGCCGCTGCTGGCCCGGGC

TCTGCCGCCGGACGCCCACCACCTCCATGCCGAGAGGAGGGGCCACAGC

CCTGGCATGCAGCCCTGCCCAGTAGCCCGGCACCTGCCCCTGCCACGCAG

GAAGCCCCCGGCCTGCCAGCAGCCTCAGGCCTCCCCGCTGTGGCGTGCC

CGACCCATCTGATGGGCTGAGTGCCCGCAACCGACAGAAGAGGTTCGTGC

TTTCTGGCGGGCGCTGGGAGAAGACGGACCTCACCTACAGGATCCTTCGG

TTCCCATGGCAGTTGGTGCAGGAGCAGGTGCGGCAGACGATGGCAGAGGC

CCTAAAGGTATGGAGCGATGTGACGCCACTCACCTTTACTGAGGTGCACG

AGGGCCGTGCTGACATCATGATCGACTTCGCCAGGTACTGGCATGGGGAC

GACCTGCCGTTTGATGGGCCTGGGGGCATCCTGGCCCATGCCTTCTTCCC

CAAGACTCACCGAGAAGGGGATGTCCACTTCGACTATGATGAGACCTGGA

CTATCGGGGATGACCAGGGCACAGACCTGCTGCAGGTGGCAGCCCATGAA

TTTGGCCACGTGCTGGGGCTGCAGCACACAACAGCAGCCAAGGCCCTGAT

GTCCGCCTTCTACACCTTTCGCTACCCACTGAGTCTCAGCCCAGATGACT

GCAGGGGCGTTCAACACCTATATGGCCAGCCCTGGCCCACTGTCACCTCC

AGGACCCCAGCCCTGGGCCCCAGGCTGGGATAGACACCAATGAGATTGC

ACCGCTGGAGCCAGACGCCCCGCCAGATGCCTGTGAGGCCTCCTTTGACG

CGGTCTCCACCATCCGAGGCGAGCTCTTTTTCTTCAAAGCGGGCTTTGTG

TGGCGCCTCCGTGGGGGCCAGCTGCAGCCCGGCTACCCAGCATTGGCCTC

TCGCCACTGGCAGGGACTGCCCAGCCCTGTGGACGCTGCCTTCGAGGATG

-continued
CCCAGGGCCACATTTGGTTCTTCCAAGGTGCTCAGTACTGGGTGTACGAC

GGTGAAAAGCCAGTCCTGGGCCCCGCACCCCTCACCGAGCTGGGCCTGGT

GAGGTTCCCGGTCCATGCTGCCTTGGTCTGGGGTCCCGAGAAGAACAAGA

TCTACTTCTTCCGAGGCAGGGACTACTGGCGTTTCCACCCCAGCACCCGG

CGTGTAGACAGTCCCGTGCCCCGCAGGGCCACTGACTGGAGAGGGGTGCC

CTCTGAGATCGACGCTGCCTTCCAGGATGCTGATGGCTATGCCTACTTCC

TGCGCGGCCGCCTCTACTGGAAGTTTGACCCTGTGAAGGTGAAGGCTCTG

GAAGGCTTCCCCCGTCTCGTGGGTCCTGACTTCTTTGGCTGTGCCGAGCC

TGCCAACACTTTCCTCTGACCATGGCTTGGATGCCCTCAGGGGTGCTGAC

CCCTGCCAGGCCACGAATATCAGGCTAGAGACCCATGGCCATCTTTGTGG

CTGTGGGCACCAGGCATGGGACTGAGCCCATGTCTCCTCAGGGGGATGGG

GTGGGGTACAACCACCATGACAACTGCCGGGAGGGCCACGCAGGTCGTGG

TCACCTGCCAGCGACTGTCTCAGACTGGGCAGGGAGGCTTTGGCATGACT

TAAGAGGAAGGGCAGTCTTGGGCCCGCTATGCAGGTCCTGGCAAACCTGG

CTGCCCTGTCTCCATCCCTGTCCCTCAGGGTAGCACCATGGCAGGACTGG

GGGAACTGGAGTGTCCTTGCTGTATCCCTGTTGTGAGGTTCCTTCCAGGG

GCTGGCACTGAAGCAAGGGTGCTGGGGCCCCATGGCCTTCAGCCCTGGCT

GAGCAACTGGGCTGTAGGGCAGGGCCACTTCCTGAGGTCAGGTCTTGGTA

GGTGCCTGCATCTGTCTGCCTTCTGGCTGACAATCCTGGAAATCTGTTCT

CCAGAATCCAGGCCAAAAAGTTCACAGTCAAATGGGGAGGGGTATTCTTC

ATGCAGGAGACCCCAGGCCCTGGAGGCTGCAACATACCTCAATCCTGTCC

CAGGCCGGATCCTCCTGAAGCCCTTTTCGCAGCACTGCTATCCTCCAAAG

CCATTGTAAATGTGTGTACAGTGTGTATAAACCTTCTTCTTCTTTTTTTT

TTTTTAAACTGAGGATTGTCATTAAACACAGTTGTTTTCTAAAAAAAAAA

AAAAAA

In some embodiments, the sequence of an IBSP cDNA is according to:

(SEQ ID NO: 358)
GAGTGAGTGAGAGGGCAGAGGAAATACTCAATCTGTGCCACTCACTGCCT

TGAGCCTGCTTCCTCACTCCAGGACTGCCAGAGGAAGCAATCACCAAAAT

GAAGACTGCTTTAATTTTGCTCAGCATTTTGGGAATGGCCTGTGCTTTCT

CAATGAAAAATTTGCATCGAAGAGTCAAAATAGAGGATTCTGAAGAAAAT

GGGGTCTTTAAGTACAGGCCACGATATTATCTTTACAAGCATGCCTACTT

TTATCCTCATTTAAAACGATTTCCAGTTCAGGGCAGTAGTGACTCATCCG

AAGAAAATGGAGATGACAGTTCAGAAGAGGAGGAGGAAGAAGAGGAGACT

TCAAATGAAGGAGAAAACAATGAAGAATCGAATGAAGATGAAGACTCTGA

GGCTGAGAATACCACACTTTCTGCTACAACACTGGGCTATGGAGAGGACG

CCACGCCTGGCACAGGGTATACAGGGTTAGCTGCAATCCAGCTTCCCAAG

AAGGCTGGGGATATAACAAATAAAGCTACAAAAGAGAAGGAAAGTGATGA

AGAAGAAGAGGAGGAAGAGGAAGGAAATGAAAACGAAGAAAGCGAAGCAG

AAGTGGATGAAAACGAACAAGGCATAAACGGCACCAGTACCAACAGCACA

-continued

GAGGCAGAAAACGGCAACGGCAGCAGCGGAGGAGACAATGGAGAAGAAGG

GGAAGAAGAAAGTGTCACTGGAGCCAATGCAGAAGACACCACAGAGACCG

GAAGGCAGGGCAAGGGCACCTCGAAGACAACAACCTCTCCAAATGGTGGG

TTTGAACCTACAACCCCACCACAAGTCTATAGAACCACTTCCCCACCTTT

TGGGAAAACCACCACCGTTGAATACGAGGGGGAGTACGAATACACGGGCG

CCAATGAATACGACAATGGATATGAAATCTATGAAAGTGAGAACGGGGAA

CCTCGTGGGACAATTACCGAGCCTATGAAGATGAGTACAGCTACTTTAA

AGGACAAGGCTACGATGGCTATGATGGTCAGAATTACTACCACCACCAGT

GAAGCTCCAGCCTGGGATGAATTCATCCATTCTGGCTTTGCATCCGGCTA

CCATTTTCGAAGTTCAACTCAGGAAGGTGCAATATAACAAATGTGCATAT

TATAATGAGGAATGGTACTACCGTTCCAGATTTTCTGTAATTGCTTCTGC

AAAGTAATAGGCTTCTTGTCCCTTTTTTTTCTGGCATGTTATGGAATGAT

CATTGTAAATCAGGACCATTTATCAAGCAGTACACCAACTCATAAGATCA

AATTTCATTGAATGGTTTGAGGTTGTAGCTCTATAAATAGTAGTTTTTAA

CATGCCTGTAGTATTGCTAACTGCAAAAACATACTCTTTGTACAAGAAGT

GCTTCTAAGAATTTCATTGACATTAATGACACTGTATACAATAAATGTGT

AGTTTCTTAATCGCACTACCTATGCAACACTGTGTATTAGGTTTATCATC

CTCATGTATTTTTATGTGACCTGTATGTATATTCTAATCTACGAGTTTTA

TCACAAATAAAAATGCAATCCTTCAAATGTGTTATAATTAAAAAA

In some embodiments, the sequence of a COL10A1 cDNA is according to:

(SEQ ID NO: 359)
CACCUUCUGCACUGCUCAUCUGGGCAGAGGAAGCUUCAGAAAGCUGCCAA

GGCACCAUCUCCAGGAACUCCCAGCACGCAGAAUCCAUCUGAGAAUAUGC

UGCCACAAAUACCCUUUUUGCUGCUAGUAUCCUUGAACUUGGUUCAUGGA

GUGUUUUACGCUGAACGAUACCAAAUGCCCACAGGCAUAAAAGGCCCACU

ACCCAACACCAAGACACAGUUCUUCAUUCCCUACACCAUAAAGAGUAAAG

GUAUAGCAGUAAGAGGAGAGCAAGGUACUCCUGGUCCACCAGGCCCUGCU

GGACCUCGAGGGCACCCAGGUCCUUCUGGACCACCAGGAAAACCAGGCUA

CGGAAGUCCUGGACUCCAAGGAGAGCCAGGGUUGCCAGGACCACCGGGAC

CAUCAGCUGUAGGGAAACCAGGUGUGCCAGGACUCCCAGGAAAACCAGGA

GAGAGAGGACCAUAUGGACCAAAAGGAGAUGUUGGACCAGCUGGCCUACC

AGGACCCCGGGCCCACCAGGACCACCUGGAAUCCCUGGACCGGCUGGAA

UUUCUGUGCCAGGAAAACCUGGACAACAGGGACCCACAGGAGCCCCAGGA

CCCAGGGGCUUUCCUGGAGAAAAGGGUGCACCAGGAGUCCCUGGUAUGAA

UGGACAGAAAGGGGAAAUGGGAUAUGGUGCUCCUGGUCGUCCAGGUGAGA

GGGGUCUUCCAGGCCCUCAGGGUCCCACAGGACCAUCUGGCCCUCCUGGA

GUGGGAAAAAGAGGUGAAAAUGGGGUUCCAGGACAGCCAGGCAUCAAGG

UGAUAGAGGUUUUCCGGGAGAAAUGGGACCAAUUGGCCCACCAGGUCCCC

AAGGCCCUCCUGGGGAACGAGGGCCAGAAGGCAUUGGAAAGCCAGGAGCU

-continued

GCUGGAGCCCCAGGCCAGCCAGGGAUUCCAGGAACAAAAGGUCUCCCUGG

GGCUCCAGGAAUAGCUGGGCCCCCAGGGCCUCCUGGCUUUGGGAAACCAG

GCUUGCCAGGCCUGAAGGGAGAAAGAGGACCUGCUGGCCUUCCUGGGGGU

CCAGGUGCCAAAGGGGAACAAGGGCCAGCAGGUCUUCCUGGGAAGCCAGG

UCUGACUGGACCCCCUGGGAAUAUGGGACCCCAAGGACCAAAAGGCAUCC

CGGGUAGCCAUGGUCUCCCCAGGCCCUAAAGGUGAGACAGGGCCAGCUGGG

CCUGCAGGAUACCCUGGGGCUAAGGGUGAAAGGGGUUCCCCUGGGUCAGA

UGGAAAACCAGGGUACCCAGGAAAACCAGGUCUCGAUGGUCCUAAGGGUA

ACCCAGGGUUACCAGGUCCAAAAGGUGAUCCUGGAGUUGGAGGACCUCCU

GGUCUCCCAGGCCCUGUGGGCCCAGCAGGAGCAAAGGGAAUGCCCGGACA

CAAUGGAGAGGCUGGCCCCAAGAGGUGCCCCUGGAAUACCAGGUACUAGAG

GCCCUAUUGGGCCACCAGGCAUUCCAGGAUUCCCUGGGUCUAAAGGGGAU

CCAGGAAGUCCCGGUCCUCCUGGCCCAGCUGGCAUAGCAACUAAGGGCCU

CAAUGGACCCACCGGGCCACCAGGGCCUCCAGGUCCAAGAGGCCACUCUG

GAGAGCCUGGUCUUCCAGGGCCCCCUGGGCCUCCAGGCCCACCAGGUCAA

GCAGUCAUGCCUGAGGGUUUUAUAAAGGCAGGCCAAAGGCCCAGUCUUUC

UGGGACCCCUCUUGUUAGUGCCAACCAGGGGGUAACAGGAAUGCCUGUGU

CUGCUUUUACUGUUAUUCUCUCCAAAGCUUACCCAGCAAUAGGAACUCCC

AUACCAUUUGAUAAAAUUUUGUAUAACAGGCAACAGCAUUAUGACCCAAG

GACUGGAAUCUUUACUUGUCAGAUACCAGGAAUAUACUAUUUUUCAUACC

ACGUGCAUGUGAAAGGGACUCAUGUUGGGUAGGCCUGUAUAAGAAUGGC

ACCCCUGUAAUGUACACCUAUGAUGAAUACACCAAAGGCUACCUGGAUCA

GGCUUCAGGGAGUGCCAUCAUCGAUCUCACAGAAAAUGACCAGGUGUGGC

UCCAGCUUCCCAAUGCCGAGUCAAAUGGCCUAUACUCCUCUGAGUAUGUC

CACUCCUCUUUCUCAGGAUUCCUAGUGGCUCCAAUGUGAGUACACACAGA

GCUAAUCUAAAUCUUGUGCUAGAAAAAGCAUUCUCUAACUCUACCCCACC

CUACAAAAUGCAUAUGGAGGUAGGCUGAAAAGAAUGUAAUUUUUAUUUUC

UGAAAUACAGAUUUGAGCUAUCAGACCAACAAACCUUCCCCCUGAAAAGU

GAGCAGCAACGUAAAAACGUAUGUGAAGCCUCUCUUGAAUUUCUAGUUAG

CAAUCUUAAGGCUCUUUAAGGUUUUCUCCAAUAUUAAAAAAUAUCACCAA

AGAAGUCCUGCUAUGUUAAAAACAAACAACAAAAACAAACAACAAAAAA

AAAAUUAAAAAAAAAAACAGAAAUAGAGCUCUAAGUUAUGUGAAAUUUGA

UUUGAGAAACUCGGCAUUUCCUUUUUAAAAAGCCUGUUUCUAACUAUGA

AUAUGAGAACUUCUAGGAAACAUCCAGGAGGUAUCAUAUAACUUUGUAGA

ACUUAAAUACUUGAAUAUUCAAAUUUAAAAGACACUGUAUCCCCUAAAAU

AUUUCUGAUGGUGCACUACUCUGAGGCCUGUAUGGCCCCUUUCAUCAAUA

UCUAUUCAAAUAUACAGGUGCAUAUAUCUUGUUAAAGCUCUUUAUAUAAA

AAAGCCCCAAAAUAUUGAAGUUCAUCUGAAAUGCAAGGUGCUUUCAUCAA

UGAACCUUUCAAACUUUUCUAUGAUUGCAGAGAAGCUUUUUAUAUACCC

AGCAUAACUUGGAAACAGGUAUCUGACCUAUUCUUAUUUAGUUAACACAA

GUGUGAUUAAUUUGAUUUCUUUAAUUCCUUAUUGAAUCUUAUGUGAUAUG

-continued

```
AUUUUCUGGAUUUACAGAACAUUAGCACAUGUACCUUGUGCCUCCCAUUC

AAGUGAAGUUAUAAUUUACACUGAGGGUUUCAAAAUUCGACUAGAAGUGG

AGAUAUAUUAUUUAUUUAUGCACUGUACUGUAUUUUUAUAUUGCUGUUUA

AAACUUUUAAGCUGUGCCUCACUUAUUAAAGCACAAAAUGUUUUACCUAC

UCCUUAUUUACGACGCAAUAAAAUAACAUCAAUAGAUUUUUAGGCUGAAU

UAAUUUGAAAGCAGCAAUUUGCUGUUCUCAACCAUUCUUUCAAGGCUUUU

CAUUGUUCAAAGUUAAUAAAAAAGUAGGACAAUAAAGUGAAAAAAAAAA

AAAAAAA
```

XVII. Computer Systems

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Computer Systems

Figure 13:
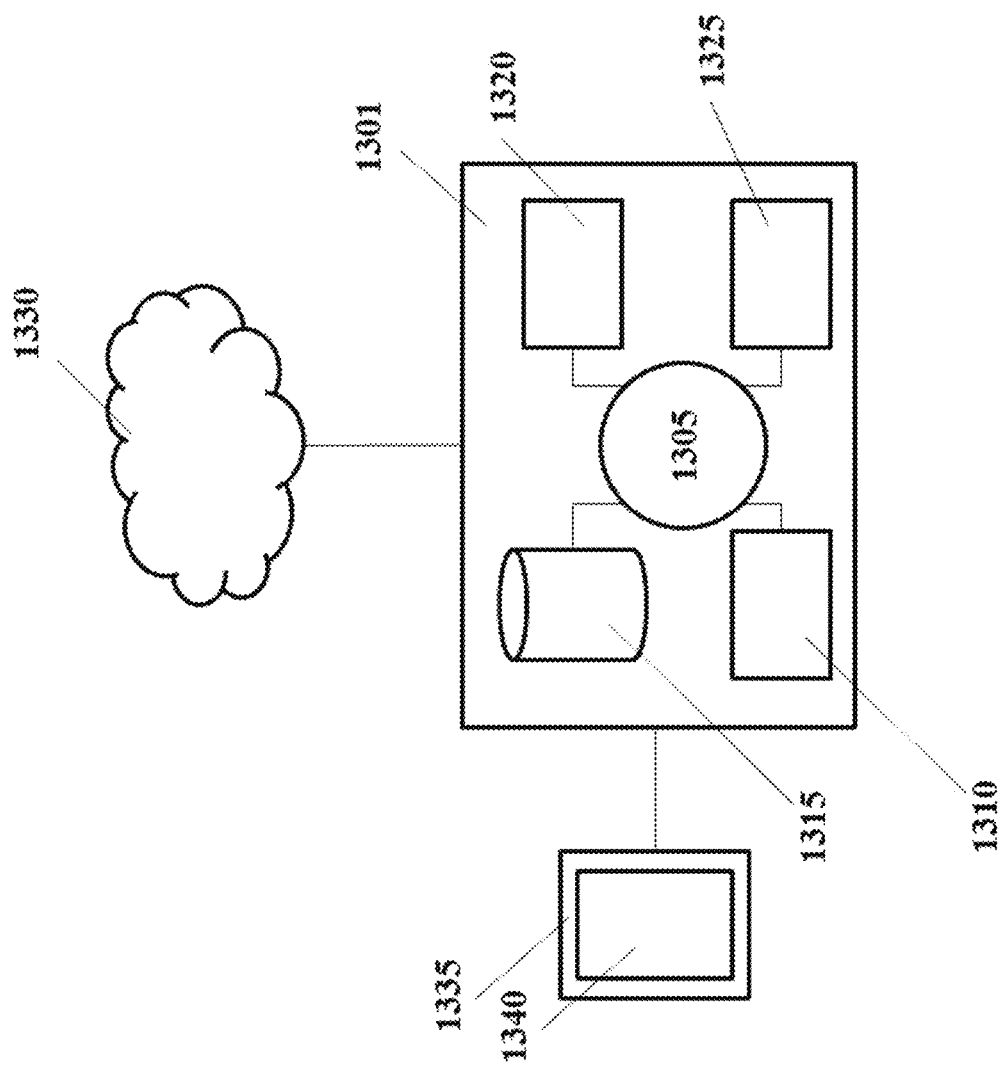
FIG. 13 shows a computer system that is programmed or otherwise configured to implement methods provided herein.

The present disclosure provides computer systems that are programmed to implement methods of the disclosure. FIG. 13 shows a computer system 1301 that is programmed or otherwise configured to identify biomarkers for a cancer, such as a breast cancer. The computer system 1301 can regulate various aspects of the analysis of the present disclosure, such as, for example, it can analyze a cohort of biomarkers from a population of subjects afflicted with a cancer; it can identify a first subset from said cohort of said biomarkers that has at least a 3-fold higher expression level in said cancer as compared to tissue samples that do not contain cancer, such a healthy control biomarker; it can identify a second subset from said first subset of said biomarkers that have a false discovery rate of less than a $10^{-6}$ it can use at least one biomarker from said second subset of said biomarkers as input for a machine learning algorithm such as correlation feature selection (CFS); and it can further output one or more biomarkers that identify said cancer. The computer system 1301 can be an electronic device of a user or a computer system that is remotely located with respect to the electronic device. The electronic device can be a mobile electronic device.

The computer system 1301 includes a central processing unit (CPU, also "processor" and "computer processor" herein) 1305, which can be a single core or multi core processor, or a plurality of processors for parallel processing. The computer system 1301 also includes memory or memory location 1310 (e.g., random-access memory, read-only memory, flash memory), electronic storage unit 1315 (e.g., hard disk), communication interface 1320 (e.g., network adapter) for communicating with one or more other systems, and peripheral devices 1325, such as cache, other memory, data storage and/or electronic display adapters. The memory 1310, storage unit 1315, interface 1320 and peripheral devices 1325 are in communication with the CPU 1305 through a communication bus (solid lines), such as a motherboard. The storage unit 1315 can be a data storage unit (or data repository) for storing data. The computer system 1301 can be operatively coupled to a computer network ("network") 1330 with the aid of the communication interface 1320. The network 1330 can be the Internet, an internet and/or extranet, or an intranet and/or extranet that is in communication with the Internet. The network 1330 in some cases is a telecommunication and/or data network. The network 1330 can include one or more computer servers, which can enable distributed computing, such as cloud computing. The network 1330, in some cases with the aid of the computer system 1301, can implement a peer-to-peer network, which may enable devices coupled to the computer system 1301 to behave as a client or a server. The system can train a number of classifiers that identify breast cancer.

The CPU 1305 can execute a sequence of machine-readable instructions, which can be embodied in a program or software. The instructions may be stored in a memory location, such as the memory 1310. The instructions can be directed to the CPU 1305, which can subsequently program or otherwise configure the CPU 1305 to implement methods of the present disclosure. Examples of operations performed by the CPU 1305 can include fetch, decode, execute, and writeback.

The CPU 1305 can be part of a circuit, such as an integrated circuit. One or more other components of the system 1301 can be included in the circuit. In some cases, the circuit is an application specific integrated circuit (ASIC).

The storage unit 1315 can store files, such as drivers, libraries and saved programs. The storage unit 1315 can store user data, e.g., user preferences and user programs. The computer system 1301 in some cases can include one or more additional data storage units that are external to the computer system 1301, such as located on a remote server that is in communication with the computer system 1301 through an intranet or the Internet.

The computer system 1301 can communicate with one or more remote computer systems through the network 1330. For instance, the computer system 1301 can communicate with a remote computer system of a user (e.g., it can access electronic data from the TCGA project). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1301 via the network 1330.

Methods as described herein can be implemented by way of machine (e.g., computer processor) executable code stored on an electronic storage location of the computer system 1301, such as, for example, on the memory 1310 or electronic storage unit 1315. The machine executable or machine readable code can be provided in the form of software. During use, the code can be executed by the processor 1305. In some cases, the code can be retrieved from the storage unit 1315 and stored on the memory 1310 for ready access by the processor 1305. In some situations, the electronic storage unit 1315 can be precluded, and machine-executable instructions are stored on memory 1310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1301 can include or be in communication with an electronic display 1335 that comprises a user interface (UI) 1340 for providing, for example, an output listing one or more biomarkers that identify a cancer, such as breast cancer. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1305.

XIII. Kits

In one aspect, the invention provides kits comprising any of the primers and reagents for detecting the 3-gene panel of biomarkers described in this application. The kits may comprise at least one primer sequence that has at least 90% identity to any one of SEQ ID NO: 1-SEQ ID NO: 356, and a buffer solution/system. In some embodiments, the kit comprises at least one forward primer that has at least 90% identity to any one of SEQ ID NO:1-40, SEQ ID NO:56-150, or SEQ ID NO:228-248 and at least one reverse primer that has at least 90% identity to any one of SEQ ID NO:41-85, SEQ ID NO: 151-227, or SEQ ID NO:249-279. In some embodiments, the kit comprises at least one forward reference primer that has at least 90% identity to any one of SEQ ID NO:280-293 or SEQ ID NO:311-324 and at least one reverse reference primer that has at least 90% identity to any one of SEQ ID NO: 294-310 or SEQ ID NO: 325-338. In some embodiments, the kit comprises at least one forward positive control primer that has at least 90% identity to any one of SEQ ID NO:339-347 and at least one reverse positive control primer that has at least 90% identity to any one of SEQ ID NO: 348-356. In some embodiments, the kit comprises at least one forward and reverse primer sequence for each of IBSP, MMP11, and COL10A that has at least 90% identity to any of the primer combinations in Table 13, Table 14, and Table 15. In some embodiments, the kit comprises at least one forward and reverse primer sequence for each of TTC5 and C2orf44 that has at least 90% identity to any of the primer combinations in Table 16 and Table 17. In some embodiments, the kit comprises at least one forward and reverse primer sequence for chr3 gDNA that has at least 90% identity to any of the primer combinations in Table 18.

In some instances, the kits further comprise a DNA-intercalating dye or a fluorescent probe, such as a TaqMan compatible probe. A TaqMan compatible probe may comprise a short oligonucleotide sequence designed to hybridize to the desired gene, in combination with a 5'-fluorophore and a 3'-quencher attached to either end of the oligonucleotide. In some instances the kit also comprises a negative control sample, a positive control sample, or a using a synthetic nucleotide control.

The kits can further comprise a set of reagents for a polymerase chain reaction. Such reagents for a polymerase chain reaction include a suitable thermostable DNA polymerase (e.g. Taq polymerase, which may be a hot-start polymerase to improve fidelity) solution, a solution of 4 dNTPs (e.g. dATP, dTTP, dGTP, dCTP), a buffer solution, DNAse-free water, and/or solutions of PCR stabilizers/enhancers. Buffers are prepared at the pH optimum for the enzyme and may additionally comprise salts such as KCl, NaCl, and/or MgCl2, reducing agents such as DTT or B-me, detergents such as triton-x or tween-20, and/or glycerol as useful for function of the enzyme. Stabilizers/additives may include agents such as DMSO, betaine monohydrate, formamide, MgCl2, glycerol, BSA, tween-20, Tetramethyl ammonium chloride, and/or 7-deaza-2'-deoxyguanosine. For qPCR applications, a polymerase chain reaction kit may include suitable fluorescent DNA-binding dyes such as SYBR Green, ethidium bromide, or EvaGreen.

In some examples, the set of reagents can be for a reverse-transcriptase polymerase chain reaction. Reagents for a reverse-transcriptase polymerase chain reaction include a suitable reverse transcriptase (such as Maloney murine leukemia virus, M-MLV, reverse transcriptase) solution, solution of 4 dNTPs (e.g. dATP, dTTP, dGTP, dCTP), a buffer solution, an RNAse inhibitor solution, and/or RNAse-free water. In the case of solutions for reverse-transcriptase polymerase chain reaction, all the reagents (e.g. dNTPs, water, buffer) are certified RNAse free to prevent template degradation.

The kit can further comprise written instructions for a use thereof. Such instructions may include instructions for isolating/preparing the sample, operating instrumentation (e.g. qPCR instrumentation), and/or data interpretation The kit can further comprise components for touch-prep. Such components include poly-D-lysine coated glass slides, an RNA isolation kit, and/or spin columns (suitable for isolation/purification of RNA) and collection tubes. A minimal RNA isolation kit may comprise a solution RNAse-free sample disruption buffer, solutions of RNA isolation reagents (e.g. Trizol or phenol/chloroform or phenol/chloroform/isoamyl alcohol mixtures), RNAse-free DNase, and/or a solution of an RNAse inhibitor.

The kit can further comprise components for tumor/tissue dissociation. Such components include a) solutions of enzymes for extracellular matrix (ECM) or other protein degradation such as collagenase, trypsin, elastase, hyaluronidase, and/or papain; b) solutions for lysis of red blood cells from tissue (e.g. a hypotonic lysis buffer); c) a tissue dissociator (e.g. Miltenyi gentleMACS Octo Tissue Dissociator); d) a stabilization buffer (e.g. containing protease, DNAse, and/or RNAse inhibitors); e) a lysis buffer (a buffered solution, optionally hypotonic, containing ionic or nonionic detergents such as Triton X-100, tween-20, beta-octyl glucoside, and/or SDS).

In some embodiments, the kit is a kit for the detection of positive surgical margins. Such a kit includes components such as instructions, primers or primer combinations outlined above (e.g. forward and reverse primers for each target gene, forward and reverse primers for a reference gene, and forward and reverse primers for a gDNA control gene), touch prep components as described above, reagents for polymerase chain reaction, and reagents for reverse-polymerase chain reaction. In some embodiments such a kit consists of as instructions, touch prep components as described above, reagents for polymerase chain reaction, and reagents for reverse-polymerase chain reaction.

In some embodiments, the kit is a kit for detection of molecular complete response (mCR). Such a kit includes components such as instructions, primers or primer combinations outlined above (e.g. forward and reverse primers for each target gene, forward and reverse primers for a reference gene, and forward and reverse primers for a gDNA control gene), components for tumor/tissue dissociation as described above, an RNA isolation kit, and/or spin columns suitable for isolation/purification of RNA.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

Example 1. A 3-Gene Test for Residual Disease/Pathologic Complete Response (pCR)

General Methods

Data from the TCGA project was analyzed to inform the identification of a cohort of biomarkers from a population of subjects afflicted with a cancer. In addition, lumpectomies were performed on small, early-stage tumors. cDNA from these samples was prepared from clinical samples and q-PCR performed according to standard protocols. A variety of standard protocols and kits for cDNA preparation/q-PCR are known to those of skill in the art. Exemplary protocols include, those from ThermoFisher (e.g. Manual for Power SYBR® Green RNA-to-$C_T$™ 1-Step Kit Part Number 4391003 Rev. D; Manual for EXPRESS One-Step; SuperScript® qRT-PCR Kits, Rev. Date: 28 Jun. 2010 Manual part no. A10327), BioRad (e.g. Manual for iTaq™ Universal SYBR® Green One-Step Kit 10032048 Rev B), NEB (e.g. Luna® Universal One-Step RT-qPCR Kit Protocol (E3005)), Qiagen (e.g. QuantiFast SYBR Green RT-PCR Handbook ver July 2011, U.S. Pat. No. 5,994,056, and U.S. Pat. No. 6,171,785), Roche (e.g. Transcriptor One-Step RT-PCR Kit; FastStart Universal SYBR Green Master (Rox), each of which are specifically incorporated by reference herein.

Inclusion/Exclusion Criteria.

Since genomic signatures may evolve during metastasis, AJCC TNM staging (<T3) was used to restrict samples to female patients who would be eligible for a lumpectomy (see TABLE 19). One sample was excluded for failing quality control, and 8 samples were excluded for having clinical data. Inclusion/exclusion criteria preserved the racial and ethnic representation of the U.S. population, except for the only available American Indian/Alaskan Native (AI/AN) subject, who did not satisfy our inclusion criteria. 1,014 early-stage tumors were divided (T1-T2) into a training set with 939 samples and an independent test with 75 samples. The early-stage tumor sets (Cross-validation Set and Independent Set #1) also included healthy samples from patient with late-stage tumors. This test was designed to detect early-stage tumors, but the analysis also included 175 late-stage tumors (T3-T4) as a second independent test set. In sum, novel biomarkers for cancer were identified when a computer system was used to analyze a cohort of biomarkers from the aforementioned population of subjects afflicted with a cancer. The method identified a first subset of biomarkers that had at least a 3-fold higher expression level in said cancer as compared to a healthy control biomarker; and a second subset from said first subset of said biomarkers that provided a false discovery rate for said cancer that was less than 0.000001. The markers identified were used to train a machine learning algorithm and were experimentally validated.

The method identified a 3-gene set of markers from a plurality of biomarkers from 939 RNA Seq samples. The method was tested on two independent RNA Seq test sets (TABLE 19A and TABLE 19B). The selected 3-gene set of markers correctly classified 96.2% of 939 samples in the Cross-validation Set (early stage, AJCC 1NN4 Tumor Stages T1-12). Since these results were unexpected, we tested whether the performance estimates from cross-validation were inflated by potential modeling errors (e.g. overfitting). First, a suite of negative controls did not detect any modeling errors in the cross validation. Second, the classifier was trained on all 939 samples in the cross-validation set, and tested on a hold-out set of 75 samples. The 3-gene Random Forest test correctly classified 97.3% of 75 early-stage samples in one independent test set, and correctly classified 94.3% of 175 late-stage samples in a second independent test set. Performance was not significantly affected by race, ethnicity, tumor stage, or ER/PR/Her2 status. By definition, overfit models have higher performance from resampling estimates like cross validation than on independent validation sets. In this case, cross validation estimates and performance on the independent validation set were within the 95% confidence intervals. These results therefore firmly exclude overfitting.

TABLE 19A

|  | Available samples | Cross validation Early-Stage | | | Independent Test Set #1: | | |
|---|---|---|---|---|---|---|---|
|  |  | Sample Size | Correctly classified | P-value (Fisher's) | Sample Size | Correctly classified | P-value (Fisher's) |
| Sample Size | 1210 | 939 | 903 |  | 75 | 73 |  |
| Gender |  |  |  |  |  |  |  |
| Female | 1197 | 939 | 903 |  | 75 | 73 |  |
| Male | 13 | — | — |  | — | — |  |
| Sample Type |  |  |  |  |  |  |  |
| Tumor | 1089 | 851 | 820 |  | 50 | 49 |  |
| Healthy | 114 | 88 | 83 |  | 25 | 24 |  |
| Metastatic | 7 | — | — |  | — | — |  |
| Race |  |  |  | 0.6605 |  |  | 0.4843 |
| AI or AN[1] | 1 | — | — |  | — | — |  |
| Asian | 62 | 48 | 47 |  | 4 | 4 |  |
| Black or AA[1] | 187 | 147 | 140 |  | 11 | 10 |  |
| White | 861 | 672 | 648 |  | 54 | 53 |  |
| NA/NE[2] | 99 | 72 | 68 |  | 6 | 6 |  |
| Ethnicity |  |  |  | 1.0000 |  |  | 1.0000 |
| Hispanic or Latino | 39 | 30 | 29 (96.7%) |  | 3 | 3 (100.0%) |  |
| Not Hispanic or Latino | 201 | 154 | 148 (96.1%) |  | 18 | 18 (100.0%) |  |
| NA/NE/Unknown[2] | 970 | 755 | 726 (96.2%) |  | 54 | 52 (963%) |  |
| Tumor Pathology |  |  |  | 0.3293 |  |  | 1.0000 |
| T1 | 281 | 263 | 251 |  | 17 | 17 |  |
| T2 | 632 | 588 | 569 |  | 33 | 32 |  |
| T3 % T4 | 172 | — | — |  | — | — |  |
| TX (Unknown) | 4 | — | — |  | — | — |  |
| Estrogen |  |  |  | 0.6678 |  |  | 1.0000 |
| Positive | 801 | 621 | 597 |  | 34 | 33 |  |
| Negative | 238 | 190 | 183 |  | 14 | 14 |  |
| Indeterminate | 2 | 1 | 1 |  | — | — |  |
| Not Evaluated | 48 | 39 | 39 |  | 2 | 2 |  |
| Progesterone |  |  |  | 0.1206 |  |  | 1.0000 |
| Positive | 694 | 544 | 522 |  | 28 | 27 |  |
| Negative | 342 | 263 | 255 |  | 20 | 20 |  |
| Indeterminate | 4 | 4 | 3 (75.0%) |  | — | — |  |
| Not Evaluated | 49 | 40 | 40 |  | 2 | 2 |  |
| Her2/Neu Status |  |  |  | 0.9653 |  |  | 0.1400 |
| Positive | 162 | 127 | 123 |  | 9 | 9 |  |
| Negative | 560 | 438 | 420 |  | 27 | 27 |  |
| Equivocal | 178 | 150 | 145 |  | 5 | 4 (80.0%) |  |
| Not Evaluated | 12 | 7 | 7 |  | 2 | 2 |  |
| NA/NE[2] | 177 | 129 | 125 |  | 7 | 7 |  |
| Triple Negative |  |  |  | 0.3751 |  |  | 0.2580 |
| Triple Negative | 116 | 94 | 89 |  | 6 | 6 |  |
| Not Triple | 973 | 757 | 731 |  | 44 | 43 |  |

[1]American Indian (AI), Alaska Native (AN), African American (AA)
[2]Not Available (NA), Not Evaluated (NE)

TABLE 19B

| | Available samples | Cross validation Early-Stage (T1-T2) | | | Independent Test Set #2: Late-Stage (T3-T4) | | |
|---|---|---|---|---|---|---|---|
| | | Sample Size | Correctly classified | P-value (Fisher's) | Sample Size | Correctly classified | P-value (Fisher's) |
| Sample Size | 1210 | 939 | 903 | | 175 | 165 | |
| Gender | | | | | | | |
| Female | 1197 | 939 | 903 | | 175 | 165 | |
| Male | 13 | — | — | | — | — | |
| Sample Type | | | | | | | |
| Tumor | 1089 | 851 | 820 | | 175 | 165 | |
| Healthy | 114 | 88 | 83 | | — | — | |
| Metastatic | 7 | — | — | | — | — | |
| Race | | | | 0.6605 | | | 0.6840 |
| AI or AN[1] | 1 | — | — | | — | — | |
| Asian | 62 | 48 | 47 | | 10 | 9 (90.0%) | |
| Black or AA[1] | 187 | 147 | 140 | | 26 | 24 | |
| White | 861 | 672 | 648 | | 118 | 112 | |
| NA/NE[2] | 99 | 72 | 68 | | 21 | 20 | |
| Ethnicity | | | | 1.0000 | | | |
| Hispanic or Latino | 39 | 30 | 29 (96.7%) | | — | — | |
| Not Hispanic or Latino | 201 | 154 | 148 (96.1%) | | 175 | 165 (94.3%) | |
| NA/NE/Unknown[2] | 970 | 755 | 726 (96.2%) | | — | — | |
| Tumor Pathology | | | | 0.3293 | | | 1.0000 |
| T1 | 281 | 263 | 251 | | — | — | |
| T2 | 632 | 588 | 569 | | — | — | |
| T3 % T4 | 172 | — | — | | 171 | 161 | |
| TX (Unknown) | 4 | — | — | | 4 | 4 | |
| Estrogen | | | | 0.6678 | | | 0.1347 |
| Positive | 801 | 621 | 597 | | 134 | 129 | |
| Negative | 238 | 190 | 183 | | 34 | 30 | |
| Indeterminate | 2 | 1 | 1 | | 1 | 1 | |
| Not Evaluated | 48 | 39 | 39 | | 6 | 5 (83.3%) | |
| Progesterone | | | | 0.1206 | | | 0.1052 |
| Positive | 694 | 544 | 522 | | 112 | 108 | |
| Negative | 342 | 263 | 255 | | 57 | 52 | |
| Indeterminate | 4 | 4 | 3 (75.0%) | | — | — | |
| Not Evaluated | 49 | 40 | 40 | | 6 | 5 (83.3%) | |
| Her2/Neu Status | | | | 0.9653 | | | 0.1186 |
| Positive | 162 | 127 | 123 | | 23 | 23 | |
| Negative | 560 | 438 | 420 | | 90 | 86 | |
| Equivocal | 178 | 150 | 145 | | 21 | 20 | |
| Not Evaluated | 12 | 7 | 7 | | 3 | 2 (66.7%) | |
| NA/NE[2] | 177 | 129 | 125 | | 38 | 34 | |
| Triple Negative | | | | 0.3751 | | | 0.2288 |
| Triple Negative | 116 | 94 | 89 | | 16 | 14 | |
| Not Triple | 973 | 757 | 731 | | 159 | 151 | |

Biomarker Discovery.

Figure 2A:
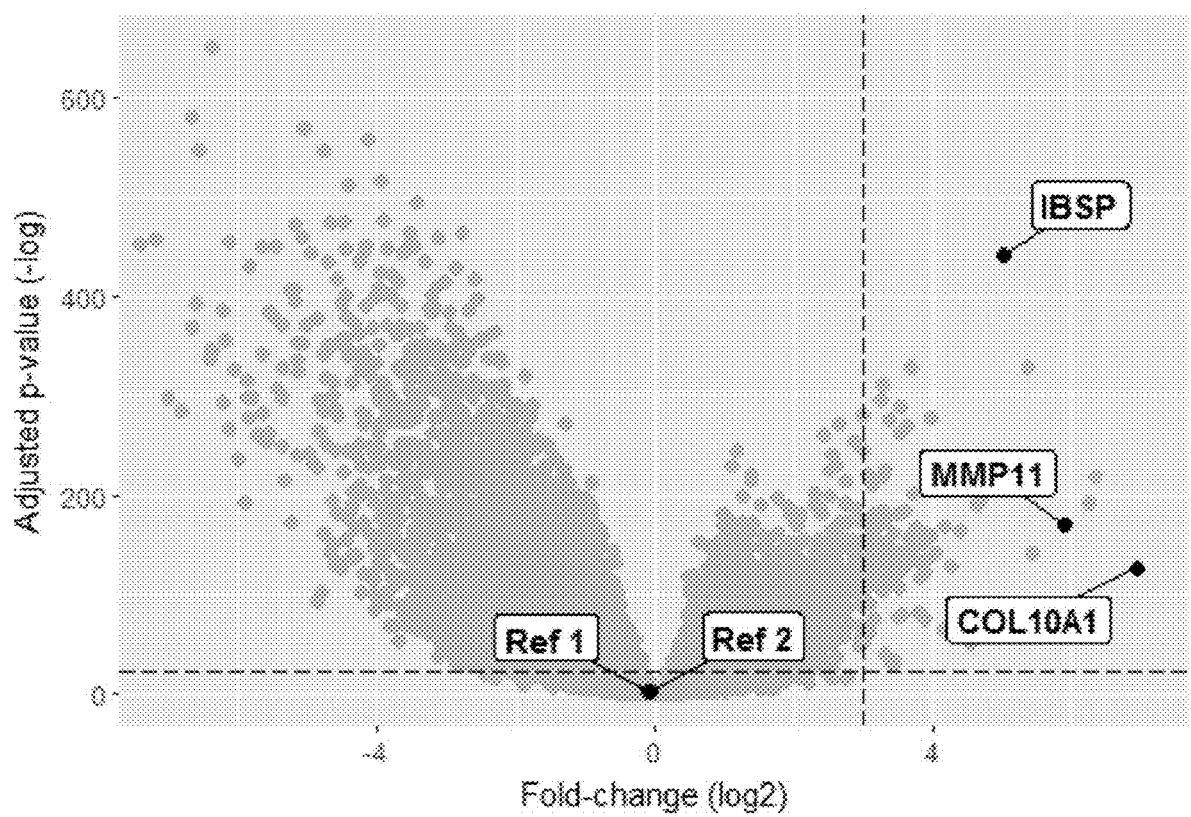
FIG. 2A is a Volcano plot of 20,253 mRNAs in 1,014 samples. RNA Seq was used to analyze 1,014 samples from early-stage tumors and healthy samples from adjacent tissue. Selected genes had the highest Correlation-based Feature Selection scores among genes that passed p-value threshold (dashed horizontal line) and fold-change threshold (dashed vertical line).
Figure 2B:
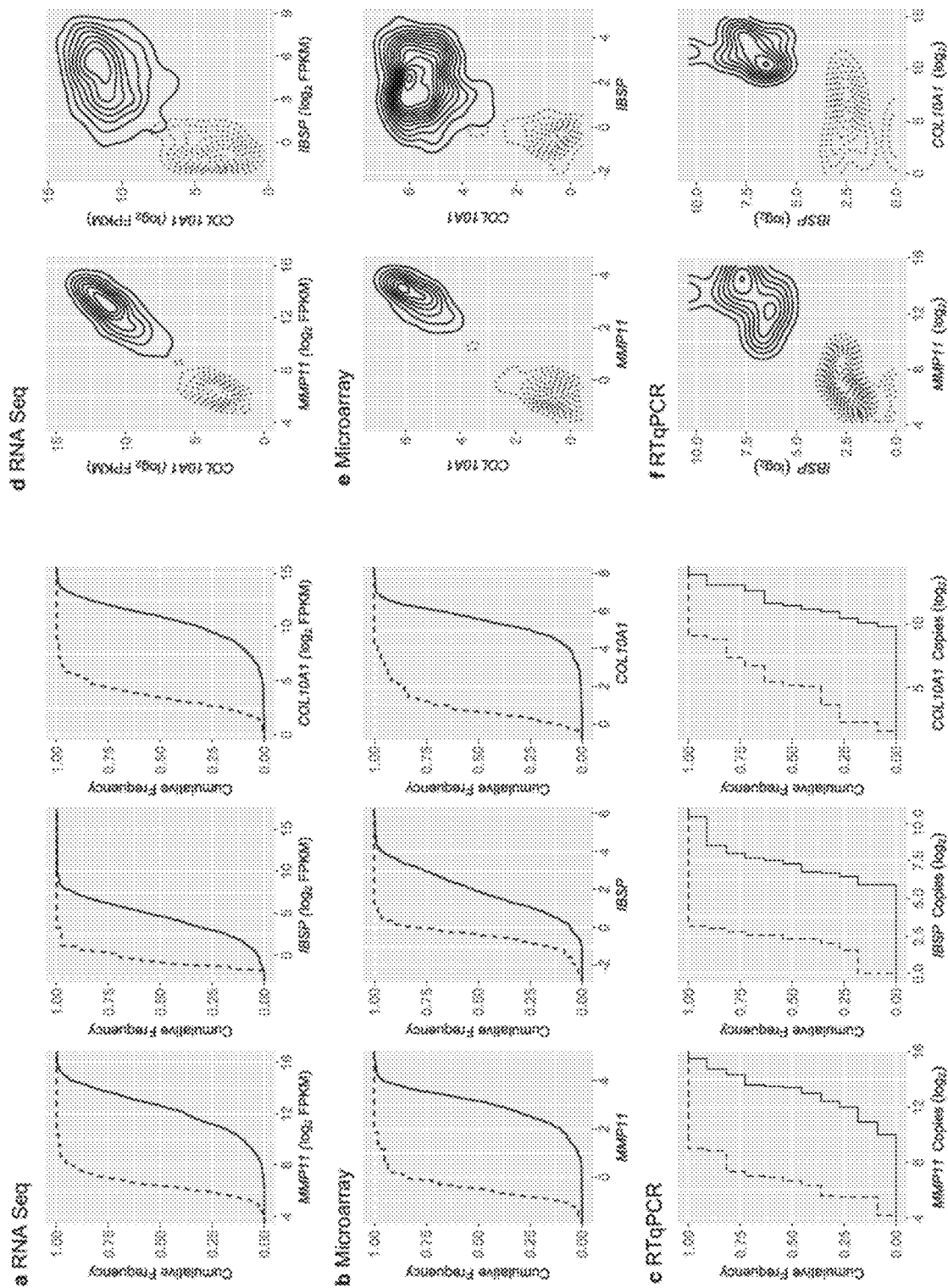
FIG. 2B panels (a-c) are cumulative frequency plots of 1,536 patient samples that show that a 3-gene set (MMP11, COL10A1, IBSP) is overexpressed in samples from early-stage tumors and adjacent healthy tissue. The genes have comparable distributions on RNA Seq samples (a), a subset of samples that were also analyzed by microarray (b), and a subset that were also analyzed by RTqPCR (c). These results confirm that expression is not platform-specific. Panels (c-e) are 2D-Density maps illustrating the advantage of a multi-analyte test over a single biomarker. Separation of tumor and healthy improves as we progress from RNA Seq to Microarray to custom RTqPCR.

A subset of biomarkers that had a large mean difference between groups, with two clearly separated distributions, was first identified using a computer system. In addition, to detect tumor cells in a population of healthy cells, additional biomarkers that had a higher level of expression in tumors than healthy samples were selected. To identify such biomarkers, genes with a $\log_2$(fold-change)=+3 and genes with a False Discovery Rate (adjusted p-value) of $p<10^{-6}$ were identified. The method identified a first subset of biomarkers that were overexpressed in tumors (FIG. 2A). Subsequently, Correlation-based Feature Selection (CF S) was applied in the first subset from the broader cohort of biomarkers to identify genes with at least a 3-fold higher expression level in the selected cancer as compared to a healthy control biomarker to select the top genes that contributed the most unique information.

Figure 3:
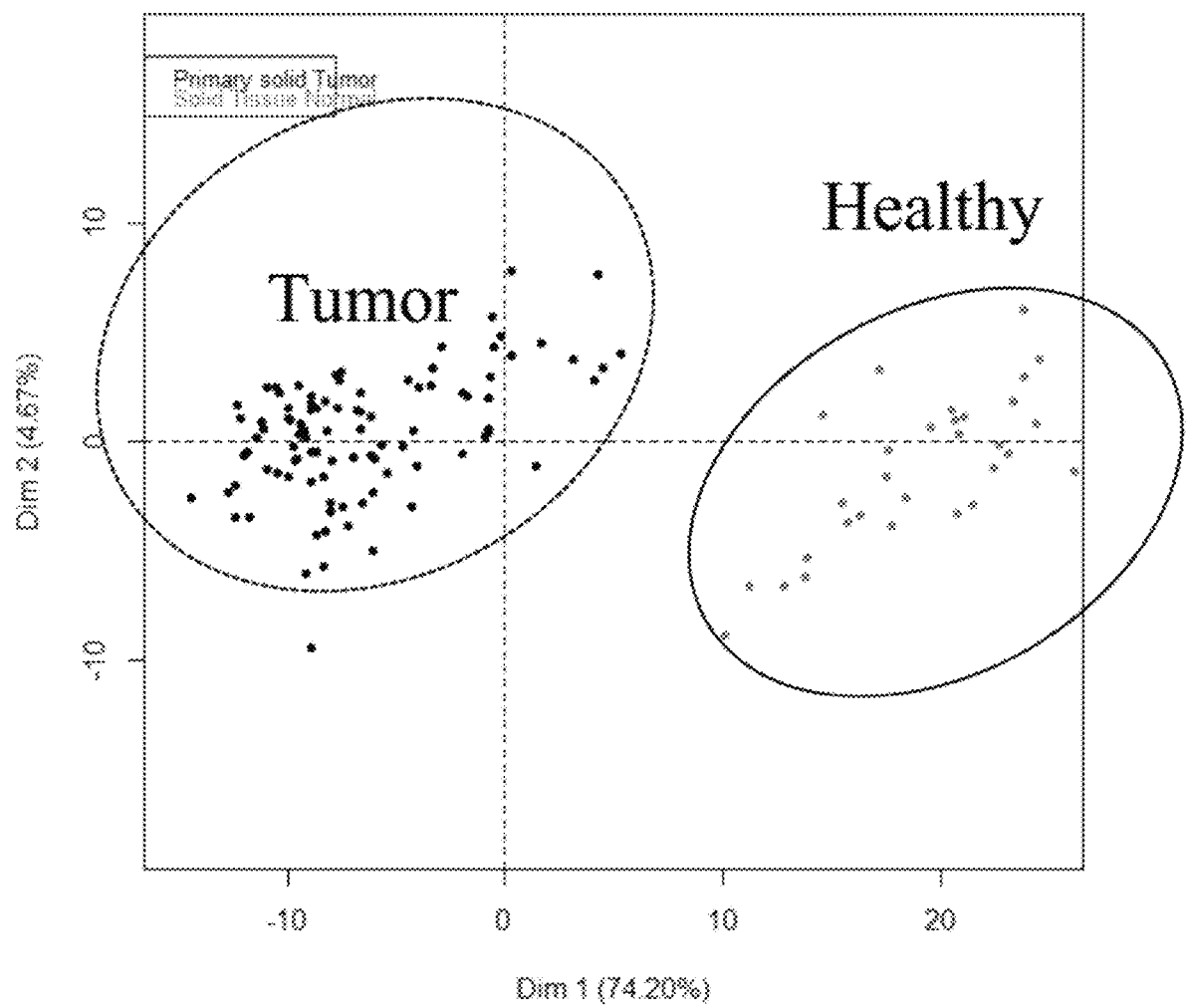
FIG. 3 is a chart showing a Principal Component Analysis (PCA) of all available microarray probes shows a clear demarcation between tumor (left dots) and healthy samples (right dots).

In addition, expression of many disease-associated genes is highly correlated. Thus, the identification of genes that contribute the most unique information informed the selection of relevant markers. For instance, estrogen signaling is the classic example in breast tumors, where multiple ER-responsive genes can be the strongest biomarkers in a given tumor. But these genes would only help identify ER+ tumors, and would miss every tumor that is not ER+. Selection of highly expressed genes with CFS, or another suitable method, allows the identification of a subset of genes that not only contribute information, but that contribute the most unique information relative to the other selected genes. Using CFS, we selected panels of 200, 100, 20, 10, 5, 4, 3, 2, and 1 gene panels. Six machine learning algorithms were tested and performed similarly in identifying gene panels. The 6 algorithms were the support vector algorithm SMO, Naïve Bayes, J48 Decision Tree, Lazy-IBk, the Multilayer Perceptron neural network, and Random Forest. The Random Forest ensemble machine learning method was used in the remaining of the experiments. There are at least 9 published classifiers for breast cancer that use gene expression, including OncoTypeDX® and PAM50. Principal Component Analysis (PCA) (FIG. 3) suggests a rationale for why the disclosed 3-gene set of markers had higher performance than existing breast cancer disease classifiers. Existing classifiers attempt to identify subgroups among the cluster of tumor samples. This leads to the strongest performance being focused on distinguishing the two most prominent groups, such as tumor and healthy (FIG. 3).

The 3-gene test had an accuracy of 94-97% when analyzed on 3 sets of RNA Seq. samples (TABLE 20). PAM50 could not be used for margin analysis because it requires samples with >50% tumor.

TABLE 20

Comparison of 3-gene test with PAM50 on RNA Seq samples

| 3-Gene Test | Accuracy | Sensitivity | Specificity | Sample Size |
|---|---|---|---|---|
| Cross-validated Set (Early-stage tumors) | 96.2% | 96.4% | 94.4% | 939 |
| Independent Test Set #1 (Early-stage tumors) | 97.3% | 98.0% | 96.0% | 75 |
| Independent Test Set #2 (Late-stage tumors) | 94.3% | 94.3% | NA | 175 |
| Microscopy (Early-stage tumors) | 64.9% | 50.9% | 69.5% | 1,201 |
| PAM50 | 97.3% | 98.8% | 83.0% | 995 |

Figure 4:
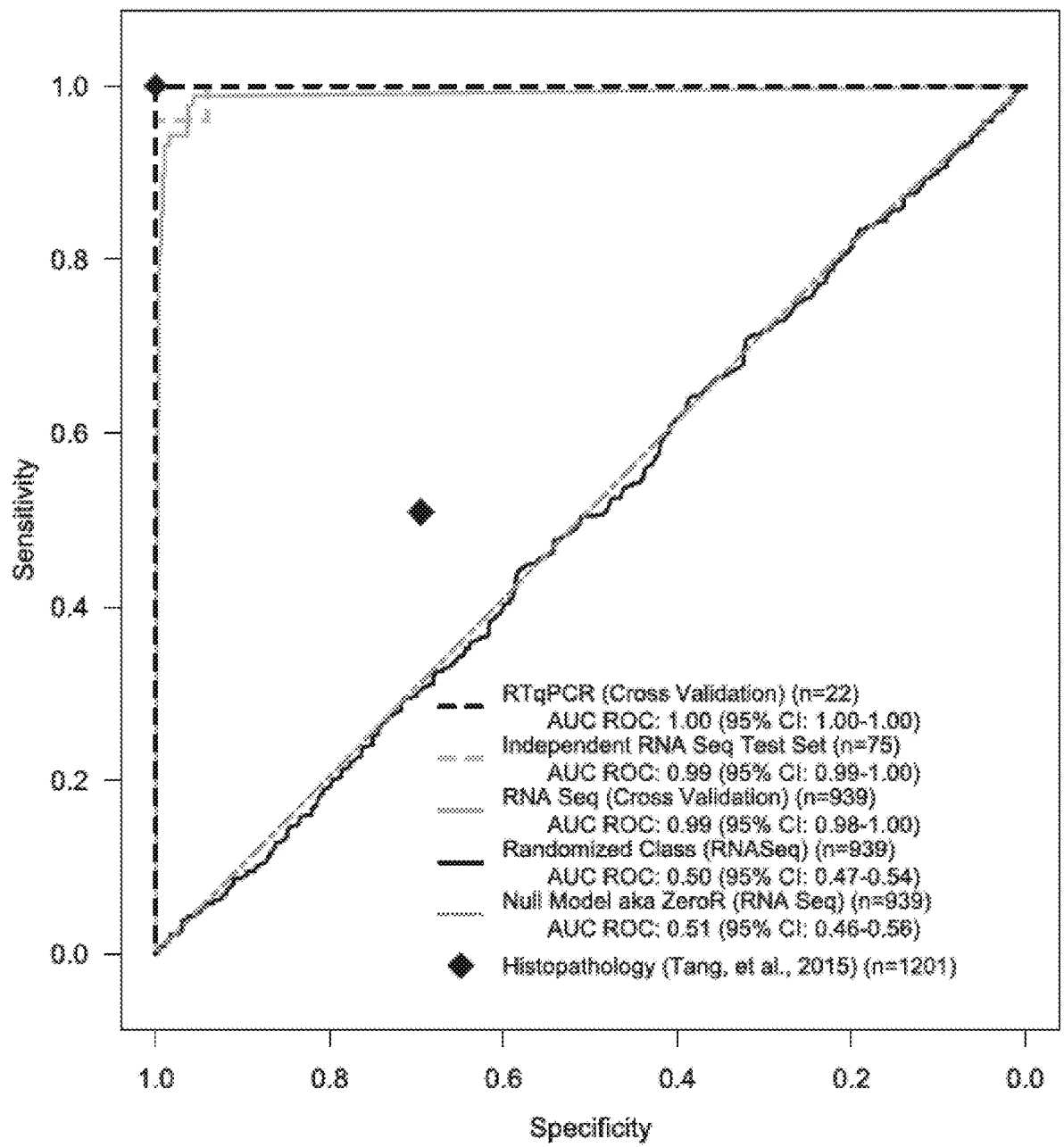
FIG. 4 depicts receiver-operator characteristic (ROC) curves of classifiers for a 3-gene set including MMP11, COL10A1, IBSP. ROC curves show the tradeoff between sensitivity and specificity over all possible thresholds. The solid dark line shows performance of the 3-gene test on 939 cross-validated RNA Seq samples.
Figure 5:
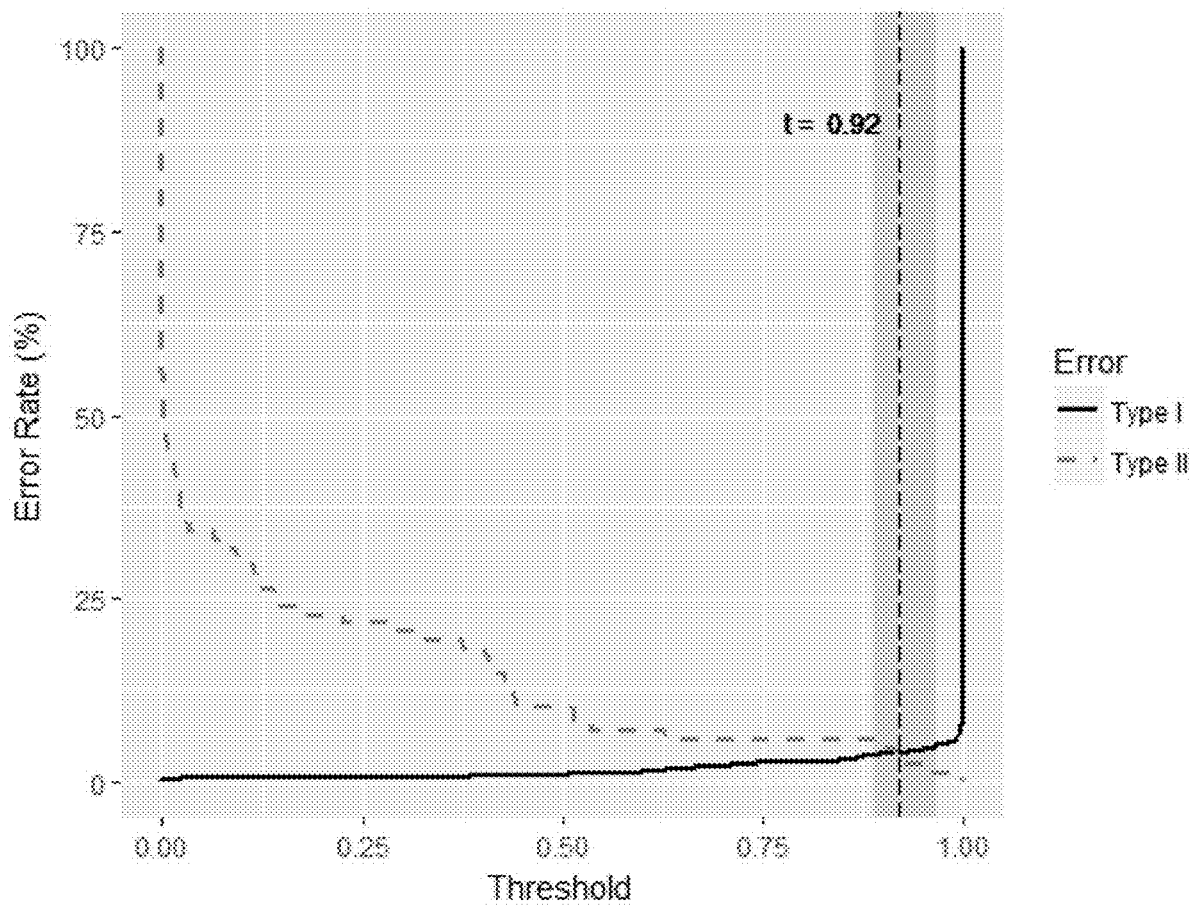
FIG. 5 illustrates an error plot of a 3-gene set (MMP11, COL10A1, IBSP) in 939 RNA Seq samples. In contrast to ROC plots, which show the tradeoff between sensitivity and specificity, error plots set the threshold based on the tradeoff between Type I and Type II errors. Type I errors (False Positives) trigger unnecessary re-excisions. Type II errors (False Negatives) indicate positive margins that were not detected. We use these tradeoffs to guide our threshold selection.

Example 2. Test Performance and Validation 1,014 RNA Seq samples were divided from early stage breast tumors and adjacent healthy tissue into a Cross-validation set of 939 samples and an Independent Test Set of 75 samples (TABLE 19). The 3-gene test correctly classified 96.2% of the samples in the Cross-validation set (TABLE 20). The Area Under the Receiver Operator Characteristic Curve (AUC ROC) was 0.990 (95% CI: 0.997-1.000) (FIG. 4). The 3-gene test has equivalent performance on the early-stage Independent Test Set: 97.3% Accuracy, 0.998 AUC ROC (95% Cl: 0.992-1.000), 98.0% Sensitivity, 96.0% Specificity, 98.0% Positive Predictive Value, and 96.0% Negative Predictive Value.

To validate the test in other tumor samples, T3 and T4 (later stage) samples, were also tested. 175 late-stage primary tumors were used as a second independent test set. In this analysis, the classifier correctly detects 94.3% of late-stage tumors. In all tests sets, the 3-gene test performed equally well regardless of racial groups or clinical subtypes (ER±, PR, Her2±) (see TABLE 19).

10-Fold Cross Validation (CV).

Our classifier combines a 3-gene set of markers including MMP11, IBSP, and COL10A1, using the Random Forest machine learning algorithm. We used ten-fold CV to estimate performance with RNA Seq data. For ten-fold CV, each of the 939 samples was used once (and only once) in 1 of 10 independent validation sets. The first iteration used subsets 2-10 (S2.10) as a training set (T1), while subset 1 (Si) was withheld as the validation set (VI). This was repeated on a total of 10 independent validation sets.

Negative Controls for Cross Validation.

After analyzing test performance, a panel of four separate negative controls was created to demonstrate that the modelling was performed correctly.

Negative Control I: Randomized, Fictitious Class Labels to Detect Overfitting

Figure 6:
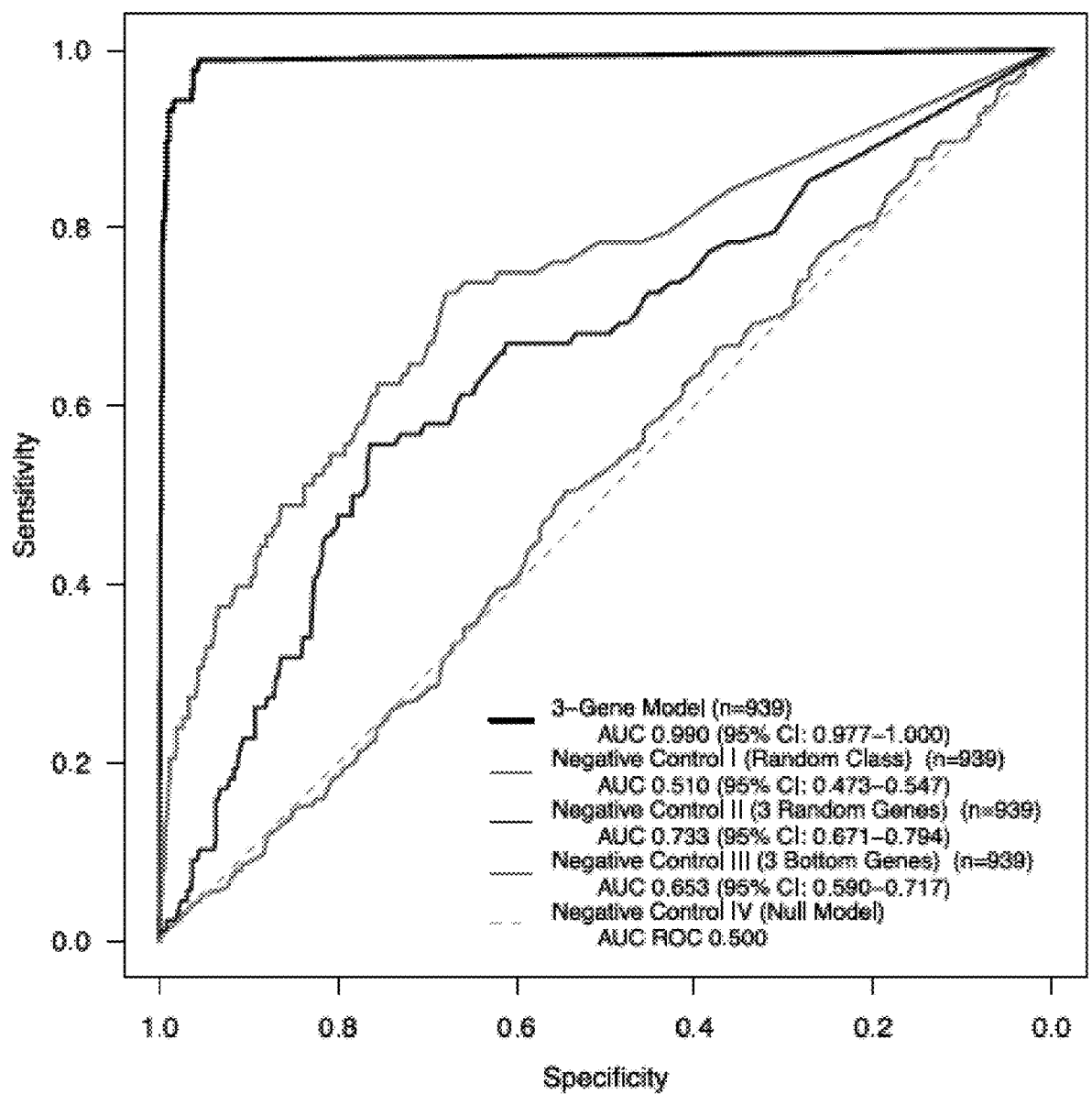
FIG. 6 is a graph illustrating that negative controls to detect overfitting demonstrate that predictive models were correctly cross-validated (n=939 RNA Seq samples).

Biomarker selection workflow was performed on a dataset with randomized class labels to detect overfitting. Using the existing classification of samples in the dataset as either Tumor or Healthy, markers were randomly assigned to a fictitious class or to a gene expression class (Class A or B). The workflow was repeated in the same manner used to develop the 3-gene test, this time trying to distinguish Class A from B. The 3 best genes were selected in each of 10 cross validation folds, and used Random Forest to train a classifier for each fold. Subsequently, 10 independent test sets were used to determine performance of the 10 models. By performing the disclosed workflow on a dataset with randomized class labels, the strategy detects overfitting. FIG. 6, Negative Control I (Random Class) clearly shows no evidence of overfitting: 0.51 Area Under the ROC Curve, 51.9% Accuracy, 51.6% Sensitivity, 52.1% Specificity.

Negative Control II: Randomly Selected Genes 3 randomly selected genes were modeled in each of 10 cross validation folds (FIG. 6): 0.733 AUC ROC, 72.6% Accuracy, 73.8% Sensitivity, 61.8% Specificity, however randomly selected genes perform much worse than our 3-Gene Test. This data demonstrates that randomly selected genes do not provide an adequate set of biomarkers.

Negative Control III: Reversed Selection Criteria

Poorly performing genes were selected by reversing the disclosed selection criteria: i.e., genes with poor p-values and small differences between tumor and healthy samples were selected in the reversed selection criteria (FIG. 6): 0.653 AUC ROC, 61.9% Accuracy, 61.5% Sensitivity, and 65.4% Specificity. The ROC plot confirms that poor genes provide less information than other disclosed genes.

Negative Control IV: Comparison to Null Model

We applied a Null Model to our dataset and compared the performance of our 3-gene panel to it. The Null Model consistently guesses that each sample is a member of the most prevalent class; in this case, that each sample is tumor (FIG. 6, dashed line). The 3-gene test (FIG. 6, dark line) has a p-value smaller than $5 \times 10^{-11}$ compared to the Null Model. While this provides a performance benchmark, it also models the diagnostic performance of a treatment strategy. Some well-intentioned surgeons proposed taking additional tissues (routine second margins) from all patients. Like routine second margins, the Null Model assumes that all patients have positive margins. FIG. 4 shows how the sensitivity and specificity of the Null Model (dashed line) compares to microscopy.

Example 3. Assay Development for qPCR Test

Primer Design.

Hundreds of primers were designed for use in in-silico evaluations. Approximately 40 primer pairs were synthesized and tested empirically using synthetic cDNA template. For all experiments, we used clinical-grade reagents and pipettes that are certified to 1508655 standards. qPCR reagents were manufactured in cGMP conditions under ISO9001 management in a facility that is ISO13485-registered.

The disclosed one-step RTqPCR assay uses targeted primers to reverse transcribe RNA into cDNA, followed by qPCR amplification of cDNA and detection using a DNA-intercalating dye. Synthetic templates were utilized to optimize the concentration of each primer (titrations of primer concentrations) and annealing temperatures (temperature gradients). Some RNA primers were designed to span exon junctions. For exon-spanning primers, genomic DNA from HeLa cells was used to verify that RNA quantification is not impacted by the presence of genomic DNA. For each primer pair, a synthetic template was used to determine performance parameters: 10-fold dilutions (5 technical replicates of 6 concentrations), 2-fold dilutions (7 technical replicates of 6 concentrations), and 24 no-template controls. Lastly, pooled RNA from 3 invasive breast tumors was used to test each primer pair. The testing evaluated 3 tumor-specific genes (IBSP, MMP11, and COL10A1), 2 reference genes (C2orf44 and TTC5), and a control to detect genomic DNA, chr3 gDNA. For each primer pair, 2 negative controls were included and 3 technical replicates were conducted. All RNA experiments also included a positive control for each primer pair. Altogether, assay development and validation involved greater than 3,700 reactions of 20-microliter reactions.

Absolute Quantification of 22 Clinical Samples.

The disclosed qPCR assays were used to analyze RNA from 22 clinical samples (11 pairs of invasive breast adenocarcinomas and adjacent healthy samples). Specificity, prevision, sensitivity, linearity, and PCR efficiency were determined for the top qPCR primer combinations, which were all designed to span exon junctions (TABLES 1-6). Performance criteria were found to satisfy MIQE and CLSI guidelines.

replicates) and 2-fold dilutions for 5 low concentrations (7 technical replicates). One concentration point overlapped in the high and low concentration series. Each primer pair includes 24 replicates of no-template controls. Error bars at each cycle represent 95% CI of technical replicates.

Figure 7A:
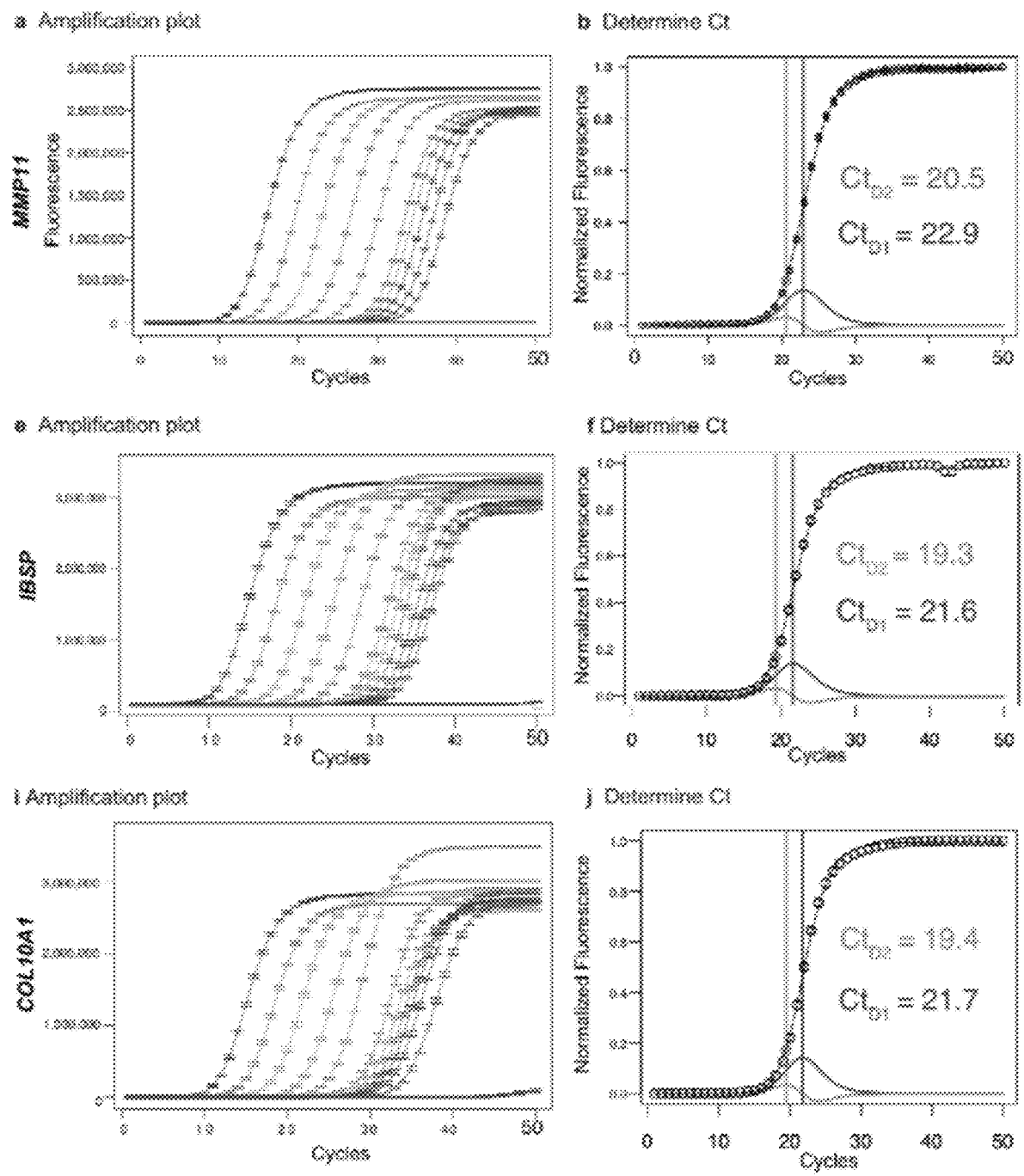
FIG. 7A and FIG. 7B depict charts showing analytic validation of qPCR assays for using clinical-grade reagents.

FIG. 7A panel b depict fluorescence versus cycle plots to determine Ct for MMP11. A 4-parameter linear model was fitted to 5 technical replicates (circles). The maximum of the second derivative was used to define the Ct (CtD2).

Figure 7B:
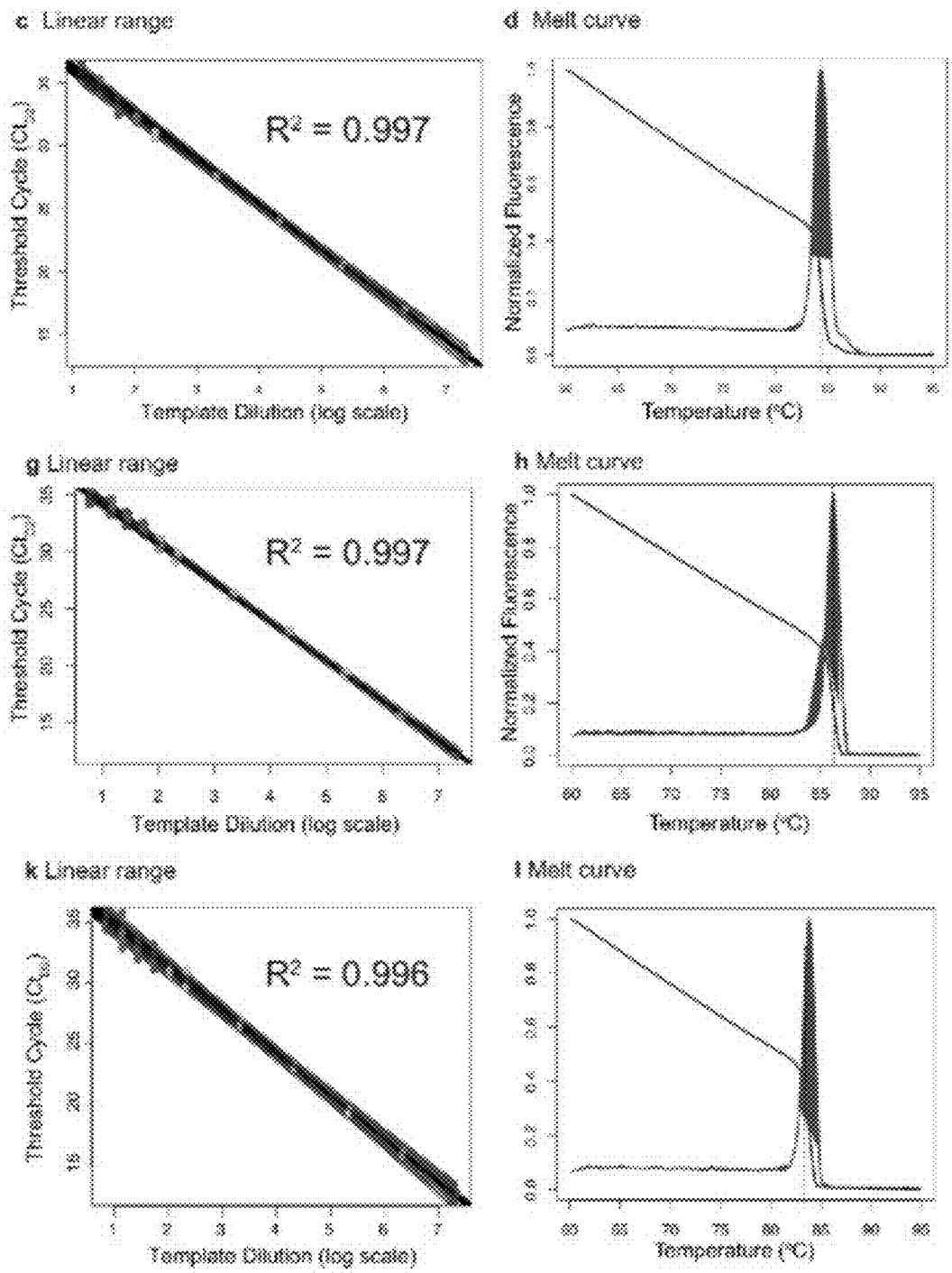

FIG. 7B panel c depicts threshold cycle versus template dilution plots to calculate linear range. The linear range is defined as the range of concentrations where CtD2 fit a straight line with R-squared >0.995. Red lines indicate 95% Confidence Intervals calculated from 200 bootstraps. FIG. 7B panel d depicts melt plots confirm to specificity of the primers. Increasing temperature denatures PCR amplicons, which decreases fluorescence. A single peak of the negative first derivative confirms the presence of a single amplicon. The peak corresponds to the expected melting temperature (dashed line).

FIG. 7A and FIG. 7B panels e-h depict charts showing analytic validation of qPCR assays for IBSP RNA as for MMP11. All assays used clinical-grade reagents. Panel e depicts amplification plots of 20 microliter qPCR reactions. 12 concentrations of synthetic cDNA template (1.1M to 0 copies per microliter), including 10-fold dilutions for 6 high concentrations (5 technical replicates) and 2-fold dilutions for 5 low concentrations (7 technical replicates). One concentration point overlapped in the high and low concentra-

TABLE 21

Analytical Validation of qPCR primers

| Parameter | Criteria | IBSP | MMP11 | COL10A1 | CTDNEP1 | Method |
|---|---|---|---|---|---|---|
| Specificity. Melt curve. | | 100% | 100% | 100% | 100% | % of area under the melt curve (negative first derivative) corresponding to the expected melting temperature |
| Specificity. Blank Detection, reported in number of PCR cycles. | | 44.5 | 50 | 39.7 | 42.9 | Limit of the blank = (N * 0.95) = 0.5, where N = 90 technical replicates of no template controls |
| Precision (Standard Deviation,) | Standard Deviation <0.167 | 0.027 | 0.012 | 0.013 | 0.009 | Standard deviation (SD) of technical replicates with 10,700 copies/microliters |
| Sensitivity. Limit of detection, reported in number of copies per microliter | | <0.34 | <0.67 | <0.34 | <0.34 | LoD = (mean of no template controls minus standard deviation of no template controls) – $c\beta * SD_s$ |
| Linearity ($R^2$) | $R^2 > 0.95$ | 0.999 | 0.999 | 0.999 | 0.999 | |
| Maximum of the linear range, reported in copies per microliter | $R^2 > 0.98$ | $1 \times 10^6$ | $1 \times 10^6$ | $1 \times 10^6$ | $1 \times 10^6$ | |
| Minimum of the linear range, reported in copies per microliter | $R^2 > 0.98$ | 0.34 | 0.67 | 0.34 | 0.34 | |
| PCR efficiency ($\varepsilon$) | 90-110% | 90% | 91% | 94% | 95% | |

FIG. 7A and FIG. 7B depict charts showing analytic validation of qPCR assays for using clinical-grade reagents. FIG. 7A panel a depicts amplification plots of 20 microliter qPCR reactions. 12 concentrations of synthetic cDNA template (1.1 million to 0 copies per microliter), including 10-fold dilutions for 6 high concentrations (5 technical tion series. Each primer pair includes 24 replicates of no-template controls. Error bars at each cycle represent 95% Confidence Intervals of technical replicates.

FIG. 7A Panel f depicts fluorescence versus cycle plots to determine Ct for IBSP. A 4-parameter linear model was fitted to 5 technical replicates (circles). The maximum of the second derivative was used to define the Ct (CtD2). FIG. 7B panel g depicts threshold cycle versus template dilution plots to calculate linear range. The linear range is defined as the range of concentrations where CtD2 fit a straight line with R-squared >0.995. Red lines indicate 95% Confidence Intervals calculated from 200 bootstraps.

Figure 8A:
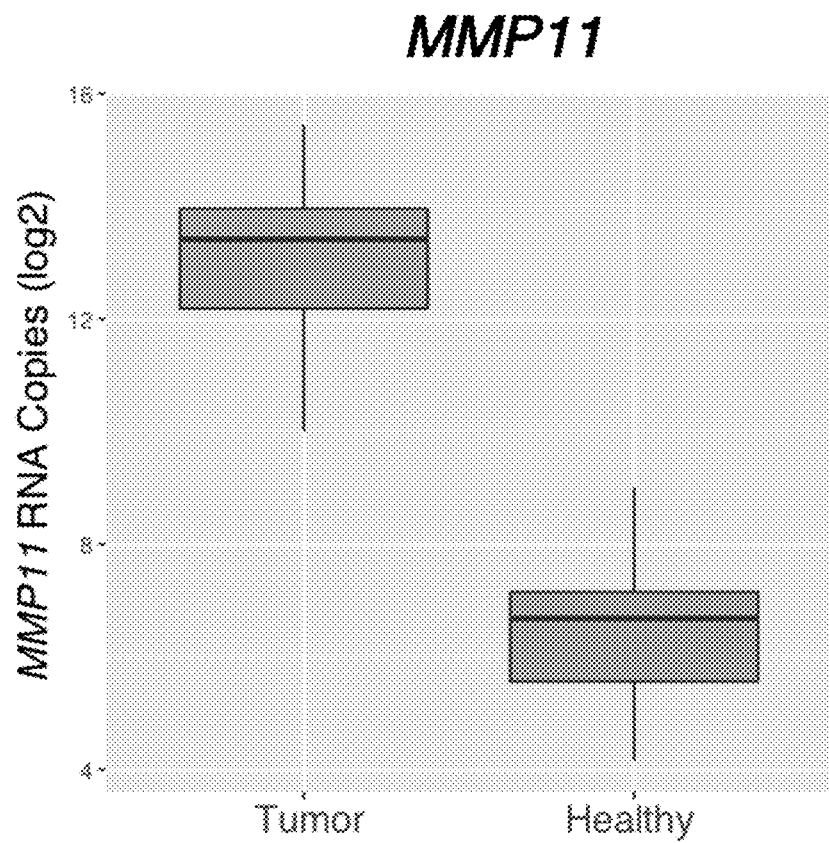
FIG. 8A, FIG. 8B, and FIG. 8C are graphs depicting absolute quantification (RT-qPCR) of the 3 RNAs in the 3-gene set (MMP11, COL10A1, IBSP) in 22 patient samples using Tukey Boxplots. Tukey Boxplots: the thick center line represents the mean, boxes show the interquartile range (Q1-Q3). Cumulative Frequency plots show the distribution of expression in tumor and healthy samples. Panel b depicts absolute quantification (RTqPCR) of RNAs in 22 patient samples using density plots. Density plots illustrate the advantage of combining multiple biomarkers. Copy numbers are adjusted for tumor percent because each tumor specimen contains a differing amount of healthy cells.
Figure 8B:
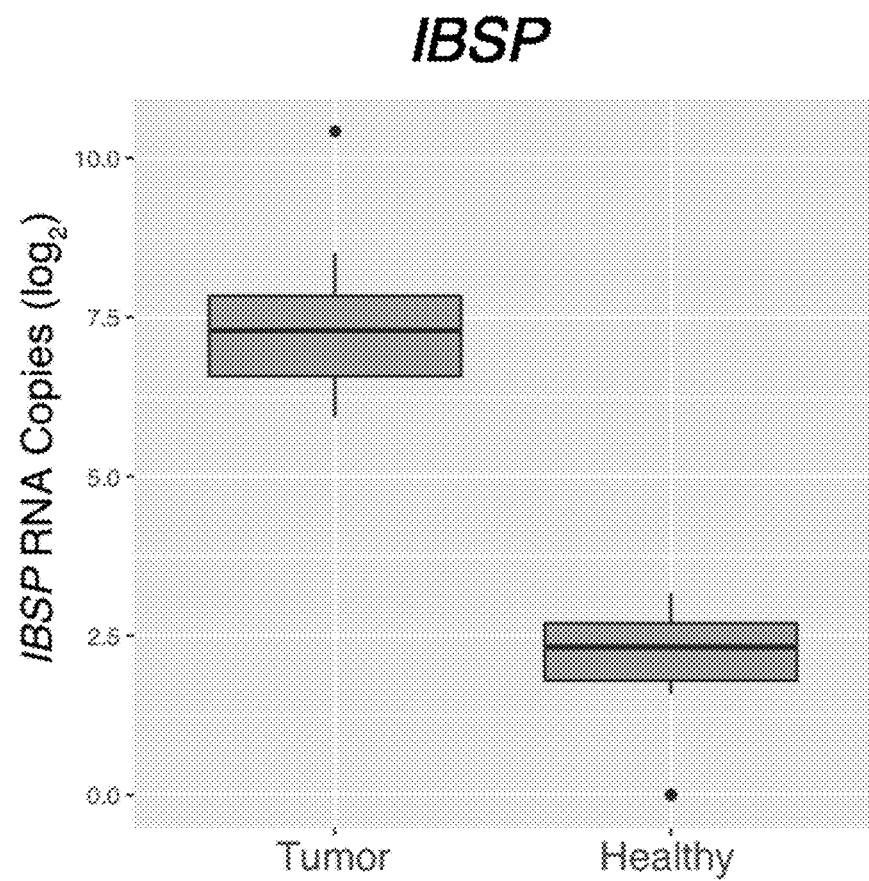
Figure 8C:
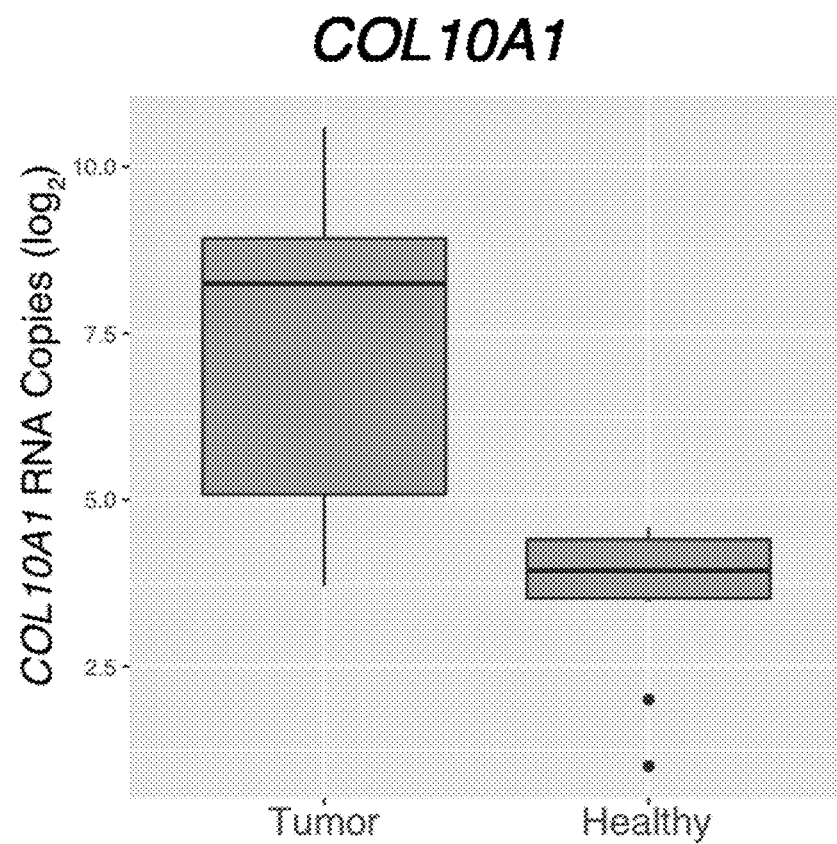

Absolute quantification (qPCR) of RNA from 22 clinical samples confirms that biomarker expression is substantially higher in tumors (TABLE 21). We present adjusted copy numbers for all tumor results from this experiment, including TABLE 21 and FIG. 8. If a tumor sample did not contain 100% tumor (e.g. 95% tumor), the estimated number of copies was adjusted to the equivalent of 100% tumor. The mean number of RNA copies was 34 to 176 times higher in tumor than healthy. On average, expression was 72 to 189 times higher when we compared each tumor to paired healthy tissue from the same patient. One advantage of multi-analyte modeling is that all genes do not need to be elevated in every patient (otherwise the test would only require 1 gene). In each pair of samples, at least one of the tumor biomarkers was markedly elevated. On average, the best of the 3 genes was 273 times higher in the tumor sample than the paired healthy sample.

TABLE 22

Absolute quantification (RTqPCR) of RNA from 22 tumors and healthy tissues.

|  | MMP11 | IBSP | COL10A1 |
|---|---|---|---|
|  | Mean number of copies | | |
| Tumor | 13,472 | 269 | 291 |
| Healthy | 76 | 3 | 12 |
|  | Mean fold-change | | |
|  | 176 | 86 | 34 |
|  | Mean per-patient fold-change | | |
|  | 155 | 189 | 72 | qPCR Test Performance

Figure 9:
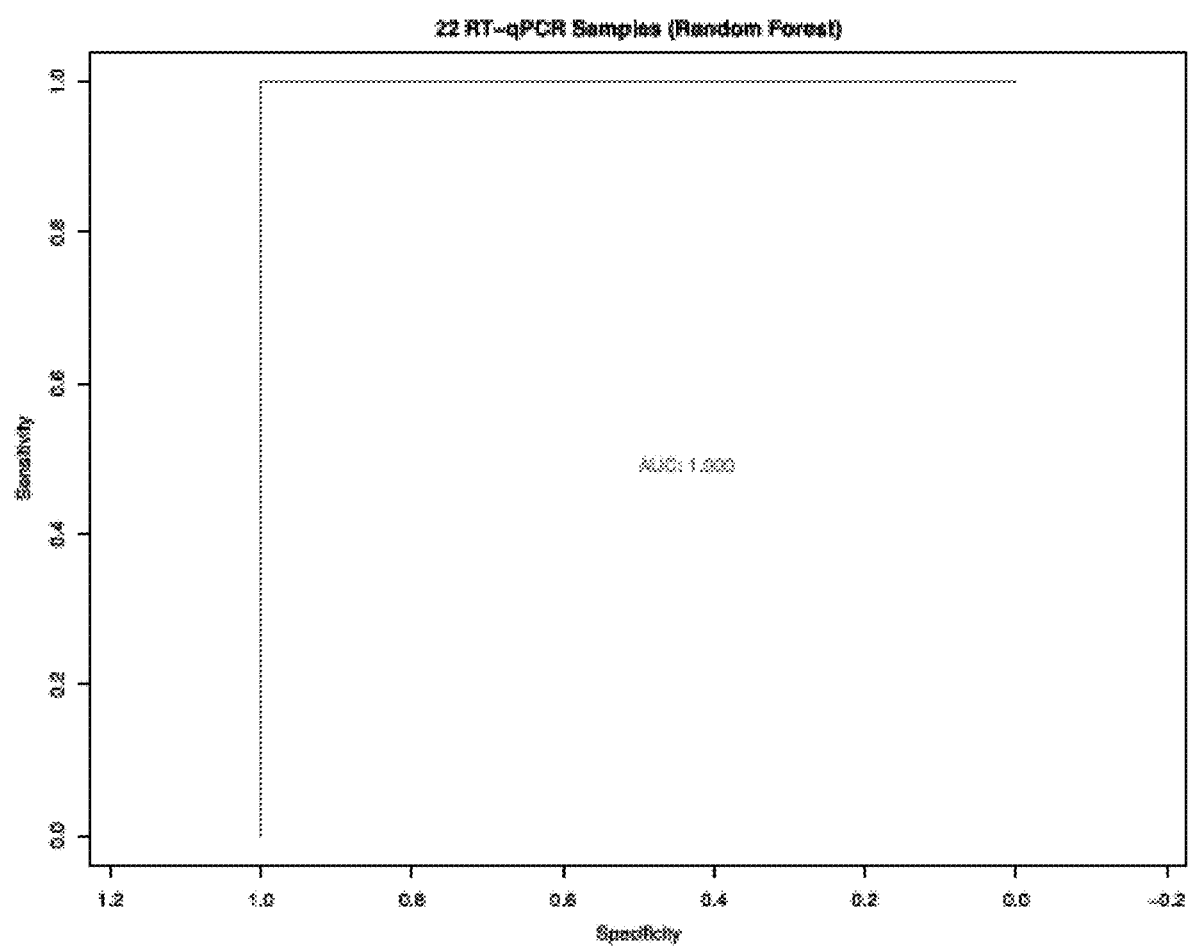
FIG. 9 is a graph depicting a Receiver-Operator Characteristic (ROC) Curve of the 3-Gene Classifier. ROC curves show the tradeoff between sensitivity and specificity over all possible thresholds. The 3-gene classifier uses Random Forest to distinguish between tumor and adjacent healthy tissue. Performance estimates are based on 5-fold cross validation of 22 samples that were analyzed with the disclosed RTqPCR assays.
Figure 10:
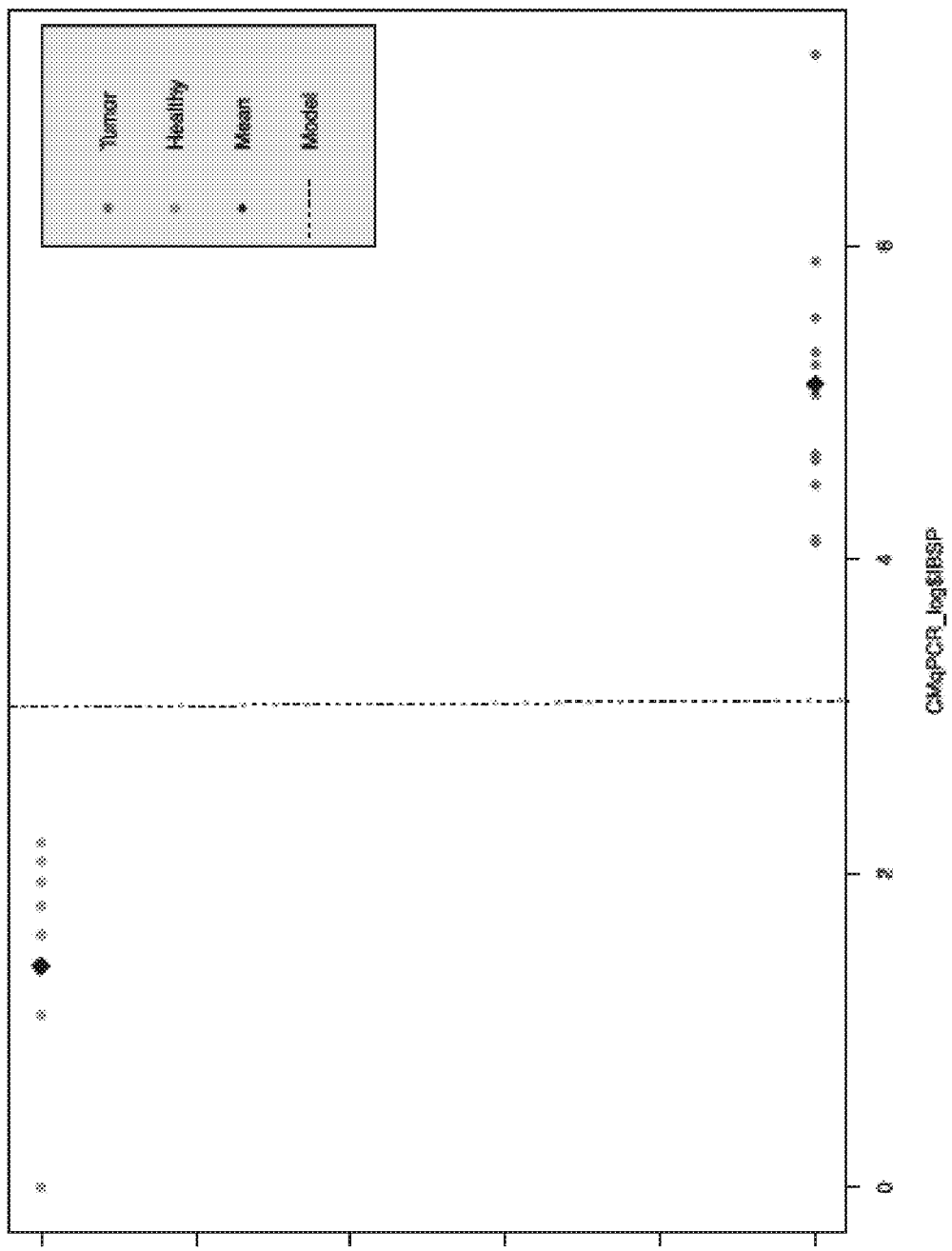
FIG. 10 depicts a plot showing Generalized Linear Model (glm) (dashed line) sample discrimination using IBSP RNA in 22 patient samples, analyzed by the disclosed RTqPCR assay. The disclosed RTqPCR assays can resolve a greater difference in analytes than RNA Seq. The disclosed assays perform so well that a simple linear model can correctly classify 100% of the analyzed samples using a single biomarker. In contrast, RNA Seq required a complex combination of 3 biomarkers, and still did not achieve 100% accuracy.
Figure 11:
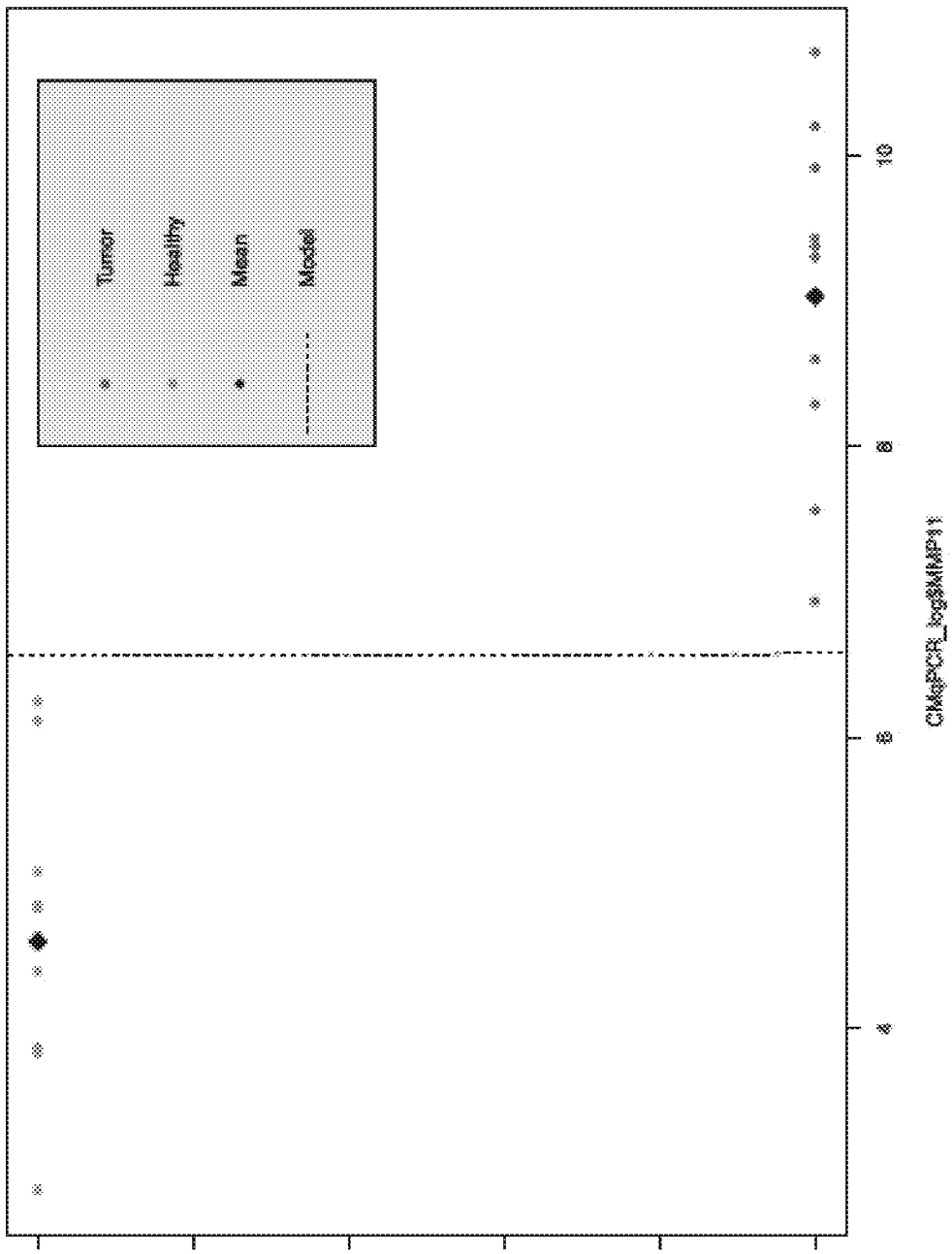
FIG. 11 depicts a plot showing Generalized Linear Model (glm) (dashed line) sample discrimination using MMP11 RNA in 22 patient samples, analyzed by the disclosed RTqPCR assay.
Figure 12:
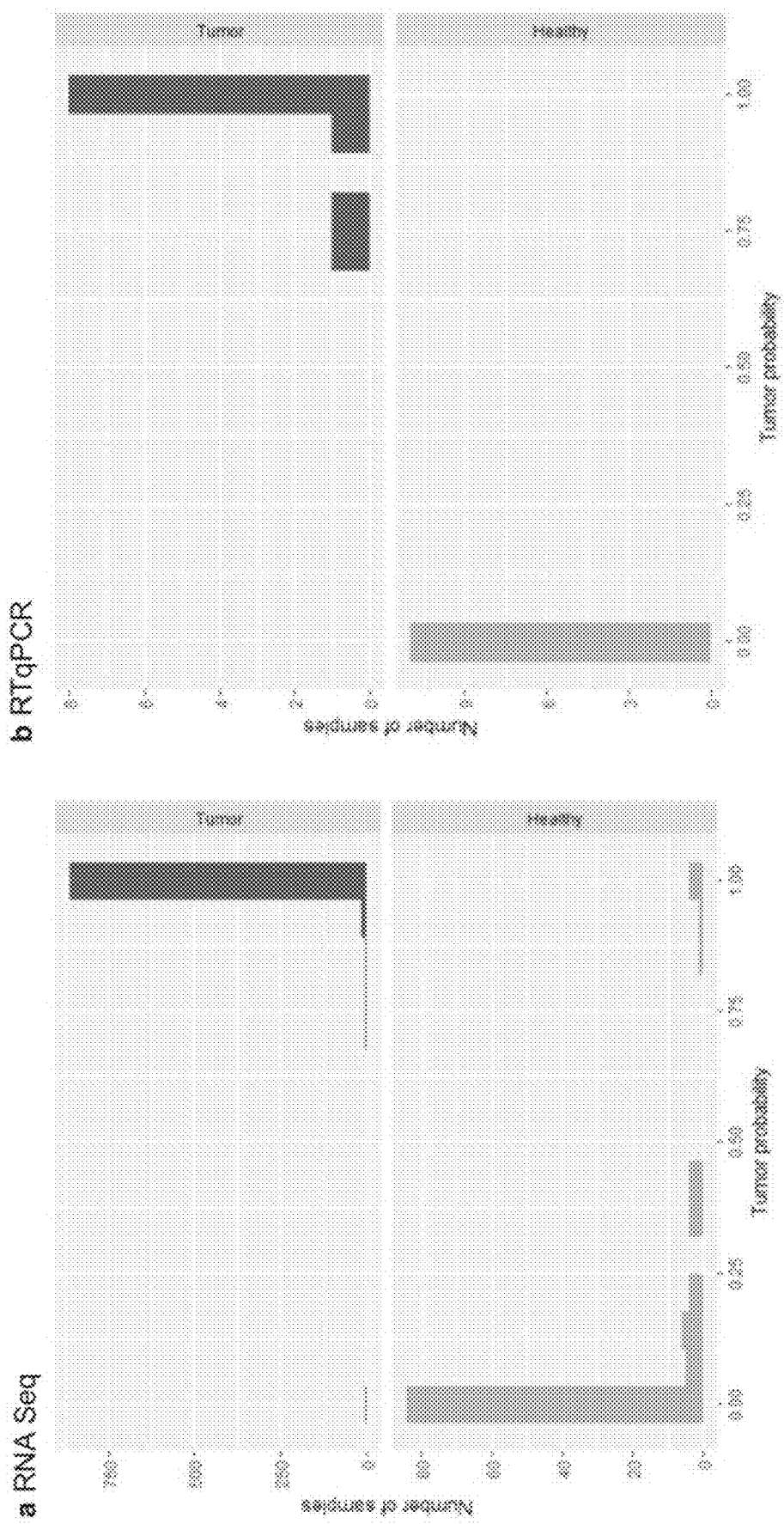
FIG. 12 shows a chart depicting a Tumor Probability Score calculated using the 3-gene classifier described in EXAMPLE 1. The 3-gene classifier uses the Random Forest algorithm to calculate a Tumor Probability Score (T) from zero to one. Panel a shows the T score for RNA Seq samples from 901 tumors (black) and 113 adjacent healthy samples (grey). Panel b shows the T score for RTqPCR samples from 11 tumors (black) and 11 adjacent healthy samples (grey).

A panel of 3 biomarkers correctly classified 100% of the samples as tumor or healthy using Random Forest (EXAMPLE 4), Generalized Linear Models of the Binomial Family (EXAMPLE 5), and Regularized Discriminant Analysis (EXAMPLE 6). FIG. 9 shows the ROC curve for a 3-gene test using Random Forest. In addition, IBSP RNA and MMP11 RNA can unexpectedly be used in combination in a Generalized Linear Model of the Binomial Family to correctly classify 100% of samples (EXAMPLE 7). We further demonstrated that IBSP RNA (FIG. 10) and MMP11 RNA (FIG. 11), correctly classified 100% of samples when used individually in a Generalized Linear Model of the Binomial Family (EXAMPLE 7). Additionally, when COL10A1 RNA was used as an individual biomarker in a Generalized Linear Model of the Binomial Family, the disclosed qPCR assay correctly classified 77.3% of samples as tumor of healthy.

Example 4. Performance of the 3-Gene Test Using the Random Forest (RF) Machine Learning Algorithm, as Determined by 5-Fold Cross Validation 22 samples were analyzed using the disclosed RTqPCR assay as follows:

2 classes of samples were analyzed: RNA from 11 tumor samples and 11 healthy samples were analyzed using the disclosed clinical-grade RTqPCR assays. Resampling was used to estimate performance and statistical parameters of a test generated using Random Forest. Five-fold cross validation showed that the 3-gene RF test had an accuracy of 100%, as shown in TABLE 24.

TABLE 23

|  | Reference | |
|---|---|---|
| Prediction | Tumor | Healthy |
| Tumor | 11 | 0 |
| Healthy | 0 | 11 |

The following parameters were used or determined in the analysis:

TABLE 24

| ROC | Sens | Spec | Accuracy | Kappa |
|---|---|---|---|---|
| 1 | 1 | 1 | 1 | 1 |

> confusionMatrix(data = CMcvRF, CMcvRF$Sample_Type)
Cross-Validated (5-fold) Confusion Matrix Example 5. Performance of the 3-Gene Test Using a Generalized Linear Model (Glm)

22 samples were analyzed using the disclosed RTqPCR assay as follows:

2 classes of samples were analyzed: RNA from 11 tumor samples and 11 healthy samples were analyzed using the disclosed clinical-grade RTqPCR assays. Resampling was used to estimate performance and statistical parameters of a test generated using a Generalized Linear Model in the binomial family. Five-fold cross validation showed that the 3-gene glm test had an accuracy of 100%, as shown in TABLE 26.

TABLE 25

|  | Reference | |
|---|---|---|
| Prediction | Tumor | Healthy |
| Tumor | 11 | 0 |
| Healthy | 0 | 11 |

The following describes R output for this analysis:

TABLE 26

>CMcvGLM_3_log

| ROC | Sens | Spec | Accuracy | Kappa |
|---|---|---|---|---|
| 1 | 1 | 1 | 1 | 1 |

>summary(CMcvGLM_3_log)

Call:
NULL

Deviance Residuals:

| Min | 1Q | Median | 3Q | Max |
|---|---|---|---|---|
| −1.067e−05 | −2.110e−08 | 0.000e+00 | 2.110e−08 | 1.037e−05 |

Coefficients:

| | Estimate Std. | Error z value |
|---|---|---|
| (Intercept) | 8.358e+01 | 2.403e+05 |
| TBSP | −1.763e+01 | 7.812e+04 |
| MMP11 | −4.382e+00 | 5.577e+04 |
| COL10A1 | 7.443e−01 | 4.136e+04 |

(Dispersion parameter for binomial family taken to be 1)
Null deviance: 3.0498e+01 on 21 degrees of freedom
Residual deviance: 3.4098e−10 on 18 degrees of freedom
AIC: 8
Number of Fisher Scoring iterations: 25
>confusionMatrix(data = CMcvGLM_3_log, CMcvGLM_3_log$Sample_Type)
Cross-Validated (5 fold) Confusion Matrix

Example 6. Performance of the 3-Gene Test Using a Regularized Discriminant Analysis (RDA)

22 samples were analyzed using the disclosed RTqPCR assay as follows:

2 classes of samples were analyzed: RNA from 11 tumor samples and 11 healthy samples were analyzed using the disclosed clinical-grade RTqPCR assays. Resampling was used to estimate performance and statistical parameters of a test generated using Regularized Discriminant Analysis (RDA). Five-fold cross validation showed that the 3-gene RDA test had an accuracy of 100%, as shown in TABLE 27.

TABLE 26

| Prediction | Reference | |
|---|---|---|
| | Tumor | Healthy |
| Tumor | 11 | 0 |
| Healthy | 0 | 11 |

The following describes R output for this analysis:

TABLE 27

>CMcvRDA
Regularized Discriminant Analysis

| gamma | lambda | ROC | Sens | Spec | Accuracy | Kappa |
|---|---|---|---|---|---|---|
| 0.0 | 0.0 | 1 | 1.0000000 | 1 | 1.00 | 1.0000000 |
| 0.0 | 0.5 | 1 | 0.6000000 | 1 | 0.82 | 0.6000000 |
| 0.0 | 1.0 | 1 | 0.5333333 | 1 | 0.77 | 0.5321678 |
| 0.5 | 0.0 | 1 | 1.0000000 | 1 | 1.00 | 1.0000000 |
| 0.5 | 0.5 | 1 | 0.5333333 | 1 | 0.77 | 0.5321678 |
| 0.5 | 1.0 | 1 | 0.6333333 | 1 | 0.82 | 0.6321678 |
| 1.0 | 0.0 | 1 | 1.0000000 | 1 | 1.00 | 1.0000000 |
| 1.0 | 0.5 | 1 | 0.6333333 | 1 | 0.82 | 0.6321678 |
| 1.0 | 1.0 | 1 | 0.6333333 | 1 | 0.82 | 0.6321678 |

>confusionMatrix(data = CMcvRDA, CMcvRDA$Sample_Type)

Accuracy was used to select the optimal model using the largest value. The final values used for the model were gamma=0 and lambda=0.

Example 7. Performance of the 2-Gene Test Using a Generalized Linear Model (Glm)

22 samples were analyzed using the disclosed RTqPCR assay as follows:

2 classes of samples were analyzed: RNA from 11 tumor samples and 11 healthy samples were analyzed using the disclosed clinical-grade RTqPCR assays. The two genes were IBSP and MMP11. Resampling was used to estimate performance and statistical parameters of a test generated using a Generalized Linear Model (glm). Five-fold cross validation showed that the 2-gene glm test had an accuracy of 100%, as shown in TABLE 29.

TABLE 28

| Prediction | Reference | |
|---|---|---|
| | Tumor | Healthy |
| Tumor | 11 | 0 |
| Healthy | 0 | 11 |

The following describes R output for this analysis:

TABLE 29

>CMcvGLM_2_genes
Generalized Linear Model

| ROC | Sens | Spec | Accuracy | Kappa |
|---|---|---|---|---|
| 1 | 1 | 1 | 1 | 1 |

>summary(CMcvGLM_2_genes)

Call:
NULL

Deviance Residuals:

| Min | 1Q | Median | 3Q | Max |
|---|---|---|---|---|
| −3.200e−05 | −2.100e−08 | 7.230e−07 | 4.130e−06 | 2.197e−05 |

Coefficients:

| | Estimate Std. | Error z value | Pr(>|z|) | |
|---|---|---|---|---|
| (Intercept) | 2.810e+01 | 2.988e+04 | 0.001 | 0.999 |
| IBSP | −4.418e−01 | 7.770e+02 | −0.001 | 1.000 |
| MMP11 | −5.536e−03 | 1.426e+01 | 0.000 | 1.000 |

TABLE 29-continued (Dispersion parameter for binomial family taken to be 1)
Null deviance: 3.0498e+01 on 21 degrees of freedom
Residual deviance: 2.2434e−09 on 19 degrees of freedom
AIC: 6
Number of Fisher Scoring iterations: 25
>confusionMatrix(data = CMcvGLM_2_genes,
CMcvGLM_2_genes$Sample_Type)

Example 8. Analysis of Validation Data for 3-Gene Test

Data from 1,211 samples using 3 different technologies was used to validate a 3-gene test. Cross-validation was performed using 939 RNA Seq samples. Since cross-validation uses independent test sets, one can mathematically prove that it is a reliable estimate of performance. This can be confirmed with a suite of negative controls. Similar expression patterns have been confirmed with RNA Seq and microarray, confirming that the signals are not platform specific. Independent test sets were then analyzed to determined performance on early and late stage tumors, specifically, test sets 1 (75 early-stage samples) and independent test set 2 (175 late-stage samples).

The results of these analyses were extremely surprising in light of the current beliefs about breast cancer biology. To further investigate these surprising results, we used clinical-grade reagents to develop and validate RTqPCR assays for the selected mRNAs. We analyzed 22 samples with our assays. This represents the third independent set of samples. Using the disclosed RTqPCR assays, the selected biomarkers clearly demarcate tumor and healthy, and even provides more separation between tumor and healthy than RNA Seq.

We used predictive models to combine the biomarkers and set clinically actionable thresholds. We discovered that multiple predictive models can achieve excellent performance. For example, when all 3 biomarkers are detected using the disclosed RTqPCR assays, Random Forest, Regularized Discriminant Analysis, and Generalized Linear Models of the Binomial Family can correctly classify 100% of the samples as tumor or healthy. In addition, we unexpectedly discovered that when TBSP RNA (FIG. 10) and MMP11 RNA (FIG. 11) are detected using the disclosed assays, they can be used individually to correctly classify 100% of samples. These experiments firmly establish that the signal is tumor-specific and reproducible across three detection technologies.

Example 9. Evaluation of Surgical Margins

As demonstrated herein, the markers and methods can be used to improve the evaluation of surgical margins. In this case, cells are collected from the surface of a surgical specimen and the disclosed assays are used to detect the disclosed markers. A number of methods can be used to collect cells from the surface of a surgical specimen. As non-limiting examples, cells can be collected using a surface with a functionalized surface, such as a poly-lysine coated touch imprint cytology slide. Cells could also be collected using a membrane, such as a nitrocellulose membrane. In addition, cells could be collected using a sharp or blunt instrument, such as scrape preparations, which are routinely performed for pathologic examination.

The markers and methods could be used to screen patients for invasive breast cancer. Specimens can be collected using nipple aspirates or ductal lavage, where the mammary ducts and glands are flushed with fluid and aspirated, sometimes following brief hormonal stimulation. Existing screening methods suffer from poor sensitivity or specificity, and often exposure patients to radiation. Ductal lavage is the preferred screening method for some surgeons, because it directly samples the ducts and glands that give rise to epithelial tumors like adenocarcinomas. However, the analysis of rare tumor cells is not ideal. Microscopic detection of tumors has the best performance when the tumor is analyzed in the context of its surrounding healthy tissue. In fact, the name histopathology derives from the Greek histos, meaning tissue. When cells are scraped or flushed into a suspension, they are no longer in the context of surrounding tissue. Ductal lavage is therefore a promising screening strategy that is currently limited by the microscopic analysis required to detect rare or isolated breast cancer cells. Molecular analysis is particularly well suited to solve this problem because it does not rely on visual analysis, and does not require tumor to be evaluated in the context of healthy tissue. The disclosed markers and methods could therefore be used as a screening tool to determine whether there are invasive cancer cells present in screened patients.

The markers and methods could be used to detect or diagnose invasive adenocarcinoma from biopsies of the breast. Biopsies could include core biopsies, punch biopsies, incisional biopsies and excisional biopsies. In many biopsy samples, the procedure did not collect a sufficient amount of cells, or the tissue architecture has been disrupted, making it challenging to reach a definitive histopathologic or cytological diagnosis. These challenging cases are prime examples of the advantage of molecular analysis. Molecular analysis does not require abundant tissue, and does not require intact tissue structures in order to detect the disclosed signatures of invasive cancer.

Example 10. Identifying Pre-Cancerous Lesions

The disclosed markers and methods can be used to establish a new diagnostic paradigm for pre-cancerous lesions. Lesions like ductal carcinoma in situ (DCIS) and lobular carcinoma in situ (LCIS) are currently considered pre-cancerous lesions or risk factors for invasive cancer. In only some cases do they develop into invasive cancer, but there is currently no way to identify which lesions have invasive potential. Moreover, precursor lesions are only analyzed by a few microscopic sections. The current diagnostic paradigm for precancerous lesions is based on whether a pathologist happens to observe cells that penetrate the basement membrane on the few slides that they examine. There is therefore thought to be a subset of pre-cancerous lesions with undiagnosed invasive potential. The disclosed markers and methods provide a molecular analysis of invasiveness that could identify those precancerous lesions with invasive potential. In addition, the disclosed methods can be performed on a more representative portion of the specimen than 3 microscopic sections. As non-limiting examples, tissue or biopsy specimens can be morcellated, digested enzymatically, and/or chemically lysed to release the disclosed biomarkers, which can then be detected using the disclosed methods. In this way, the disclosed biomarkers represent a strategy to stratify patients by their risk for developing invasive cancer.

Pathologic Complete Response (pCR) is the absence of residual cancer in a solid tissue specimen, obtained from a patient who was previously diagnosed with invasive cancer. pCR is used as a surrogate endpoint for solid tumor neoadjuvant therapies. However, FDA guidance acknowledges that there is an "uncertain relationship between pCR and long-term outcome," and emphasizes the possibility "that a neoadjuvant trial could fail to demonstrate a significant difference in pCR rates and result in abandoned development of a drug that is, in fact, active in the adjuvant or metastatic setting." A 2016 analysis found that pCR is the primary endpoint of ~50% of enrolling phase II rectal cancer trials, and 45% of phase III preoperative breast cancer trials. However, there are reasons to continually improve the metrics and technologies that serve as surrogates for long-term outcomes. Hormonal therapies exemplify treatments that substantially improve survival, with only minimal impacts on pCR. Conversely, pertuzumab was approved by the FDA following a phase II randomized clinical trial that demonstrated an improvement in pCR. Yet, to date, there have been no data that suggest pertuzumab improves event-free survival, disease-free survival, or overall survival in the neoadjuvant setting. These cautionary notes underscore the importance of efforts to vigorously improve the detection of minimal residual disease and the need to develop a molecular complete response (mCR) assay.

Histopathology has been the best way to examine tumors for over a century, but it is not ideal to hunt for minimal residual disease (MRD). While FDA guidance documents emphasize the importance of compressive sectioning, sampling by pathology is woefully underpowered to provide a statistically meaningful analysis of the specimen (e.g. in practice, only a few sections are used to hunt for elusive residual tumor).

Detecting metastases to lymph nodes exemplifies the challenges of detecting breast cancer MRD using microscopy. Donald Weaver wrote that "It is quite clear that the more sections we evaluate from SLNs the more metastases we identify; however, it is impractical to expect the practicing pathologist to mount, stain, and microscopically examine every section through the SLN paraffin blocks." Nevertheless, "when we fail to examine the entire node, we as pathologists miss metastases that are present."

Older recommendations of sectioning lymph nodes in intervals is no longer considered appropriate because thicker intervals (3-4 mm intervals) mean less metastases are detected. Examining a greater number of thinner sections detects more metastases. When thin sectioning was adopted in the United States between 1995 to 1999, node positive Stage II breast cancer increased from 60 to 80 cases per 100,000 population-based individuals in the SEER national cancer database.

EMBODIMENTS

Embodiment 1

A method of distinguishing a cancer from adjacent healthy tissue, said method comprising: a) obtaining a specimen from a human subject, b) collecting a sample from said specimen, c) detecting a presence of a set of markers in said sample by performing an amplification reaction in a plurality of polynucleotides from said sample, wherein said set of markers is selected from the group consisting essentially of: Matrix Metallopeptidase 11 (MMP11), integrin binding sialoprotein (IBSP), and collagen type X alpha 1 chain (COL10A1); and d) distinguishing said cancer when a threshold level of said set of markers is detected.

Embodiment 2

The method of Embodiment 1, wherein said amplification reaction is a PCR reaction.

Embodiment 3

The method of Embodiment 1, wherein said PCR reaction is a qPCR reaction.

Embodiment 4

The method of Embodiment 1, wherein said PCR reaction is a RTqPCR reaction.

Embodiment 5

The method of Embodiment 1, wherein said method can distinguish said cancer in at least 10 ng of said plurality of polynucleotides from sample.

Embodiment 6

The method of Embodiment 1, wherein said method can distinguish said cancer in at least 100 mg of said sample.

Embodiment 7

The method of Embodiment 1, wherein said amplification reaction uses at least one primer sequence that has at least 90% identity to SEQ ID NO: 1-SEQ ID NO: 356.

Embodiment 8

The method of Embodiment 1, wherein said sample is frozen.

Embodiment 9

The method of Embodiment 1, wherein said sample is a biopsy sample.

Embodiment 10

The method of Embodiment 9, wherein said biopsy is a liquid biopsy.

Embodiment 11

The method of Embodiment 9, wherein said biopsy is a solid tissue biopsy.

Embodiment 12

The method of Embodiment 1[00210], wherein said cancer is breast cancer.

Embodiment 13

The method of Embodiment 12, wherein said breast cancer is invasive breast cancer.

Embodiment 14

The method of Embodiment [00222], wherein said method distinguishes said breast cancer from adjacent healthy tissue with greater than 96% accuracy.

Embodiment 15

The method of Embodiment [00222], wherein said method distinguishes said breast cancer from adjacent healthy tissue with greater than 96% sensitivity.

Embodiment 16

The method of Embodiment [00222], wherein said method distinguishes said breast cancer from adjacent healthy tissue with greater than 94% specificity.

Embodiment 17

The method of Embodiment 1, wherein said cancer is a urothelial carcinoma.

Embodiment 18

The method of Embodiment [00210], further comprising outputting a percentage of said plurality of polynucleotides expressing said markers from said sample.

Embodiment 19

The method of Embodiment [00210], further comprising comparing said set of markers from said sample to said set of markers from said a control sample.

Embodiment 20

The method of Embodiment [00228], wherein said control sample is a second sample from said human subject.

Embodiment 21

The method of Embodiment 21, further comprising performing a second assay to distinguish said cancer.

Embodiment 22

The method of Embodiment 21, wherein said second assay is an immunohistochemistry assay.

Embodiment 23

The method of Embodiment [00210], wherein said threshold level of said MMP11 is 1,000 copies.

Embodiment 24

The method of Embodiment 1, wherein said threshold level of said IBSP is 25 copies.

Embodiment 25

The method of Embodiment [00210], wherein said threshold level of said COL10A1 is 700 copies.

Embodiment 26

The method of Embodiment [00210], wherein said set of markers is selected from the group consisting of: Matrix Metallopeptidase 11 (MMP11), integrin binding sialoprotein (IBSP), and collagen type X alpha 1 chain (COL10A1).

Embodiment 27

A kit comprising, at least one primer sequence that has at least 90% identity to SEQ ID NO: 1-SEQ ID NO: 356 and a buffer system.

Embodiment 28

The kit of claim [00236], wherein said buffer system is a PCR buffer system.

Embodiment 29

Isolated nucleic acid comprising a primer sequence that has at least 90% identity to SEQ ID NO: 1-SEQ ID NO: 356.

Embodiment 30

A method of identifying a biomarker for a cancer comprising:
(a) analyzing, by a computer system, a cohort of biomarkers from a population of subjects afflicted with a cancer;
(b) identifying, by said computer system, a first subset from said cohort of said biomarkers that has at least a 3-fold higher expression level in said cancer as compared to a healthy control biomarker;
(c) identifying, by a computer system, a second subset from said first subset of said biomarkers that provides a false discovery rate for said cancer that is less than a $10^{-6}$ rate;
(d) instructing said computer system to use at least one biomarker from said second subset of said biomarkers as a training set of a machine learning algorithm; and
(e) outputting one or more biomarkers that identify said cancer within a 95% confidence interval.

Embodiment 31

The method of Embodiment 30, wherein said cancer is breast cancer.

Embodiment 32

The method of Embodiment 31, wherein said breast cancer is invasive breast cancer.

Embodiment 33

The method of Embodiment 30, wherein said one or more biomarkers identify said cancer with greater than 96% accuracy.

Embodiment 34

The method of Embodiment 30, wherein said one or more biomarkers identify said cancer with greater than 96% sensitivity.

Embodiment 35

The method of Embodiment 30, wherein said one or more biomarkers identify said cancer with greater than 94% specificity.

Embodiment 36

The method of Embodiment 30, wherein said training set comprises one or more markers selected from the group consisting essentially of: Matrix Metallopeptidase 11 (MMP11), integrin binding sialoprotein (IBSP), and collagen type X alpha 1 chain (COL10A1).

Embodiment 37

A method of diagnosing a cancer in a human subject, said method comprising:
(a) obtaining a sample from said human subject,
(b) detecting whether one or more markers are present in said sample by performing an amplification reaction in a plurality of polynucleotides from said sample and detecting the presence of said one or more markers, wherein said one or more markers are selected from the group consisting of: Matrix Metallopeptidase 11 (MMP11), integrin binding sialoprotein (IBSP), and collagen type X alpha 1 chain (COL10A1); and
(c) distinguishing said cancer when a threshold level of one or more said markers is detected.

Embodiment 38

A method of detecting Matrix Metallopeptidase 11 (MMP11) in a human subject, said method comprising:
(a) obtaining a sample from said human subject; and
(b) detecting whether MMP11 is present in said sample by performing an amplification reaction in a plurality of polynucleotides from said sample and detecting the presence of an MMP11 transcript.

Embodiment 39

A method of detecting integrin binding sialoprotein (IBSP) in a human subject, said method comprising:
(c) obtaining a sample from said human subject; and
(d) detecting whether IBSP is present in said sample by performing an amplification reaction in a plurality of polynucleotides from said sample and detecting the presence of an IBSP transcript.

Embodiment 40

A method of detecting collagen type X alpha 1 chain (COL10A1) in a human subject, said method comprising:
(e) obtaining a sample from said human subject; and
(f) detecting whether COL10A1 is present in said sample by performing an amplification reaction in a plurality of polynucleotides from said sample and detecting the presence of an COL10A1 transcript.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

What is claimed is:

1. A method for detecting residual breast cancer from a lumpectomy specimen from a human subject, said method comprising:
   (a) obtaining cells from a surface of the lumpectomy specimen from the human subject, wherein said specimen was obtained from said human subject as part of a surgical treatment for breast cancer;
   (b) detecting a presence of a set of mRNA markers in said cells from said surface of said lumpectomy specimen at least in part by amplifying a plurality of polynucleotides from said cells from said surface of said lumpectomy specimen, wherein said set of markers comprises Matrix Metallopeptidase 11 (MMP11), integrin binding sialoprotein (IBSP), and collagen type X alpha 1 chain (COL10A1);
   (c) computing a specimen score for said specimen based on the amount of said set of mRNA markers using a machine learning algorithm, wherein said machine learning algorithm has been trained using an input dataset that contains the amount of said mRNA markers in specimens that contain tumor and the amount of said mRNA markers in specimens that do not contain tumor; and
   (d) detecting said residual breast cancer by comparing said specimen score to a score threshold, wherein said score threshold indicates whether the specimen is comparable to specimens that contain tumor or specimens that do not contain tumor;
   (e) thereby determining the presence of residual breast cancer when the specimen score is greater than the score threshold, and determining the absence of residual breast cancer when the specimen score is less than or equal to the score threshold,
   wherein said determining has:
      a minimum diagnostic accuracy of 90% for distinguishing tissue containing tumor from tissue that does not contain tumor,
      a minimum diagnostic sensitivity of 90% for distinguishing tissue containing tumor from tissue that does not contain tumor, or
      a minimum diagnostic specificity of 90% for distinguishing tissue containing tumor from tissue that does not contain tumor.

2. The method of claim 1, wherein said plurality of polynucleotides comprise RNA.

3. The method of claim 1, wherein said plurality of polynucleotides comprise cDNA.

4. The method of claim 1, wherein said detecting comprises using a DNA-intercalating dye.

5. The method of claim 1, wherein said detecting comprises using a fluorescent probe.

6. The method of claim 5, wherein said fluorescent probe is a TaqMan probe.

7. The method of claim 1, wherein said amplifying comprises a PCR reaction.

8. The method of claim 7, wherein said PCR reaction is a qPCR reaction.

9. The method of claim 7, wherein said PCR reaction is a RTqPCR reaction.

10. The method of claim 1, wherein said method can distinguish said breast cancer in at least 10 ng of said plurality of polynucleotides from said surface of said specimen.

11. The method of claim 1, wherein said method can distinguish said breast cancer in at least 250 cells from said surface of said of said lumpectomy specimen.

12. The method of claim 1, wherein said lumpectomy specimen is a frozen lumpectomy specimen, a fresh lumpectomy specimen, or a fixed lumpectomy specimen.

13. The method of claim 1, wherein said lumpectomy specimen is a biopsy lumpectomy specimen.

14. The method of claim 13, wherein said biopsy is a solid tissue biopsy or a surgical excision.

15. The method of claim 1, wherein said cells from said surface of said lumpectomy specimen are obtained by imprint cytology.

16. The method of claim 15, wherein said imprint cytology is a touch-preparation.

17. The method of claim 1, wherein said lumpectomy specimen is obtained by scrape preparation, a nipple aspiration, or a ductal lavage.

18. The method of claim 1, wherein said breast cancer is selected from the group consisting of: invasive adenocarcinoma, invasive ductal breast cancer, and invasive lobular breast cancer.

19. The method of claim 18, wherein said algorithm detects said residual breast cancer with a minimum of 90% diagnostic accuracy.

20. The method of claim 18, wherein said algorithm detects said residual breast cancer with a minimum of 90% diagnostic sensitivity.

21. The method of claim 18, wherein said algorithm detects said residual breast cancer with a minimum of 90% diagnostic specificity.

22. The method of claim 1, wherein said method quantitates an amount of said breast cancer.

23. The method of claim 22, further comprising outputting a percentage of said plurality of polynucleotides expressing said markers from said specimen.

24. The method of claim 1, further comprising performing a second assay to distinguish said breast cancer.

25. The method of claim 24, wherein said second assay is an immunohistochemistry assay.

26. The method of claim 1, wherein said amplifying comprises a singleplex reaction.

27. The method of claim 1, wherein said amplifying comprises a multiplex reaction.

28. The method of claim 1, wherein said trained supervised machine learning classifier is an SMO, a Naïve Bayes, a J48 Decision tree, a Lazy-IBk, a Multilayer perceptron neural network, or a random forest classifier.

29. The method of claim 1, wherein said set of markers consists essentially of Matrix Metallopeptidase 11 (MMP11), integrin binding sialoprotein (IBSP), and collagen type X alpha 1 chain (COL10A1).

* * * * *